United States Patent
David et al.

(10) Patent No.: US 7,247,713 B2
(45) Date of Patent: Jul. 24, 2007

(54) SYMMETRICAL DIAZO COMPOUNDS CONTAINING 2-PYRIDINIUM GROUPS AND CATIONIC OR NON-CATIONIC LINKER, COMPOSITIONS COMPRISING THEM, METHOD OF COLORING, AND DEVICE

(75) Inventors: Hervé David, la Varenne Saint Hilaire (FR); Andrew Greaves, Montevrain (FR); Nicolas Daubresse, la Celles St. Cloud (FR)

(73) Assignee: L'Oreal, S.A., Paris (FR)

( * ) Notice: Subject to any disclaimer, the term of this patent is extended or adjusted under 35 U.S.C. 154(b) by 46 days.

(21) Appl. No.: 11/300,271

(22) Filed: Dec. 15, 2005

(65) Prior Publication Data

US 2006/0156488 A1 Jul. 20, 2006

Related U.S. Application Data

(60) Provisional application No. 60/646,974, filed on Jan. 27, 2005.

(30) Foreign Application Priority Data

Dec. 15, 2004 (FR) .................................. 04 52999

(51) Int. Cl.
*C09B 44/12* (2006.01)
*A61Q 5/10* (2006.01)

(52) U.S. Cl. ...................... 534/608; 8/405; 8/426; 8/655

(58) Field of Classification Search ............... 534/608; 8/405, 426, 655
See application file for complete search history.

(56) References Cited

U.S. PATENT DOCUMENTS

| | | | |
|---|---|---|---|
| 3,151,106 A | 9/1964 | Tsang et al. | |
| RE30,199 E | 1/1980 | Rose et al. | |
| 4,557,732 A | 12/1985 | Hä hnke et al. | |
| 4,823,985 A | 4/1989 | Grollier et al. | |
| 5,151,106 A | 9/1992 | Bhaumik et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,708,151 A | 1/1998 | Mockli | |
| 5,733,343 A | 3/1998 | Mockli | |
| 5,766,576 A | 6/1998 | Löwe et al. | |
| 5,792,221 A | 8/1998 | Lagrange et al. | |
| 5,852,179 A | 12/1998 | Dado | |
| 5,888,252 A | 3/1999 | Mockli | |
| 6,099,592 A | 8/2000 | Vidal et al. | |
| 6,099,593 A | 8/2000 | Terranova et al. | |
| 6,270,533 B1 | 8/2001 | Genet et al. | |
| 6,284,003 B1 | 9/2001 | Rose et al. | |
| 6,338,741 B1 | 1/2002 | Vidal et al. | |
| 6,645,258 B2 | 11/2003 | Vidal et al. | |
| 6,824,570 B2 | 11/2004 | Vidal et al. | |
| 6,881,230 B2 | 4/2005 | Vidal | |
| 6,884,265 B2 | 4/2005 | Vidal et al. | |
| 6,884,267 B2 | 4/2005 | Vidal et al. | |
| 6,893,471 B2 | 5/2005 | Vidal | |
| 7,001,436 B2 | 2/2006 | Vidal et al. | |
| 7,022,143 B2 | 4/2006 | Vidal et al. | |
| 7,166,710 B2 * | 1/2007 | Eliu et al. | ........... 534/588 |
| 2002/0050013 A1 | 5/2002 | Vidal et al. | |
| 2002/0095732 A1 | 7/2002 | Kravtchenko et al. | |
| 2002/0187435 A1 | 12/2002 | Manakli et al. | |
| 2003/0084516 A9 | 5/2003 | Kravtchenko et al. | |

(Continued)

FOREIGN PATENT DOCUMENTS

DE          23 59 399 A1    6/1975

(Continued)

OTHER PUBLICATIONS

English Language Derwent Abstract for DE 38 43 892 A1.

(Continued)

*Primary Examiner*—Fiona T. Powers
(74) *Attorney, Agent, or Firm*—Finnegan, Henderson, Farabow, Garrett, & Dunner, L.L.P.

(57) ABSTRACT

The present disclosure relates to symmetrical cationic diazo compounds of formula (I), the resonance forms, and also the acid addition salts and/or the solvates thereof:

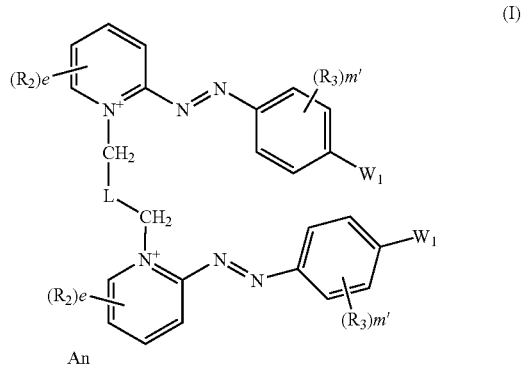

(I)

The present disclosure further relates to dyeing compositions comprising such compounds as a direct dye in a medium appropriate for the dyeing of keratin fibers, and also to a method of coloring keratin fibers that employs this composition, and a multi-compartment kit containing such compositions.

37 Claims, No Drawings

U.S. PATENT DOCUMENTS

| | | |
|---|---|---|
| 2003/0106169 A1 | 6/2003 | Vidal et al. |
| 2004/0093675 A1 | 5/2004 | Vidal et al. |
| 2004/0093676 A1 | 5/2004 | Vidal et al. |
| 2004/0107513 A1 | 6/2004 | Vidal et al. |
| 2004/0127692 A1 | 7/2004 | David et al. |
| 2004/0143911 A1 | 7/2004 | Vidal |
| 2004/0168263 A1 | 9/2004 | Vidal |
| 2004/0187225 A1 | 9/2004 | Vidal et al. |
| 2004/0187228 A1 | 9/2004 | Lagrange |
| 2004/0200009 A1 | 10/2004 | Vidal |
| 2004/0221399 A1 | 11/2004 | Cotteret et al. |
| 2004/0244123 A1 | 12/2004 | Vidal et al. |
| 2004/0244124 A1 | 12/2004 | Plos et al. |
| 2005/0008594 A1 | 1/2005 | Plos et al. |
| 2005/0039269 A1 | 2/2005 | Plos et al. |
| 2006/0149044 A1* | 7/2006 | David et al. ............ 534/766 |

FOREIGN PATENT DOCUMENTS

| | | |
|---|---|---|
| DE | 38 43 892 A1 | 6/1990 |
| DE | 41 33 957 A1 | 4/1993 |
| DE | 195 43 988 A1 | 5/1997 |
| EP | 0 770 375 B1 | 5/1997 |
| EP | 0 714 954 B1 | 9/2002 |
| EP | 1 428 505 A1 | 6/2004 |
| EP | 1 433 474 A1 | 6/2004 |
| EP | 1 219 683 B1 | 7/2004 |
| EP | 1 464 327 A1 | 10/2004 |
| FR | 2 586 913 A1 | 3/1987 |
| FR | 2 692 572 A1 | 12/1993 |
| FR | 2 733 749 A1 | 11/1996 |
| FR | 2 750 048 A1 | 12/1997 |
| FR | 2 807 650 A1 | 10/2001 |
| FR | 2 822 693 A1 | 10/2002 |
| FR | 2 822 694 A1 | 10/2002 |
| FR | 2 822 696 A1 | 10/2002 |
| FR | 2 822 698 | 10/2002 |
| FR | 2 825 625 | 12/2002 |
| FR | 2 825 702 A1 | 12/2002 |
| FR | 2 829 926 A1 | 3/2003 |
| FR | 2 844 269 A1 | 3/2004 |
| GB | 1 026 978 | 4/1966 |
| GB | 1 153 196 | 5/1969 |
| JP | 02-19576 | 1/1990 |
| JP | 05-163124 | 6/1993 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 99/03834 A2 | 1/1999 |
| WO | WO 02/30374 A1 | 4/2002 |
| WO | WO 02/078596 | 10/2002 |
| WO | WO 02/078660 A1 | 10/2002 |
| WO | WO 02/080869 A2 | 12/2002 |
| WO | WO 02/100366 A2 | 12/2002 |
| WO | WO 02/100369 A2 | 12/2002 |
| WO | WO 02/100834 A1 | 12/2002 |
| WO | WO 02100368 A1 | 12/2002 |
| WO | WO 04/083312 A2 | 9/2004 |

OTHER PUBLICATIONS

English Language Derwent Abstract for EP 0 770 375 B1.
English Language Derwent Abstract for JP 05-163124.
English Language Derwent Abstract for JP 2-19576.
French Search Report for French Patent Application No. FR 04/52998, priority document for co-pending U.S. Appl. No. 11/300,314, Aug. 3, 2005.
French Search Report for French Patent Application No. FR 04/52999, priority document for co-pending U.S. Appl. No. 11/300,271, Aug. 1, 2005.
French Search Report for French Patent Application No. FR 04/53000, priority document for co-pending U.S. Appl. No. 11/300,284, Aug. 3, 2005.
French Search Report for French Patent Application No. FR 04/53002, priority document for co-pending U.S. Appl. No. 11/300,300, Sep. 16, 2005.
French Search Report for French Patent Application No. FR 04/53006, priority document for co-pending U.S. Appl. No. 11/300,432, Sep. 19, 2005.
French Search Report for French Patent Application No. FR 04/53008, priority document for co-pending U.S. Appl. No. 11/300,303, Aug. 24, 2005.
French Search Report for French Patent Application No. FR 04/53005, priority document for co-pending U.S. Appl. No. 11/300,512, Aug. 23, 2005.
Co-pending U.S. Appl. No. 11/300,314, filed Dec. 15, 2005, by inventors David et al.
Co-pending U.S. Appl. No. 11/300,284, filed Dec. 15, 2005, by inventors David et al.
Co-pending U.S. Appl. No. 11/300,300, filed Dec. 15, 2005, by inventors David et al.
Co-pending U.S. Appl. No. 11/300,432, filed Dec. 15, 2005, by inventors David et al.
Co-pending U.S. Appl. No. 11/300,303, filed Dec. 15, 2005, by inventors David et al.
Co-pending U.S. Appl. No. 11/300,512, filed Dec. 15, 2005, by inventors David et al.
E. Buncel et al.; "Studies of Azo and Azoxy Dyestuffs— 16† Investigations of the Protonation and Tautomeric Equilibria of 4-(p'-Hydroxyphenylazo)Pyridine and Related Substrates;" *Tetrahedron*; (1983); pp. 1091-1101; vol. 39, No. 7.
I. Onyido et al.; "Heteroaromatic Azo-Activated Nucleophilic Substitutions. The Reaction of 4-(p-Methoxyphenylazo) Pyridinium Methiodide With Piperidine in Dimethyl Sulphoxide;" *Heterocycles*; (1987); pp. 313-317; vol. 26, No. 2.
M. H. Habibi et al., "Efficient Catalytic Oxidation of Primary Aromatic Amines to Azo Derivatives by Manganese (III) Tetraphenylporphyrin†," *J. Chem. Research (S)*. (1998), pp. 648-649, vol. 10.
X. -Y. Wang et al.; "The Preparation of Symmetrical Azobenzenes From Anilines by Phase Transfer Catalyzed Method;" *Synthetic Communications*; (1999); pp. 2271-2276; vol. 29, No. 13.

* cited by examiner

SYMMETRICAL DIAZO COMPOUNDS CONTAINING 2-PYRIDINIUM GROUPS AND CATIONIC OR NON-CATIONIC LINKER, COMPOSITIONS COMPRISING THEM, METHOD OF COLORING, AND DEVICE

This application claims benefit of U.S. Provisional Application No. 60/646,974, filed Jan. 27, 2005, the contents of which are incorporated herein by reference. This application also claims benefit of priority under 35 U.S.C. § 119 to French Patent Application No. 04 52999, filed Dec. 15, 2004, the contents of which are also incorporated herein by reference.

The present disclosure relates to symmetrical cationic diazo compounds comprising 2-pyridinium groups and a cationic or non-cationic linker, to dyeing compositions comprising such compounds as at least one direct dye, in a medium appropriate for the dyeing of keratin fibers, to a method of coloring keratin fibers that employs this composition, and to a device or kit having a plurality of compartments.

It is known practice to dye keratin fibers, including human keratin fibers such as the hair, with dyeing compositions comprising direct dyes. These compounds are colored, and coloring molecules having an affinity for the fibers. It is known practice, for example, to use direct dyes of nitrobenzene type, anthraquinone dyes, nitropyridines and dyes of azo, xanthene, acridine, azine or triarylmethane type.

Commonly these dyes are applied to the fibers, optionally in the presence of an oxidizing agent if a simultaneous fiber lightening effect is desired. When the period of leave-in time has elapsed, the fibers are rinsed, optionally washed, and dried.

The colorations which result from the use of direct dyes are temporary or semi-permanent colorations. The nature of the interactions which bind the direct dyes to the keratin fiber, and their desorption from the surface and/or the core of the fiber, are responsible for their relatively low tinctorial strength and relatively poor wash resistance or perspiration resistance.

It is known from European Patent Application No. EP 1 377 263 to employ certain direct cationic diazo dyes containing two cationic heterocyclic groups. These compounds, although representing an advance in the art, may give dyeing results which nevertheless need improvement.

For the purposes of the present disclosure, and in the absence of any indication otherwise:
an alkyl(ene) radical or the alkyl(ene) moiety of a radical is linear or branched.
an alkyl(ene) radical or the alkyl(ene) moiety of a radical is said to be substituted when it comprises at least one substituent chosen from:
hydroxyl groups,
$C_1$-$C_4$ alkoxy groups, $C_2$-$C_4$ (poly)hydroxyalkoxy groups,
amino groups, amino groups substituted by one or two identical or different $C_1$-$C_4$ alkyl groups which optionally carry at least one group chosen from hydroxyl and $C_1$-$C_2$ alkoxy groups, it being possible for said alkyl groups to form, with the nitrogen atom to which they are attached, a heterocycle containing 5 or 7 ring members which is saturated or unsaturated, is optionally aromatic, is optionally substituted and contains optionally at least one other heteroatom which is nitrogen or different from nitrogen,
alkylcarbonylamino radicals (R'CO—NR—) in which the radical R is chosen from a hydrogen atom and $C_1$-$C_4$ alkyl radicals,
alkylsulphonyl radicals (R—$SO_2$—) in which the radical R is chosen from $C_1$-$C_4$ alkyl radicals,
alkylsulphinyl radicals (R—SO—) in which the radical R is chosen from $C_1$-$C_4$ alkyl radicals,
alkylcarbonyl radicals (R—CO—) in which the radical R is chosen from $C_1$-$C_4$ alkyl radicals.

An aromatic or non-aromatic, saturated or unsaturated (hetero)cyclic radical, or the aromatic or non-aromatic, saturated or unsaturated (hetero)cyclic moiety of a radical, is said to be substituted when it comprises at least one substituent, for instance carried by a carbon atom, chosen from:
optionally substituted $C_1$-$C_{16}$, such as $C_1$-$C_8$, alkyl radicals;
halogen atoms, such as chlorine, fluorine or bromine;
hydroxyl groups;
$C_1$-$C_4$ alkoxy radicals; $C_2$-$C_4$ (poly)hydroxyalkoxy radicals;
amino radicals;
amino radicals substituted by one or two identical or different $C_1$-$C_4$ alkyl radicals which optionally carry at least one group chosen from hydroxyl, amino, $C_1$-$C_4$ (mono- or di-)alkylamino, and $C_1$-$C_2$ alkoxy groups, it being possible for the two alkyl radicals, with the nitrogen atom to which they are attached, to form a heterocycle containing 1 to 3 heteroatoms, for example 1 or 2 heteroatoms, chosen from N, O and S, such as N, the heterocycle containing 5 to 7 ring members, being saturated or unsaturated and aromatic or non-aromatic, and optionally being substituted;
alkylcarbonylamino radicals (R'CO—NR—) in which the radical R is chosen from a hydrogen atom and $C_1$-$C_4$ alkyl radicals, and the radical R' is chosen from $C_1$-$C_2$ alkyl radicals;
aminocarbonyl radicals (($R)_2$N—CO—) in which the radicals R, which may be identical or different, are chosen from hydrogen atoms and $C_1$-$C_4$ alkyl radicals;
alkylsulphonylamino radicals (R'$SO_2$—NR—) in which the radical R is chosen from a hydrogen atom and $C_1$-$C_4$ alkyl radicals, and the radical R' is chosen from $C_1$-$C_4$ alkyl radicals and phenyl radicals;
aminosulphonyl radicals (($R)_2$N—$SO_2$—) in which the radicals R, which may be identical or different, are chosen from hydrogen atoms and $C_1$-$C_4$ alkyl radicals.

The compounds according to the present disclosure are termed symmetrical when there exists a plane of symmetry perpendicular to the linker L. In other words, there is symmetry when the two formula members on either side of the linker L are identical.

Where the different groups forming part of the structure of the compounds according to the present disclosure are substituted, the skilled person will select them such that the symmetry of the molecule is respected, if symmetry is desired.

There is thus a need in the art to provide direct dyes which do not exhibit at least one of the drawbacks of existing direct dyes.

The present disclosure accordingly relates to symmetrical cationic diazo compounds of formula (I), the resonance forms thereof, and the acid addition salts and/or the solvates thereof:

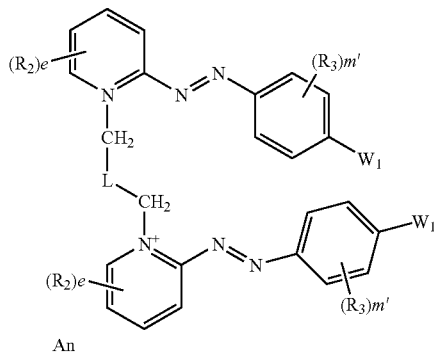

(I)

wherein:

the radicals $R_2$, which may be identical or different, are chosen from:
- optionally substituted $C_1$-$C_{16}$ alkyl radicals optionally interrupted by at least one heteroatom and/or by at least one group comprising at least one heteroatom, such as oxygen, nitrogen, sulphur, —CO—, —SO$_2$— or combinations thereof; said alkyl radicals being further optionally substituted by at least one group chosen from thio (—SH), $C_1$-$C_4$ thioalkyl, $C_1$-$C_4$ alkylsulphinyl, and $C_1$-$C_4$ alkylsulphonyl groups;
- hydroxyl groups,
- $C_1$-$C_4$ alkoxy groups,
- $C_2$-$C_4$ (poly)hydroxyalkoxy groups;
- alkoxycarbonyl groups (RO—CO—) in which R is chosen from $C_1$-$C_4$ alkyl radicals,
- alkylcarbonyloxy radicals (RCO—O—) in which R is chosen from $C_1$-$C_4$ radicals,
- alkylcarbonyl radicals (R—CO—) in which R is chosen from $C_1$-$C_4$ alkyl radicals,
- amino groups,
- amino groups substituted by one or two identical or different $C_1$-$C_4$ alkyl radicals optionally carrying at least one hydroxyl group, it being possible for the two alkyl radicals optionally to form, with the nitrogen atom to which they are attached, a heterocycle comprising 1 to 3 heteroatoms, such as 1 to 2 heteroatoms, chosen from N, O and S, for instance N, and containing 5 to 7 ring members, which is saturated or unsaturated, aromatic or non-aromatic and is optionally substituted;
- alkylcarbonylamino groups (RCO—NR'—) in which the radical R is chosen from $C_1$-$C_4$ alkyl radicals, and the radical R' is chosen from hydrogen and $C_1$-$C_4$ alkyl radicals;
- aminocarbonyl groups ((R)$_2$N—CO—) in which the radicals R, which may be identical or different, are chosen from hydrogen atoms and $C_1$-$C_4$ alkyl radicals;
- ureido groups (N(R)$_2$—CO—NR'—) in which the radicals R and R', independently of one another, are chosen from hydrogen atoms and $C_1$-$C_4$ alkyl radicals;
- aminosulphonyl groups ((R)$_2$N—SO$_2$—) in which the radicals R, independently of one another, are chosen from hydrogen atoms and $C_1$-$C_4$ alkyl radicals;
- alkylsulphonylamino groups (RSO$_2$—NR'—) in which R is chosen from $C_1$-$C_4$ alkyl radicals, and R' is chosen from a hydrogen atom and $C_1$-$C_4$ alkyl radicals;
- optionally substituted aryl radicals;
- optionally substituted ($C_1$-$C_4$ alkyl)aryl radicals;
- alkylsulphinyl groups (R—SO—) in which R is chosen from $C_1$-$C_4$ alkyl radicals;
- alkylsulphonyl groups (R—SO$_2$—) in which R is chosen from $C_1$-$C_4$ alkyl radicals;
- nitro groups;
- cyano groups;
- halogen atoms, such as chlorine or fluorine;
- thio groups (HS—);
- alkylthio groups (RS—) in which the radical R is chosen from optionally substituted $C_1$-$C_4$ alkyl radicals;
- e is an integer from 0 to 4; when e is 2, the two radicals $R_2$ may optionally form, with the carbon atoms to which they are attached, a secondary ring, aromatic or non-aromatic, containing 5 or 6 ring members, such as 6 members, which is optionally substituted by at least one group which is identical or different and is chosen from hydroxyl groups, $C_1$-$C_4$ alkyl groups, $C_1$-$C_4$ alkoxy groups, $C_2$-$C_4$ (poly)hydroxyalkoxy groups, amino groups, and amino groups substituted by one or two identical or different $C_1$-$C_4$ alkyl radicals which optionally carry at least one hydroxyl group;

when e is less than 4, the unsubstituted carbon atom(s) of the heterocycle carry a hydrogen atom, the radicals $R_3$, which may be identical or different, are chosen from:
- optionally substituted $C_1$-$C_{16}$ alkyl radicals optionally interrupted by at least one heteroatom, or by at least one group comprising at least one heteroatom, for example chosen from oxygen, nitrogen, sulphur, —CO—, —SO$_2$— and combinations thereof,
- hydroxyl groups,
- $C_1$-$C_4$ alkoxy groups,
- $C_2$-$C_4$ (poly)hydroxyalkoxy groups;
- alkoxycarbonyl groups (RO—CO—) in which R is chosen from $C_1$-$C_4$ alkyl radicals,
- alkylcarbonyloxy radicals (RCO—O—) in which R is chosen from $C_1$-$C_4$ alkyl radicals;
- alkylcarbonyl radicals (R—CO—) in which R is chosen from $C_1$-$C_4$ alkyl radicals;
- amino groups;
- amino groups substituted by one or two identical or different $C_1$-$C_4$ alkyl radicals optionally carrying at least one hydroxyl group; it being possible for the two alkyl radicals optionally to form, with the nitrogen atom to which they are attached, a heterocycle comprising 1 to 3 heteroatoms, such as 1 to 2 heteroatoms, chosen from N, O and S, for instance N, and containing 5 to 7 ring members, which is saturated or unsaturated, aromatic or non-aromatic and is optionally substituted;
- alkylcarbonylamino groups (RCO—NR'—) in which the radical R is chosen from $C_1$-$C_4$ alkyl radicals, and the radical R' is chosen from a hydrogen atom and $C_1$-$C_4$ alkyl radicals;
- aminocarbonyl groups ((R)$_2$N—CO—) in which the radicals R, independently of one another, are chosen from hydrogen atoms and $C_1$-$C_4$ alkyl radicals;
- ureido groups (N(R)$_2$—CO—NR'—) in which the radicals R and R', independently of one another, are chosen from hydrogen atoms and $C_1$-$C_4$ alkyl radicals;
- aminosulphonyl groups ((R)$_2$N—SO$_2$—) in which the radicals R, independently of one another, are chosen from hydrogen atoms and $C_1$-$C_4$ alkyl radicals;
- alkylsulphonylamino groups (RSO$_2$—NR'—) in which the radicals R and R', independently of one another, are chosen from hydrogen atoms and $C_1$-$C_4$ alkyl radicals;
- thio groups (HS—);

alkylthio groups (RS—) in which the radical R is chosen from $C_1$-$C_4$ alkyl radicals;

alkylsulphinyl groups (R—SO—) in which R is chosen from $C_1$-$C_4$ alkyl radicals;

alkylsulphonyl groups (R—$SO_2$—) in which R is chosen from $C_1$-$C_4$ alkyl radicals;

nitro groups;

cyano groups;

halogen atoms, such as chlorine or fluorine;

m' is an integer from 0 to 4; when m' is greater than or equal to 2, two adjacent radicals $R_3$ may form, with the carbon atoms to which they are attached, a secondary ring, aromatic or non-aromatic, containing 6 ring members, which is optionally substituted by at least one group which is identical or different and is chosen from: hydroxyl groups, $C_1$-$C_4$ alkyl groups, $C_1$-$C_4$ alkoxy groups, $C_2$-$C_4$ (poly)hydroxyalkoxy groups, amino groups, amino groups substituted by one or two identical or different $C_1$-$C_4$ alkyl radicals which optionally carry at least one hydroxyl group;

when m' is less than 4, the unsubstituted carbon atom(s) of the heterocycle carry a hydrogen atom;

$W_1$ radicals, which are identical, are chosen from:
hydrogen atoms,
halogen atoms chosen from bromine, chlorine and fluorine, such as chlorine and fluorine,
—$NR_5R_6$, $OR_7$, —$NR_4$—Ph—$NR_5R_6$, —$NR_4$—Ph—$OR_7$, —O—Ph—$OR_7$ and —O—Ph—$NR_5R_6$ groups;

wherein:

$R_4$ and $R_7$, which may be identical or different, are chosen from hydrogen atoms, optionally substituted $C_1$-$C_{20}$, such as $C_1$-$C_{16}$, alkyl radicals, optionally substituted $C_1$-$C_3$ aralkyl radicals, and optionally substituted phenyl radicals;

$R_5$ and $R_6$, which may be identical or different, are chosen from hydrogen atoms, optionally substituted $C_1$-$C_{20}$, such as $C_1$-$C_{16}$, alkyl radicals, optionally substituted phenyl radicals, optionally substituted $C_1$-$C_3$ aralkyl radicals, and alkylcarbonyl radicals (R—CO—) in which R is chosen from $C_1$-$C_4$ alkyl radicals;

$R_5$ and $R_6$ may optionally form, with the nitrogen atom to which they are attached, a heterocycle comprising 1 to 3 heteroatoms, such as 1 or 2 heteroatoms, chosen from N, O and S, for instance N, and containing 5 to 7 ring members, which is saturated or unsaturated, aromatic or non-aromatic and is optionally substituted;

$R_5$ and $R_6$ may optionally form, with the carbon atom of the aromatic ring adjacent to that to which —$NR_5R_6$ is attached, a 5- or 6-membered saturated heterocycle;

Ph is chosen from optionally substituted phenyl radicals;

L is a cationic or non-cationic linker;

wherein the electroneutrality of the compound of formula (I) is ensured by at least one identical or non-identical, cosmetically acceptable anion (An).

The present disclosure also relates to dyeing compositions comprising such compounds, or the addition salts thereof with an acid, as direct dyes in a medium appropriate for the dyeing of keratin fibers.

The present disclosure further relates to a method of coloring keratin fibers comprising contacting said fibers with a composition according to the present disclosure, wherein said fibers can be dry or wet, for a time sufficient to give a desired effect, e.g., a desired color.

Finally, the present disclosure also relates to a device or kit having a plurality of compartments (multi-compartment device) and containing in a first compartment the composition according to the present disclosure and in a second compartment an oxidizing composition.

The present inventors have found, surprisingly, that the compounds of formula (I) as defined above exhibit effective resistance to external agents such as, for example, shampoos, and do so even when the keratin fiber is sensitized. Furthermore, these compounds may exhibit improved dyeing properties, such as the chromaticity, the coloring power, and/or a low selectivity, which is to say that the compounds of the present disclosure allow colorations to be obtained which are more uniform between the end and the root of the hair.

Other characteristics and benefits of the present disclosure, however, will appear more clearly from reading the description and the non-limiting examples herein below.

As used herein, in the absence of any indication otherwise, the end-points delimiting a range of values are included in that range.

As indicated above, the present disclosure relates to compounds corresponding to the aforementioned formula (I).

In one embodiment, the compounds of formula (I) according to the present disclosure are such that the radicals $R_2$, which may be identical or different, are chosen from:

halogen atoms chosen from chlorine and fluorine;

$C_1$-$C_4$ alkyl radicals optionally substituted by at least one radical chosen from hydroxyl, $C_1$-$C_2$ alkoxy, $C_2$-$C_4$ (poly)hydroxyalkoxy, amino, $C_1$-$C_2$ (di)alkylamino, thio (—SH), $C_1$-$C_4$ alkylsulphinyl, $C_1$-$C_4$ alkylsulphonyl and $C_1$-$C_4$ thioalkyl radicals;

phenyl radicals optionally substituted by at least one radical chosen from hydroxyl, $C_1$-$C_2$ alkoxy, $C_2$-$C_4$ (poly)hydroxyalkoxy, amino and $C_1$-$C_2$ (di)alkylamino radicals, and halogen atoms such as chlorine or fluorine;

$C_1$-$C_4$ alkoxy radicals;

$C_1$-$C_4$ alkylsulphonylamino radicals;

$C_2$-$C_4$ (poly)hydroxyalkoxy radicals;

amino radicals;

$C_1$-$C_2$ (di)alkylamino radicals;

$C_2$-$C_4$ (poly)hydroxyalkylamino radicals;

alkylsulphonylamino radicals ($RSO_2N$—) in which the radical R is chosen from $C_1$-$C_4$ alkyl radicals;

aminosulphonyl radicals (($R)_2NSO_2$—) in which the radicals R, independently of one another, are chosen from hydrogen atoms and $C_1$-$C_4$ alkyl radicals;

alkylthio radicals (RS—) in which the radical R is chosen from $C_1$-$C_4$ alkyl radicals;

alkylsulphinyl radicals (RSO—) in which the radical R is chosen from $C_1$-$C_4$ alkyl radicals;

alkylsulphonyl radicals (R—$SO_2$—) in which the radical R is chosen from $C_1$-$C_4$ alkyl radicals;

alkylcarbonylamino radicals (RCONR'—) in which the radical R is chosen from a hydrogen atom and $C_1$-$C_4$ alkyl radicals, and the radical R' is chosen from a hydrogen atom, and $C_1$-$C_4$ alkyl radicals.

According to another embodiment, the radicals $R_2$ can be chosen from, for example, methyl, ethyl, 2-hydroxyethyl, 2-methoxyethyl, methylsulphonyl ($CH_3SO_2$—), methylcarbonylamino ($CH_3CONH$—), hydroxyl, amino, methylamino, dimethylamino, 2-hydroxyethylamino, methoxy, ethoxy, and phenyl radicals.

According to still another embodiment, the two radicals $R_2$ may optionally form, with the carbon atoms to which they are attached, a secondary, 6-membered aromatic ring optionally substituted by at least one group chosen from hydroxyl groups, $C_1$-$C_4$ alkyl groups, $C_1$-$C_4$ alkoxy groups, amino groups, and amino groups substituted by one or two identical or different $C_1$-$C_4$ alkyl radicals which optionally carry at least one hydroxyl or methylcarbonylamino group. In accordance with this embodiment, the two radicals $R_2$ may optionally form, with the carbon atoms to which they are attached, a secondary, 6-membered aromatic ring optionally substituted by at least one groups chosen from hydroxyl, methoxy, ethoxy, amino, 2-hydroxyethylamino, dimethylamino and (di)-2-hydroxyethylamino groups.

According to yet another embodiment of the present disclosure, the coefficient e is 0.

In still another embodiment, with regard to the radicals $R_3$, which may be identical or different, can be chosen from:
  optionally substituted $C_1$-$C_{16}$, such as $C_1$-$C_8$, alkyl radicals;
  halogen atoms such as chlorine or fluorine;
  hydroxyl groups;
  $C_1$-$C_2$ alkoxy radicals;
  $C_2$-$C_4$ (poly)hydroxyalkoxy radicals;
  amino radicals;
  amino radicals substituted by one or two identical or different $C_1$-$C_4$ alkyl radicals which are optionally substituted by at least one group chosen from hydroxyl and $C_1$-$C_4$ alkoxy groups, it being possible for the two alkyl radicals to form, with the nitrogen to which they are attached, a heterocycle comprising 1 to 3 heteroatoms, such as 1 or 2 heteroatoms, chosen from N, O and S, for instance N, the heterocycle containing 5 to 7 ring members, being saturated or unsaturated, aromatic or non-aromatic, and being optionally substituted;
  alkylcarbonylamino radicals (RCO—NR'—) in which the radical R is chosen from $C_1$-$C_4$ alkyl radicals, and the radical R' is chosen from a hydrogen atom and $C_1$-$C_4$ radicals;
  alkylsulphonylamino radicals (R'SO$_2$—NR—) in which the radical R is chosen from a hydrogen atom and $C_1$-$C_4$ alkyl radicals, and the radical R' is chosen from $C_1$-$C_4$ alkyl radicals;
  aminosulphonyl radicals ((R)$_2$N—SO$_2$—) in which the radicals R, which may be identical or different, are chosen from hydrogen atoms and $C_1$-$C_4$ alkyl radicals;
  alkylthio radicals (RS—) in which the radical R is chosen from $C_1$-$C_4$ alkyl radicals; and
  alkylsulphonyl radicals (R—SO$_2$—) in which the radical R is chosen from $C_1$-$C_4$ alkyl radicals.

In at least one embodiment, said radicals $R_3$, which may be identical or different, can be chosen from:
  $C_1$-$C_4$ alkyl radicals optionally substituted by at least one identical or different radical chosen from hydroxyl radicals, $C_1$-$C_2$ alkylcarbonylamino radicals, amino radicals substituted by one or two identical or different $C_1$-$C_2$ alkyl radicals which optionally carry at least one group chosen from hydroxyl groups and $C_1$-$C_2$ alkoxy radicals, it being possible for these two alkyl radicals optionally to form, with the nitrogen atom to which they are attached, a 5- or 6-membered heterocycle which is saturated or unsaturated and is optionally aromatic, chosen, for example, from pyrrolidine, piperazine, homopiperazine, pyrrole, imidazole andpyrazole;
  $C_2$-$C_4$ hydroxyalkoxy radicals;
  halogens chosen from chlorine and fluorine;
  amino radicals;
  amino radicals substituted by one or two identical or different $C_1$-$C_2$ alkyl radicals which optionally carry at least one hydroxyl group;
  methylcarbonylamino radicals;
  methylsulphonylamino radicals;
  hydroxyl radicals;
  $C_1$-$C_2$ alkoxy radicals; and
  methylsulphonyl radicals.

According to this embodiment, the radicals $R_3$, independently of one another, can further be chosen from:
  methyl, ethyl, propyl, 2-hydroxyethyl, methoxy, ethoxy, 2-hydroxyethyloxy, 3-hydroxypropyloxy and 2-methoxyethyl radicals;
  methylsulphonylamino radicals;
  amino, methylamino, dimethylamino and 2-hydroxyethylamino radicals;
  methylcarbonylamino radicals;
  hydroxyl radicals;
  chlorine atoms; and
  methylsulphonyl radicals.

According to yet another embodiment of the present disclosure, when the coefficient m' is greater than or equal to 2, two adjacent radicals $R_3$ may form, with the carbon atoms to which they are attached, a secondary, 6-membered aromatic ring optionally substituted by at least one group chosen from hydroxyl groups, —NR$_4$—Ph groups, —NR$_4$—Ph—NR$_5$R$_6$ groups, —NR$_4$—Ph—OR$_7$ groups, $C_1$-$C_4$ alkyl groups, $C_1$-$C_4$ alkoxy groups, $C_2$-$C_4$ (poly)hydroxyalkoxy groups, $C_1$-$C_4$ alkylcarbonylamino groups, amino groups, and amino groups substituted by one or two identical or different $C_1$-$C_4$ alkyl radicals which optionally carry at least one hydroxyl group. According to this embodiment, for example, two adjacent radicals $R_3$ may form, with the carbon atoms to which they are attached, a secondary, 6-membered aromatic ring which is optionally substituted by at least one group chosen from hydroxyl, methoxy, ethoxy, 2-hydroxyethyloxy, amino, methylcarbonylamino, (di)-2-hydroxyethylamino, —NH—Ph, —NH—Ph—NH$_2$, —NH—Ph—NHCOCH$_3$, —NH—Ph—OH and —NH—Ph—OCH$_3$ groups.

With regard to the radicals $R_4$ and $R_7$, in one embodiment of the present disclosure, these radicals can be chosen from:
  hydrogen atoms;
  $C_1$-$C_6$ alkyl radicals which are optionally substituted, such as by at least one group chosen from hydroxyl and $C_1$-$C_2$ alkoxy groups;
  aryl and arylalkyl radicals, such as phenyl or benzyl, the aryl moiety being optionally substituted, for instance by at least one identical or different radical chosen from chlorine radicals, amino radicals, hydroxyl radicals, $C_1$-$C_2$ alkoxy radicals, amino radicals which are mono- or disubstituted by one or two identical or different $C_1$-$C_4$ alkyl radicals which optionally carry at least one hydroxyl group.

In accordance with another embodiment of the present disclosure, the radicals $R_4$ and $R_7$ can be chosen from:
  hydrogen atoms;
  optionally substituted $C_1$-$C_3$ alkyl radicals, such as methyl, ethyl, 2-hydroxyethyl or 2-methoxyethyl;
  phenyl radicals which are optionally substituted by at least one identical or different radical chosen from hydroxyl radicals, $C_1$-$C_2$ alkoxy radicals, amino radicals, and amino radicals substituted by at least one $C_1$-$C_4$ group which optionally carry at least one hydroxyl group;

for still further example, the radicals $R_4$ and $R_7$ can be chosen from:
- hydrogen atoms;
- methyl, ethyl and 2-hydroxyethyl radicals;
- phenyl radicals which are optionally substituted by a hydroxyl, methoxy, amino, (di)methylamino or (di)(2-hydroxyethyl)amino radical.

In one embodiment, with regard to the radicals $R_5$ and $R_6$, independently of one another, these radicals can be chosen from:
- hydrogen atoms;
- alkylcarbonyl radicals (R—CO—) in which R is chosen from optionally substituted $C_1$-$C_4$ alkyl radicals,
- $C_1$-$C_6$ alkyl radicals which are optionally substituted, for instance by at least one group chosen from hydroxyl groups, $C_1$-$C_2$ alkoxy groups, amino groups, $C_1$-$C_4$ (di)alkylamino groups; the alkyl radicals may further be substituted by at least one identical or different group chosen from $C_1$-$C_4$ alkylsulphonyl, $C_1$-$C_4$ alkylsulphinyl and $C_1$-$C_4$ alkylcarbonyl groups,
- aryl and arylalkyl radicals, such as phenyl or benzyl, the aryl moiety being optionally substituted by at least one radical chosen from chlorine radicals, amino radicals, hydroxyl radicals, $C_1$-$C_4$ alkoxy radicals, and amino radicals which are mono- or disubstituted by one or two identical or different $C_1$-$C_4$ alkyl radicals which optionally carry at least one hydroxyl group.

In accordance with at least one embodiment of the present disclosure, the radicals $R_5$ and $R_6$, which may be identical or different, can be, for instance, chosen from:
- hydrogen atoms;
- methylcarbonyl, ethylcarbonyl and propylcarbonyl radicals;
- optionally substituted $C_1$-$C_3$ alkyl radicals, such as methyl, ethyl, 2-hydroxyethyl or 2-methoxyethyl; and
- phenyl radicals which are optionally substituted by at least one identical or different radical chosen from hydroxyl radicals, $C_1$-$C_2$ alkoxy radicals, amino radicals, and amino radicals substituted by at least one $C_1$-$C_4$ alkyl groups which optionally carry at least one hydroxyl group.

For further example, the radicals $R_5$ and $R_6$, which may be identical or different, can be chosen from:
- hydrogen atoms;
- methyl, ethyl and 2-hydroxyethyl radicals;
- methylcarbonyl, ethylcarbonyl and propylcarbonyl radicals;
- phenyl radicals which are optionally substituted by a hydroxyl, methoxy, amino, (di)methylamino or (di)(2-hydroxyethyl)amino radical.

It should be noted that, according to at least one embodiment of the present disclosure, the radicals $R_5$ and $R_6$ form, together with the nitrogen atom to which each is attached, a heterocycle comprising 1 to 3 heteroatoms, such as 1 or 2 heteroatoms, chosen from N, O and S, for instance N, and containing 5 to 7 ring members, which is saturated or unsaturated, aromatic or non-aromatic, and is optionally substituted.

For example, in one embodiment, the heterocycle containing 5 to 7 ring members can be chosen from the following heterocycles: piperidine, 2-(2-hydroxyethylpiperidine), 4-(aminomethyl)piperidine, 4-(2-hydroxyethyl)piperidine, 4-(dimethylamino)piperidine, piperazine, 1-methylpiperazine, 1-(2-hydroxyethyl)piperazine, 1-(2-aminoethyl)piperazine, 1-hydroxyethylethoxypiperazine, homopiperazine, 1-methyl-1,4-perhydrodiazepine, pyrrole, 1,4-dimethylpyrrole, 1-methyl-4-ethylpyrrole, 1-methyl-4-propylpyrrole.

For further example, the heterocycle containing 5 to 7 ring members can be chosen from a heterocycle of piperidine, piperazine, homopiperazine, pyrrole, imidazole or pyrazole type which is optionally substituted by at least one methyl, hydroxyl, amino and/or (di)methylamino radicals.

According to still another embodiment, the radicals $R_5$ and $R_6$ can be chosen from alkyl radicals which, independently of one another, form, with the carbon atom of the aromatic ring optionally substituted by a hydroxyl and adjacent to that to which —$NR_5R_6$ is attached, a 5- or 6-membered saturated heterocycle.

For example, the group —$NR_5R_6$ with the aromatic nucleus optionally substituted by a hydroxyl group may correspond to any of the following compounds:

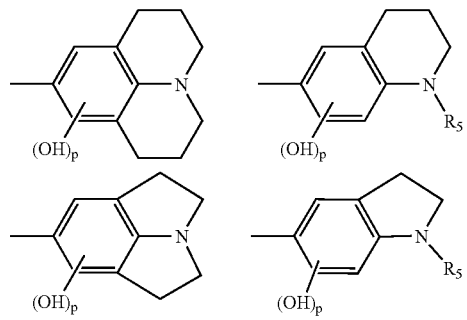

where p = 0 or 1

As discussed above, L can be a non-cationic linker.

According to this version of L, the non-cationic linker L connecting the two different azo chromophores can be chosen from:
- a covalent bond;
- optionally substituted $C_1$-$C_{40}$, such as $C_1$-$C_{20}$, alkyl radicals optionally interrupted by a saturated or unsaturated, aromatic or non-aromatic (hetero)cycle containing 3 to 7 ring members which is optionally substituted and optionally fused, said alkyl radical being optionally interrupted by at least one entity chosen from heteroatoms and groups containing at least one heteroatom, such as oxygen, nitrogen, sulphur, —CO—, —$SO_2$— or combinations thereof, with the proviso that the linker L does not contain an azo, nitro, nitroso or peroxo bond; and
- optionally substituted phenyl radicals.

Also as discussed above, the linker L can alternatively be cationic.

According to this version of L, the cationic linker L connecting the two different azo chromophores can be chosen from:
- $C_2$-$C_{40}$ alkyl radicals which carry at least one cationic charge and is optionally substituted and/or optionally interrupted by at least one saturated or unsaturated, aromatic or non-aromatic, identical or different (hetero) cycles containing 3 to 7 ring members and/or optionally interrupted by at least one entity chosen from heteroatoms and groups containing at least one heteroatom, or combinations thereof, such as, for example, oxygen, nitrogen, sulphur, a group —CO— or —$SO_2$— or combinations thereof, with the proviso that the linker L does not contain azo, nitro, nitroso or peroxo bonds; and wherein the linker L carries at least one cationic charge.

According to one embodiment of the present disclosure, L is a non-cationic linker.

According to this embodiment, for example, L can be chosen from methylene, ethylene, linear and branched propylene, linear and branched butylene, linear and branched pentylene, and linear and branched hexylene radicals which are optionally substituted and/or interrupted as indicated above.

These identical or different substituents can be chosen from, for instance, hydroxyl, $C_1$-$C_2$ alkoxy, $C_1$-$C_2$ dialkylamino, ($C_1$-$C_4$ alkyl)carbonyl and $C_1$-$C_4$ alkyl sulphonyl.

Further examples of an aromatic or non-aromatic, saturated or unsaturated cycle or heterocycle that may interrupt the alkyl radical of the linker L include phenylene, naphthylene, phenanthrylene, triazinyl, pyrimidinyl, pyridinyl, pyridazinyl, quinoxalinyl and cyclohexyl radicals.

Still further examples of linkers L include methylene, ethylene, linear or branched propylene, linear or branched butylene, linear or branched pentylene and linear or branched hexylene radicals optionally substituted and/or interrupted as indicated above.

Examples of an aromatic or non-aromatic, saturated or unsaturated cycle or heterocycle that may interrupt the alkyl radical of the linker L include phenylene or naphthylene, phenanthrylene, triazinyl, pyrimidinyl, pyridinyl, pyridazinyl, quinoxalinyl and cyclohexyl radicals.

For instance, the following radicals L are suitable:

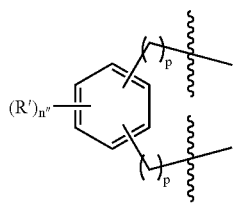

p is 0 or 1
n″ is an integer between 0 and 4

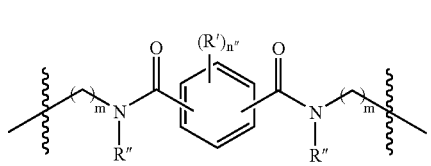

—($C_nH_{2n}$)—  ——($C_nH_{2n})_2$—X
0 < n < 19      0 < n < 10
              X = NH, $NR_4$, O S, SO, $SO_2$

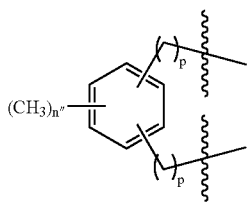

m is an integer between 0 and 6
n″ is an integer between 0 and 4

-continued

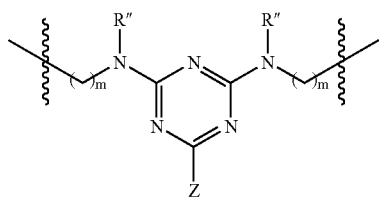

m is an integer between 0 and 6
Z = OH, $NR_8R_9$

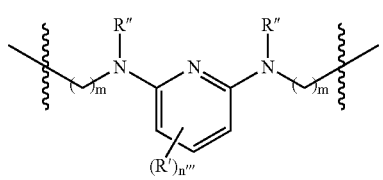

m is an integer between 0 and 6
n‴ is an integer between 0 and 3

In these formulae above:

R' has the same definition as $R_3$;

R″ radicals, which are identical, are chosen from hydrogen atoms and $C_1$-$C_4$ alkyl radicals;

$R_8$ and $R_9$, independently of one another, are chosen from hydrogen atoms and $C_1$-$C_8$ alkyl radicals which are optionally substituted by at least one identical or different radical chosen from hydroxyl, $C_1$-$C_2$ alkoxy, $C_2$-$C_4$ (poly)hydroxyalkoxy, amino, $C_1$-$C_2$ (di)alkylamino and optionally substituted aryl radicals.

Further examples of possible radicals L include:

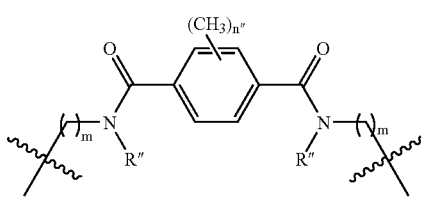

p is 0 or 1
n″ is an integer between 0 and 4

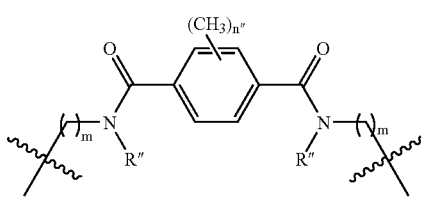

m is an integer between 0 and 6
n″ is an integer between 0 and 4
The aromatic ring positions not substituted by a methyl radical carry a hydrogen atom According to another embodiment, L is a cationic linker. According to this embodiment, the cationic linker L can be chosen from $C_2$-$C_{20}$ alkyl radicals:

1) interrupted by at least one group corresponding to the following formulae:

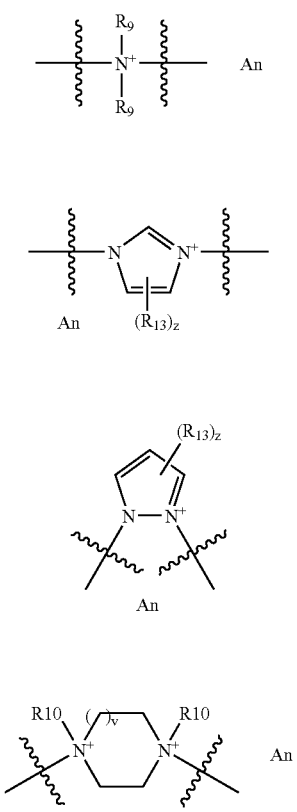

in which:
- $R_9$ and $R_{10}$, independently of one another, are chosen from $C_1$-$C_8$ alkyl radicals; $C_1$-$C_6$ monohydroxyalkyl radicals; $C_2$-$C_6$ polyhydroxyalkyl radicals; $C_1$-$C_6$ alkoxy-$C_1$-$C_6$ alkyl radicals; aryl radicals such as phenyl which is optionally substituted; arylalkyl radicals such as benzyl which is optionally substituted; $C_1$-$C_6$ aminoalkyl radicals; $C_1$-$C_6$ aminoalkyl radicals whose amine is substituted by one or two identical or different $C_1$-$C_4$ alkyl radicals; and $C_1$-$C_6$ alkylsulphonyl radicals,
- two radicals $R_9$ may together form, with the nitrogen atom to which they are attached, a saturated or unsaturated ring which is optionally substituted and has 5, 6 or 7 ring members,
- $R_{13}$ radicals, which may be identical or different, are chosen from halogen atoms chosen from bromine, chlorine and fluorine, $C_1$-$C_6$ alkyl radicals, $C_1$-$C_6$ monohydroxyalkyl radicals, $C_2$-$C_6$ polyhydroxyalkyl radicals, $C_1$-$C_6$ alkoxy radicals, $C_1$-$C_4$ (di)alkylamino radicals, hydroxycarbonyl radicals, $C_1$-$C_6$ alkylcarbonyl radicals, $C_1$-$C_6$ thioalkyl radicals, $C_1$-$C_6$ alkylthio radicals, $C_1$-$C_6$ alkylsulphonyl radicals, optionally substituted benzyl radicals, and phenyl radicals which are optionally substituted by at least one radical chosen from methyl, hydroxyl, amino and methoxy radicals,
- An is chosen from organic and inorganic anions, or an anion mixture thereof,
- z is an integer ranging from 1 to 3; if z is less than 3, then the unsubstituted carbon atoms carry a hydrogen atom;
- v is an integer chosen from 1 or 2, such as 1, 2) optionally interrupted by at least one entity chosen from heteroatoms and groups comprising at least one heteroatom, such as, for example, oxygen, nitrogen, sulphur, a —CO— group or a —SO$_2$— group, with the proviso that there is no nitro, nitroso or peroxo bond or group in the linker L; and 3) optionally substituted by at least one radical chosen from hydroxyl radicals, $C_1$-$C_2$ alkoxy radicals, $C_2$-$C_4$ (poly)hydroxyalkoxy radicals, amino radicals substituted by at least one group chosen from linear and branched $C_1$-$C_2$ alkyl groups which optionally carry at least one hydroxyl group.

According to one embodiment of formulae (a) and (d), $R_9$ and $R_{10}$, independently of each other, can be chosen from $C_1$-$C_6$ alkyl radicals, $C_1$-$C_4$ monohydroxyalkyl radicals, $C_2$-$C_4$ polyhydroxyalkyl radicals, $C_1$-$C_6$ alkoxy-$C_2$-$C_4$ alkyl radicals, and $C_2$-$C_6$ dimethylaminoalkyl radicals.

For further example, $R_9$ and $R_{10}$, independently of one another, can be chosen from methyl, ethyl and 2-hydroxyethyl radicals.

According to one embodiment of formulae (b) and (c), $R_{13}$ can be chosen from halogen atoms chosen from chlorine and fluorine, $C_1$-$C_8$ alkyl radicals, $C_1$-$C_4$ monohydroxyalkyl radicals, $C_1$-$C_4$ alkoxy radicals, hydroxycarbonyl radicals, $C_1$-$C_6$ alkylthio radicals, and amino radicals disubstituted by $C_1$-$C_4$ alkyl radicals.

According to another embodiment of formulae (b) and (c), $R_{13}$ can be chosen from a chlorine atom, and methyl, ethyl, 2-hydroxyethyl, methoxy, hydroxycarbonyl and dimethylamino radicals.

According to still another embodiment of formulae (b) and (c), z is 0.

In the formula (I) An is chosen from organic and inorganic anions or an anion mixture allowing the charge or charges on the compounds of formula (I) to be balanced, and chosen for example from halides such as chloride, bromide, fluoride or iodide; hydroxides; sulphates; hydrogensulphates; alkylsulphates for which the linear or branched alkyl moiety is $C_1$-$C_6$, such as the methylsulphate or ethylsulphate ion; carbonates and hydrogencarbonates; salts of carboxylic acids, such as formate, acetate, citrate, tartrate and oxalate; alkylsulphonates for which the linear or branched alkyl moiety is $C_1$-$C_6$, such as the methylsulphonate ion; arylsulphonates for which the aryl moiety, such as phenyl, is optionally substituted by at least one $C_1$-$C_4$ radical, such as 4-tolylsulphonate, for example; and alkylsulphonyls such as mesylate.

The acid addition salts of the compounds of formula (I) may be, by way of non-limiting example, the addition salts with an organic or inorganic acid such as hydrochloric acid, hydrobromic acid, sulphuric acid or (alkyl- or phenyl-)sulphonic acids such as p-toluenesulphonic acid or methylsulphonic acid.

The solvates of compounds of formula (I) are chosen from the hydrates of such compounds, or the combination of compounds of formula (I) with a linear or branched $C_1$-$C_4$ alcohol such as methanol, ethanol, isopropanol or n-propanol.

In accordance with one embodiment of the present disclosure, the compounds can be chosen from those of formulae (I'), (I") or (III'") below, and also to the resonance forms and/or acid addition salts and/or its solvates thereof:

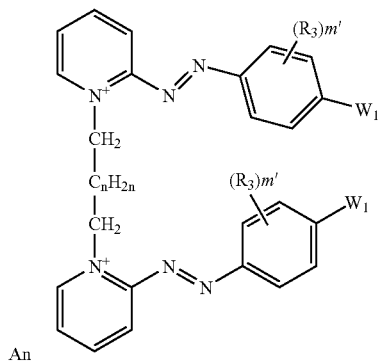

(I')

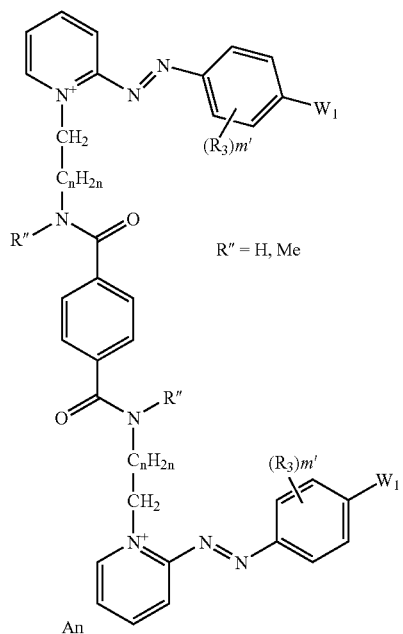

(I")

n = integer between 1 and 6

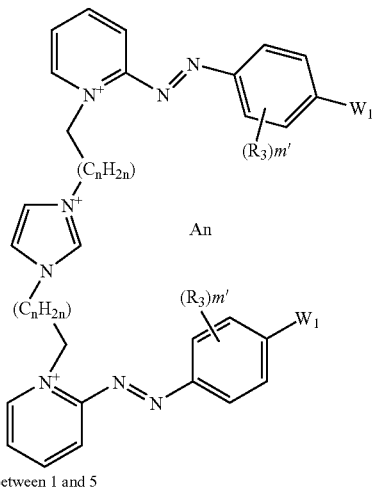

(I'")

n = integer between 1 and 5

In accordance with another embodiment of the present disclosure, the compounds can be chosen from those of the formulae below, and also to the resonance forms, the acid addition salts and/or the solvates thereof:

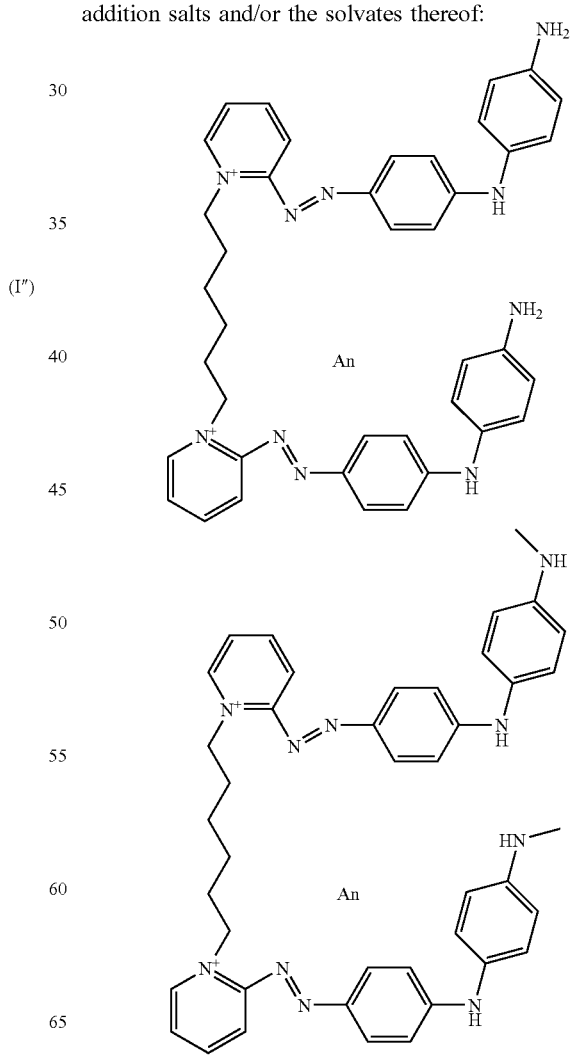

-continued
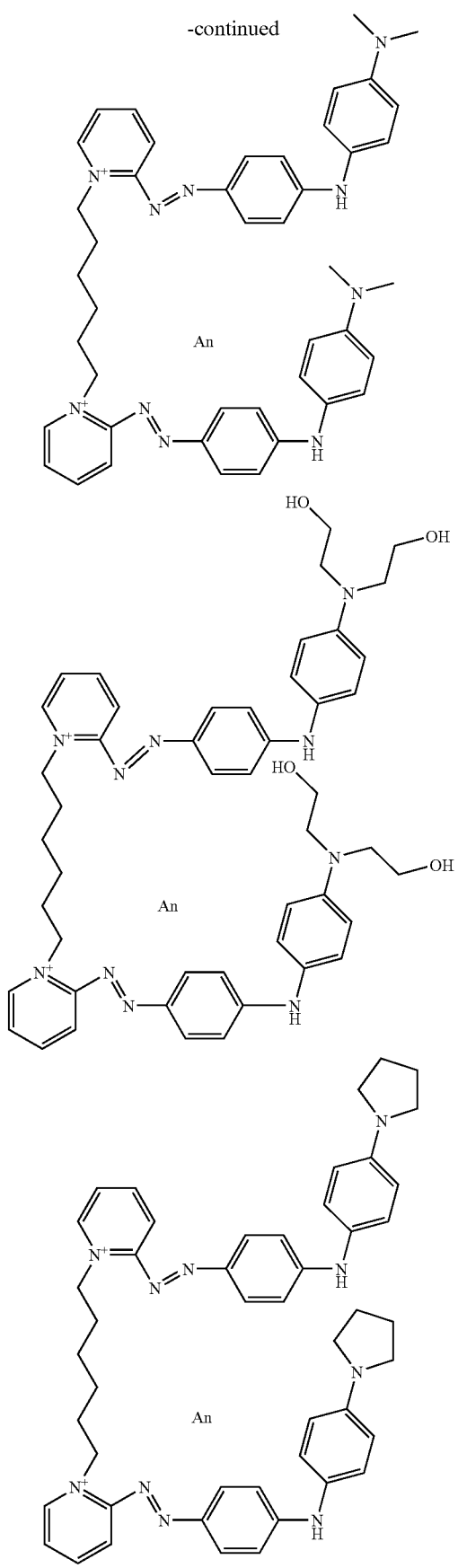
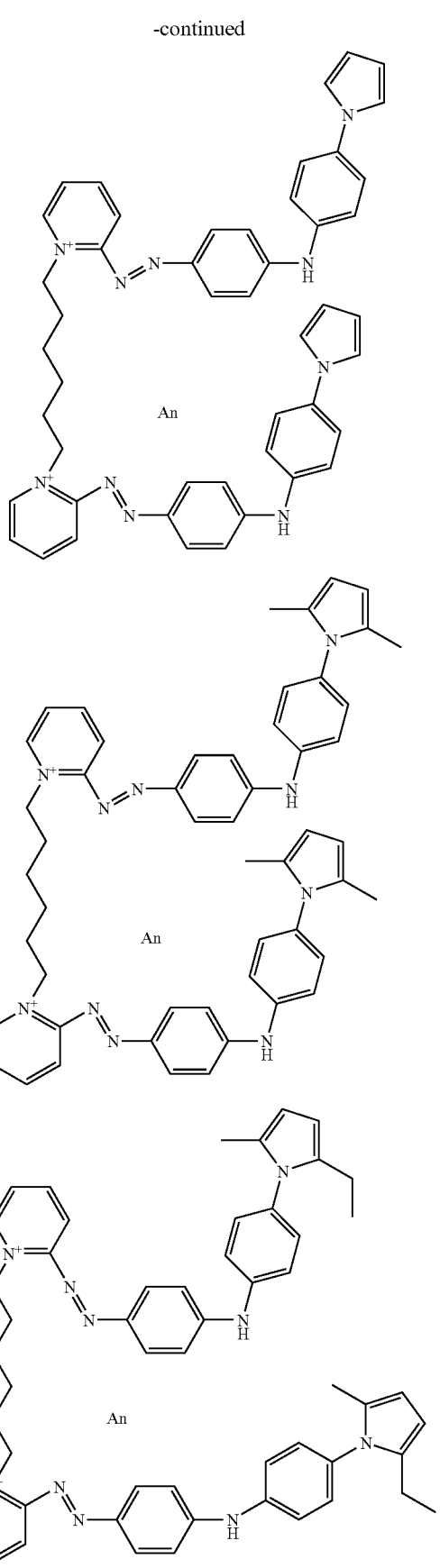

-continued
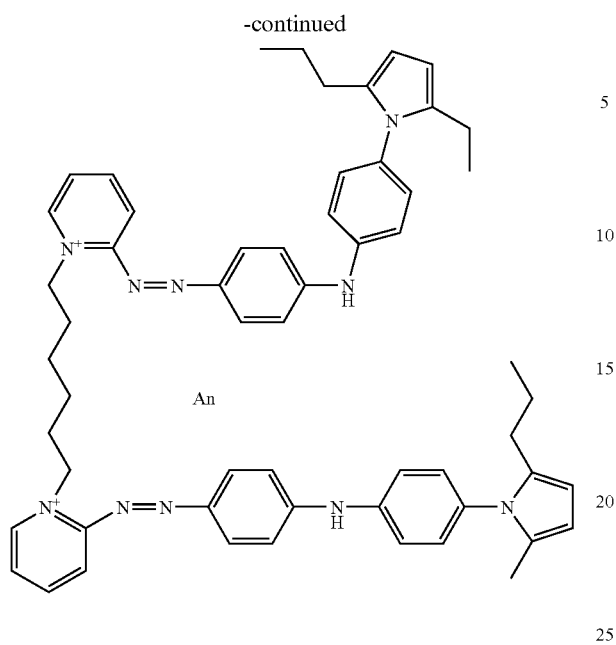
An
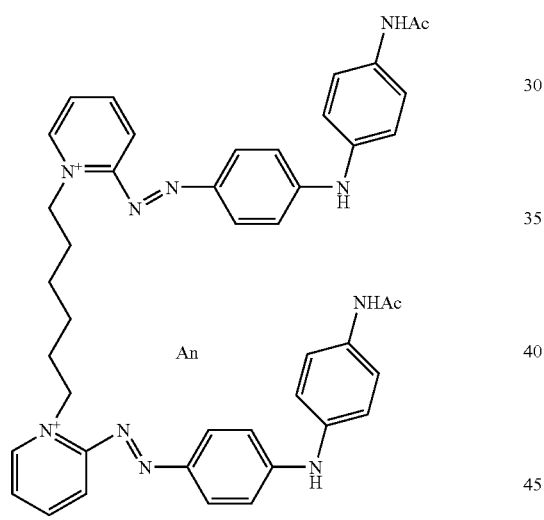
An
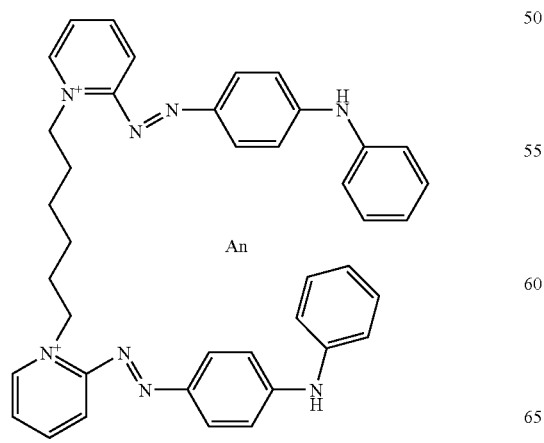
An
-continued
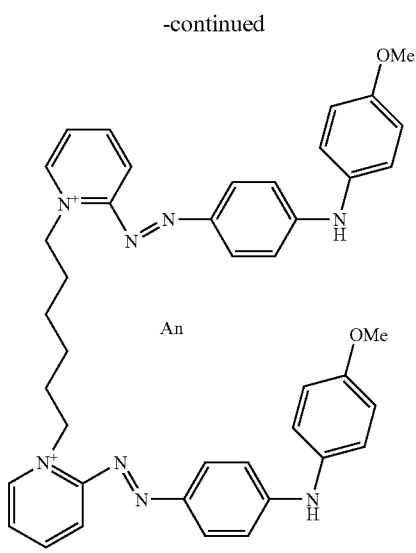
An
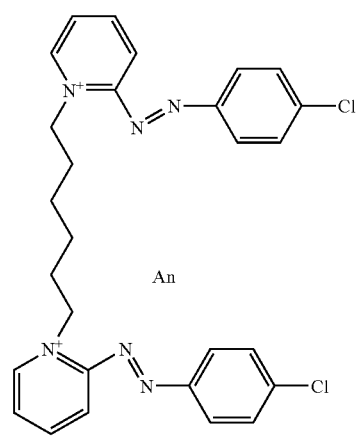
An
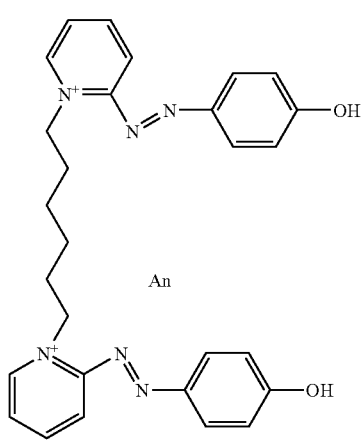
An -continued
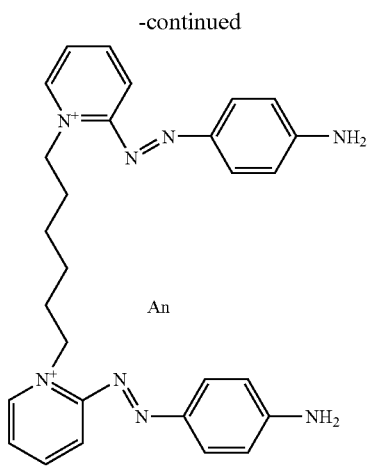
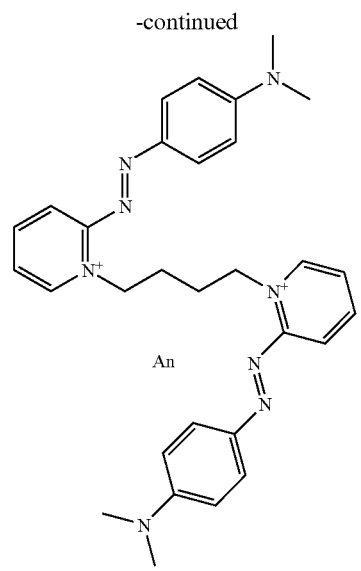
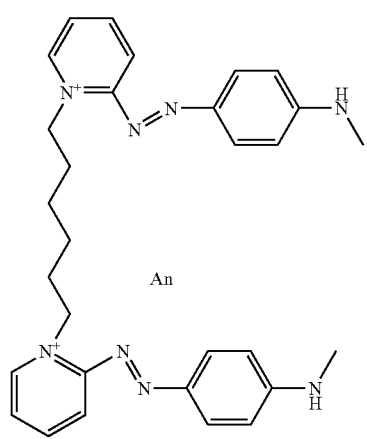
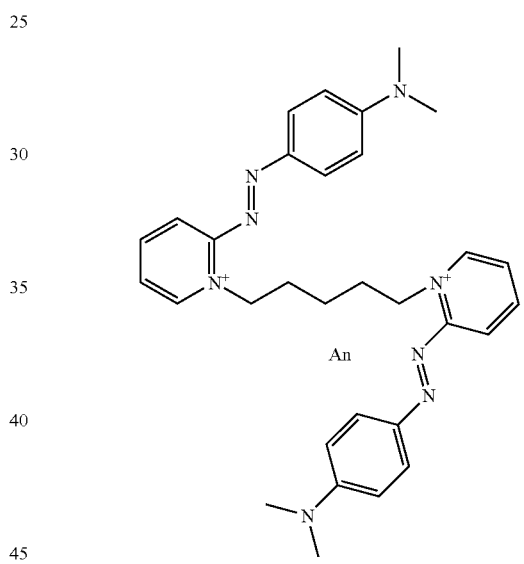
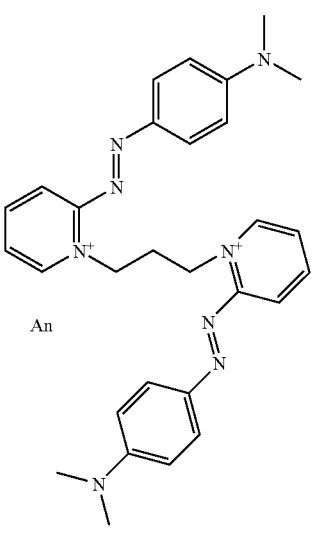
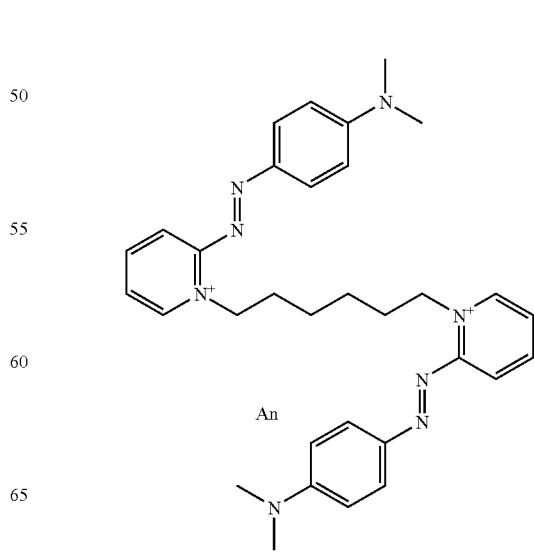

-continued
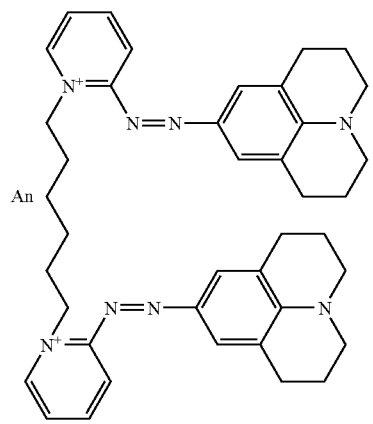
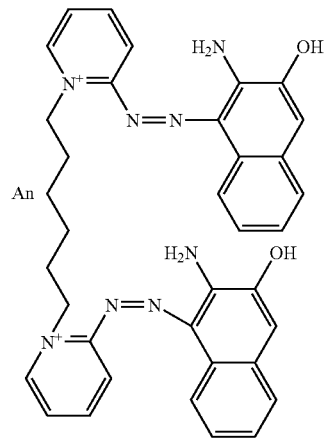
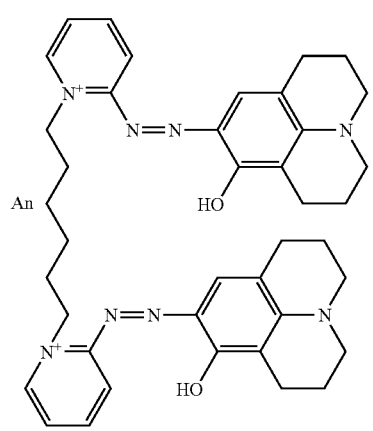
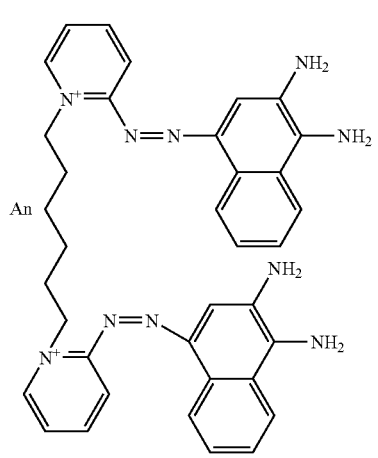
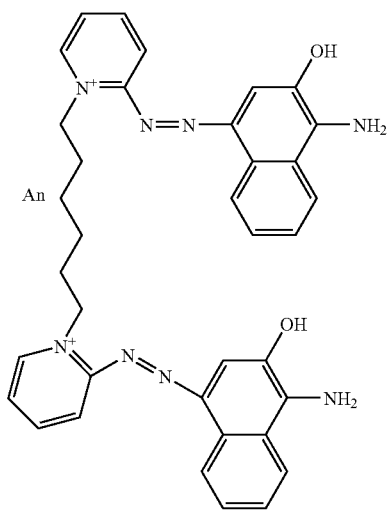
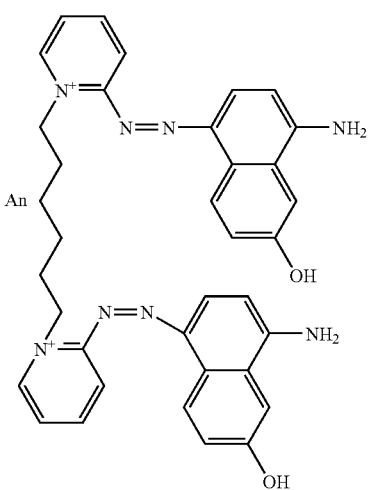

-continued
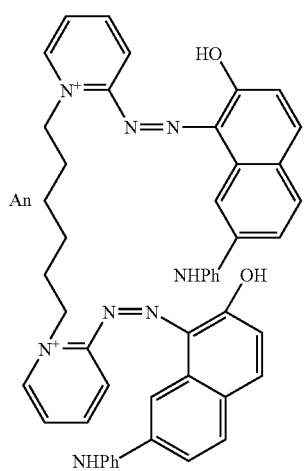
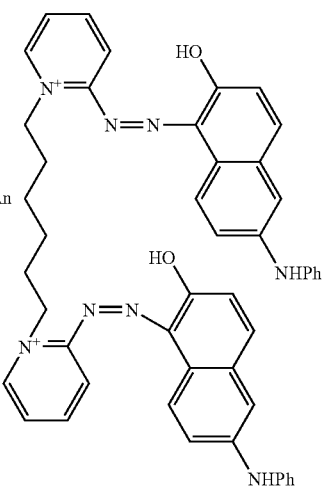
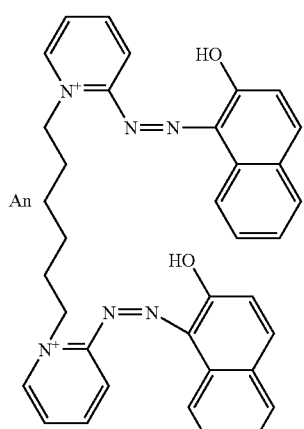
-continued
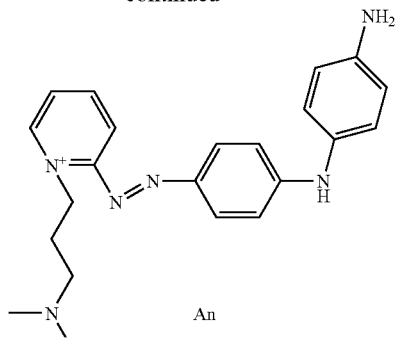
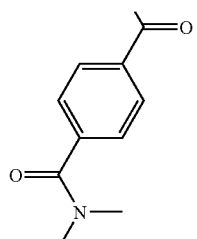
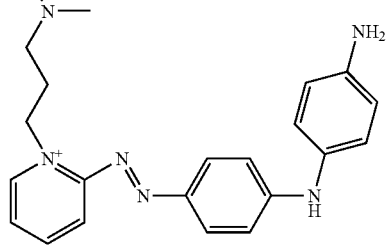
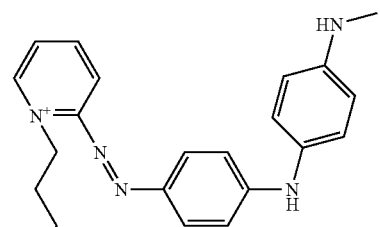
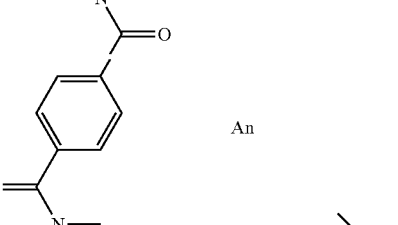
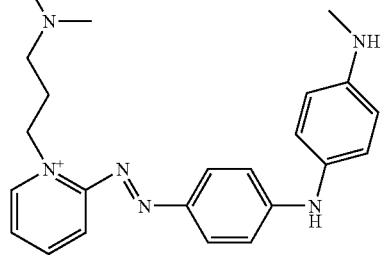

-continued
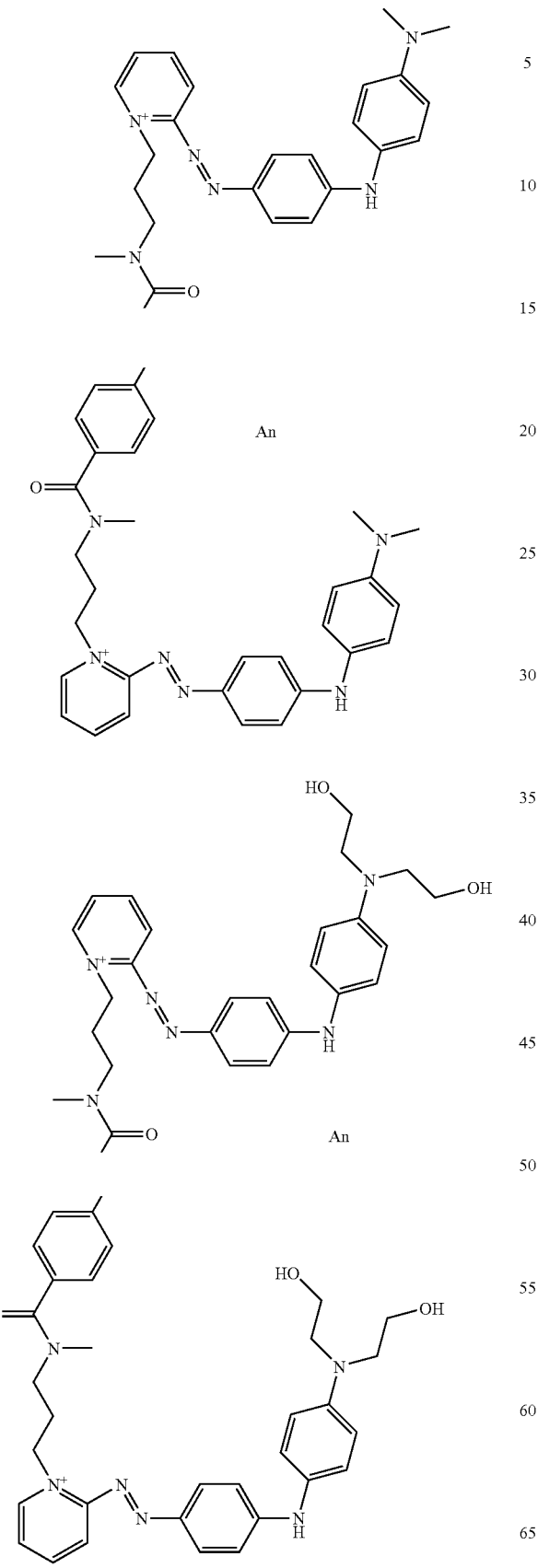
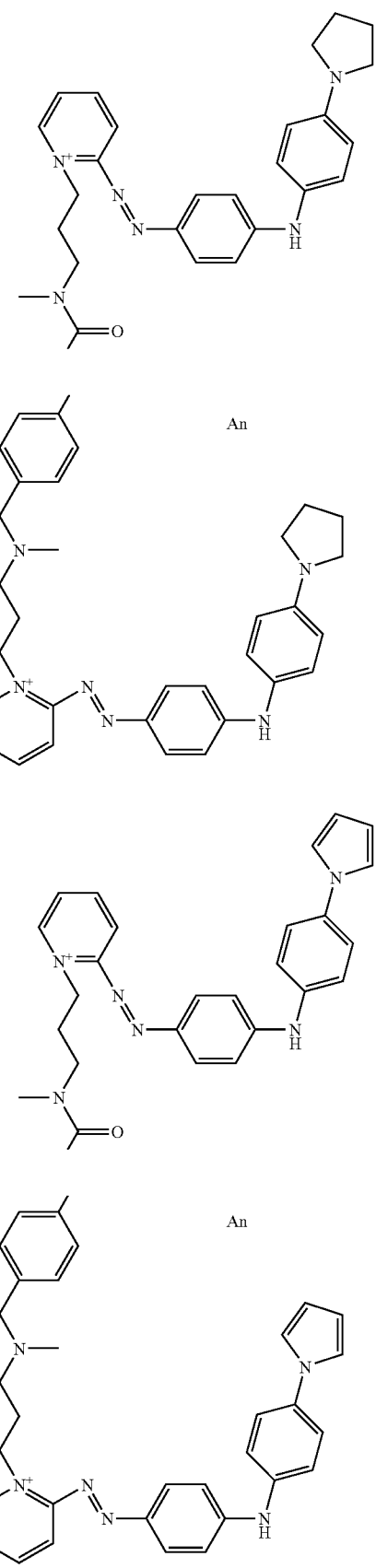

-continued
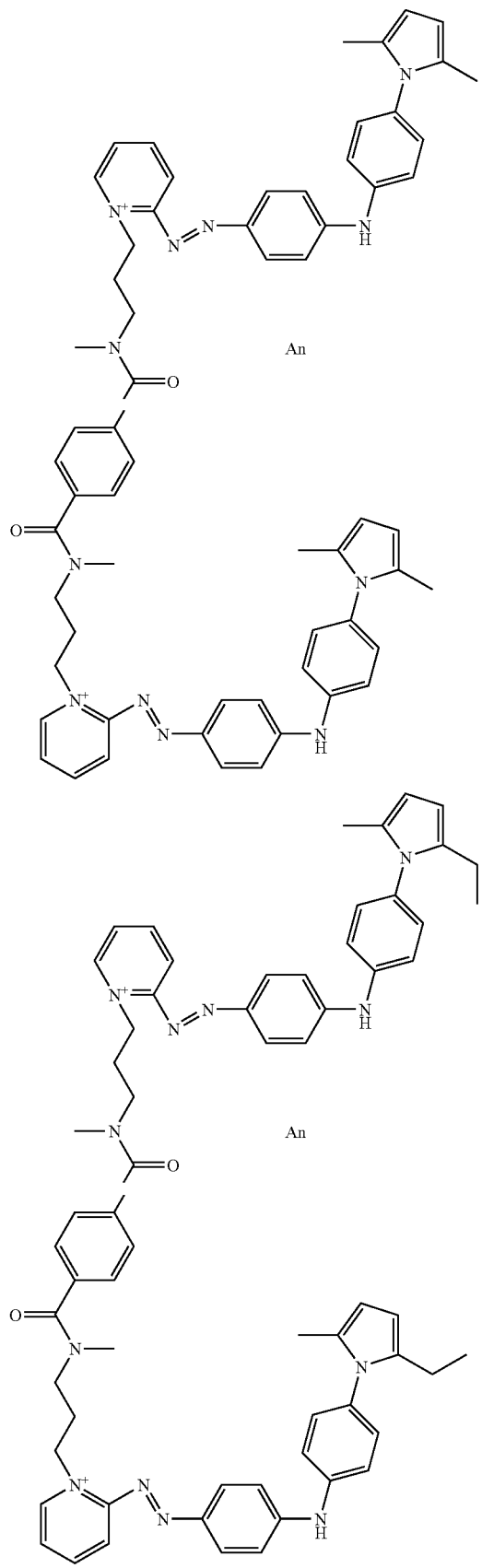
An
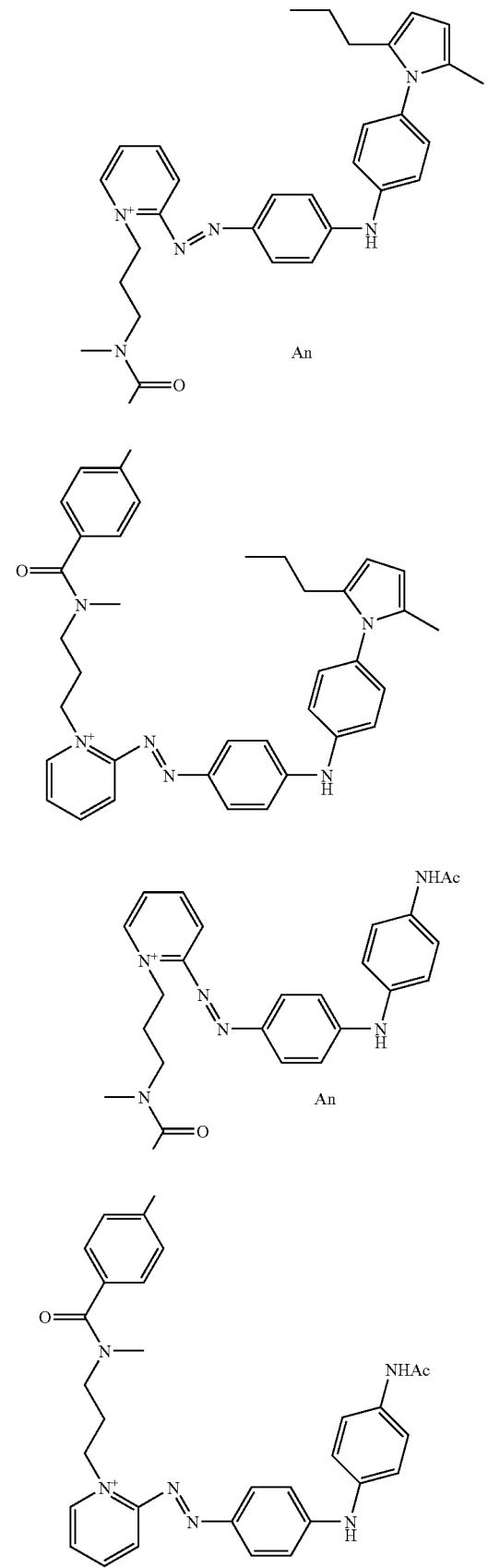
An

-continued
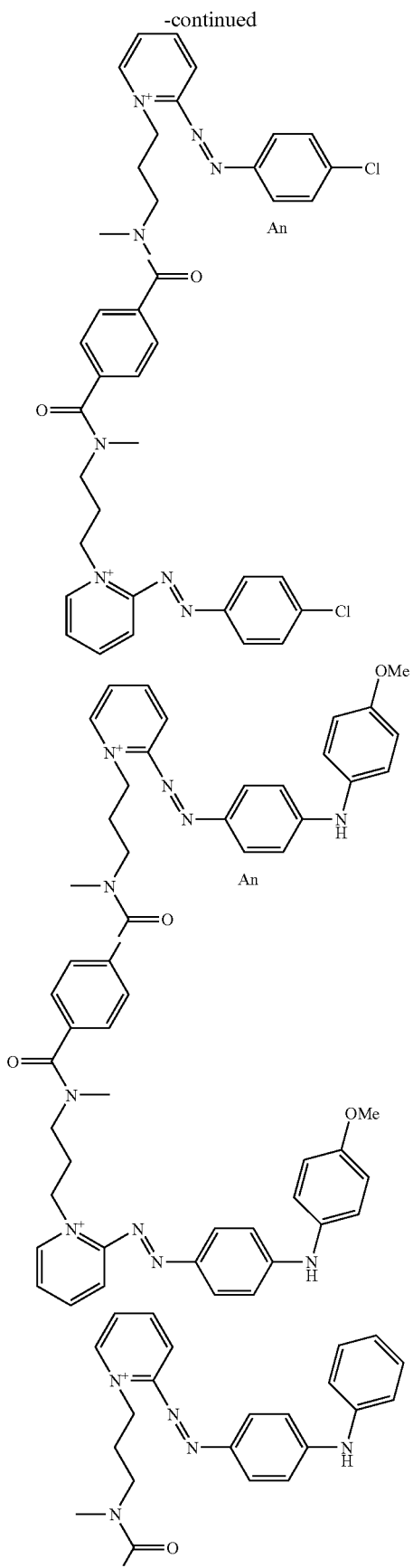
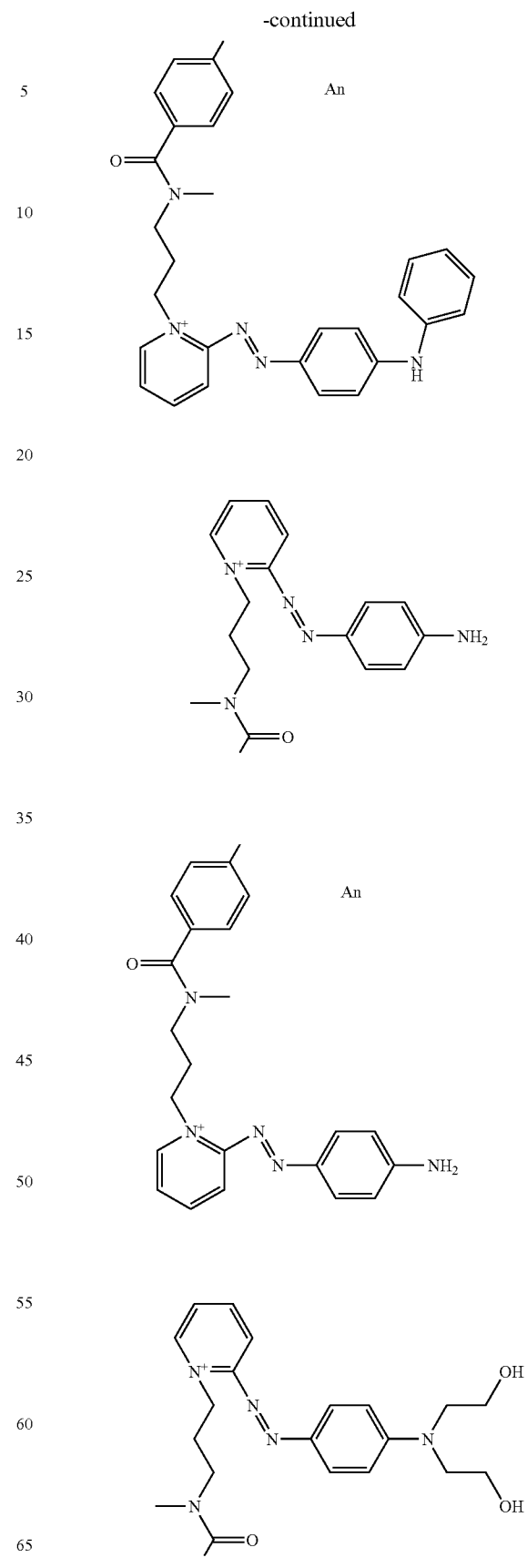

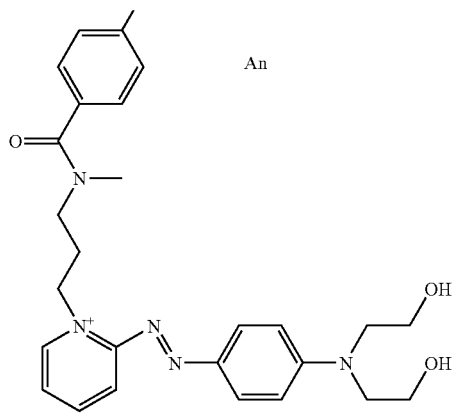
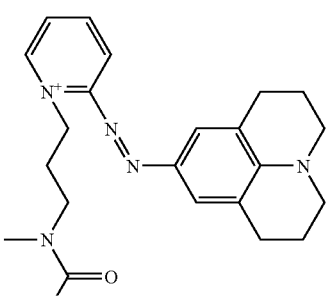
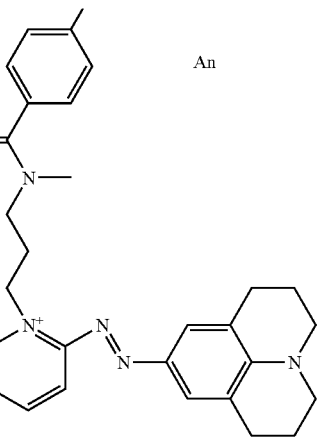
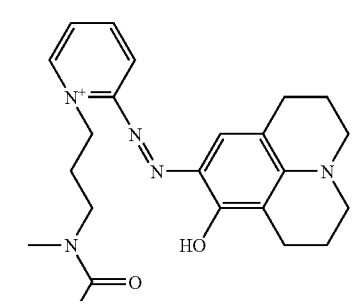
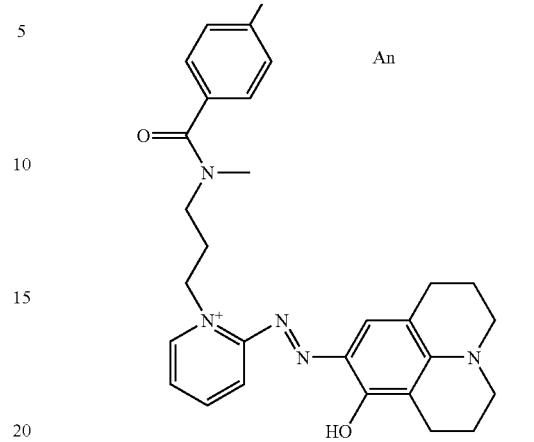
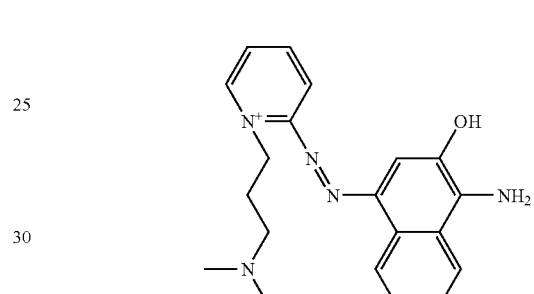
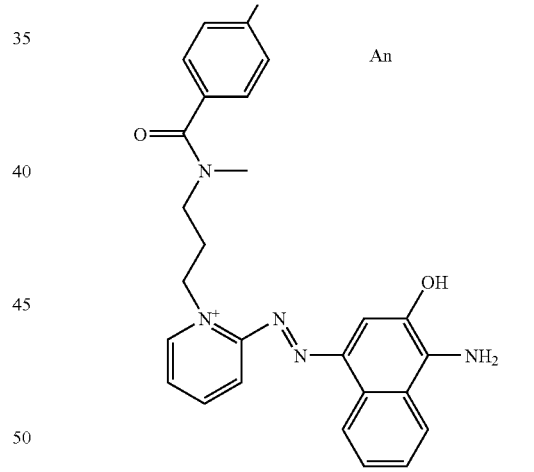
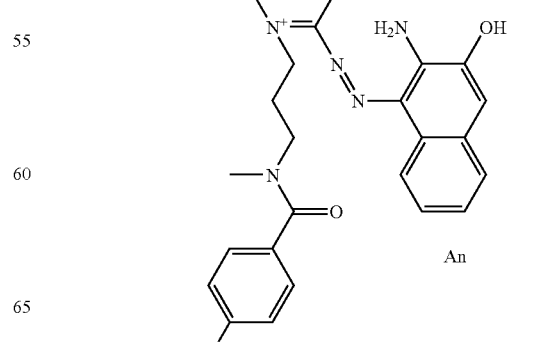

-continued
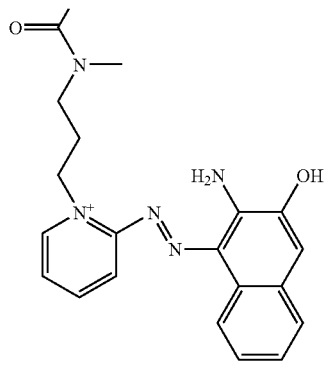
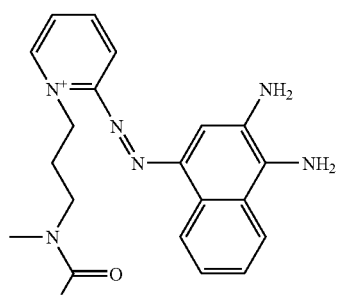
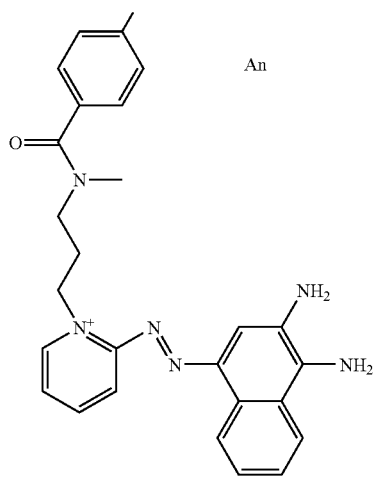
An
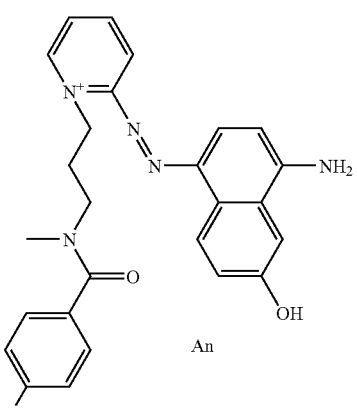
An
-continued
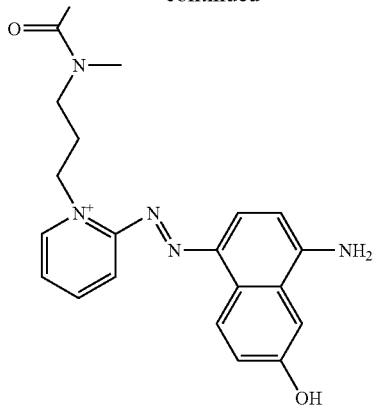
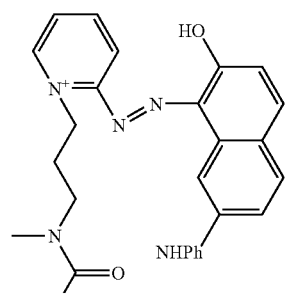
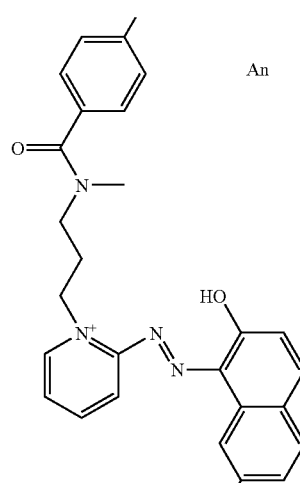
An
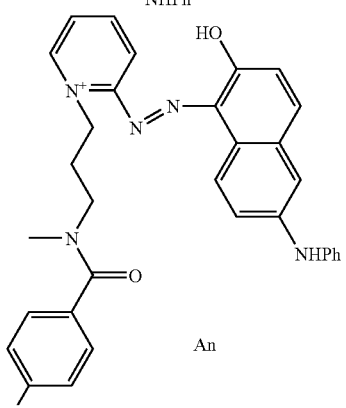
An -continued
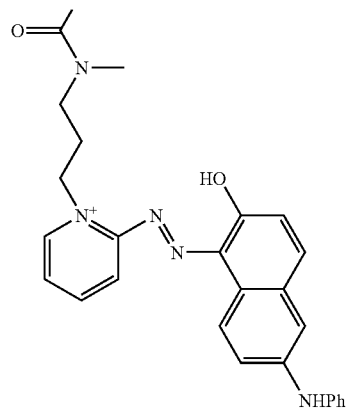
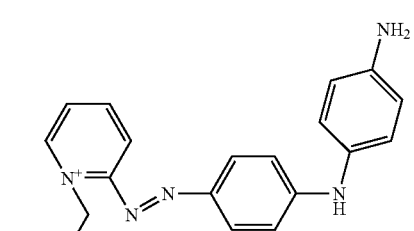
An
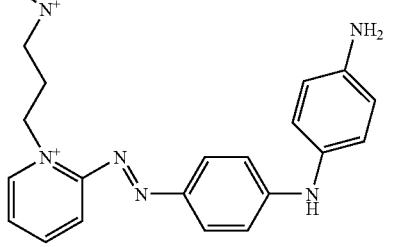
An
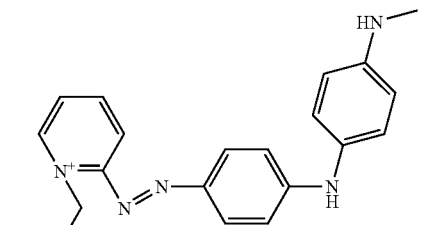
An
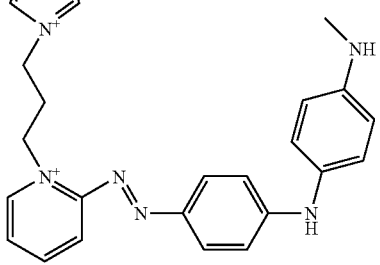
-continued
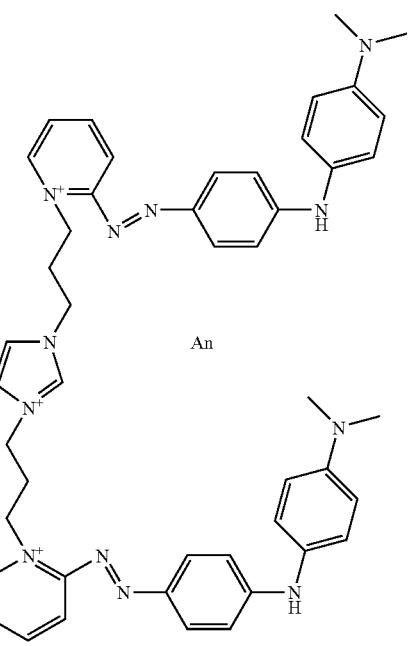
An
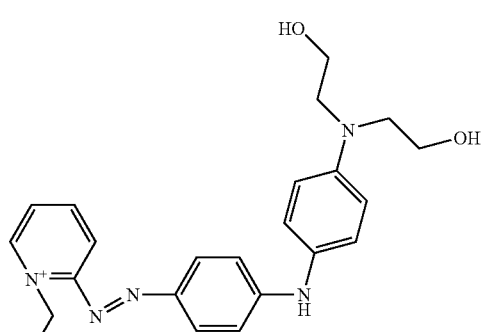
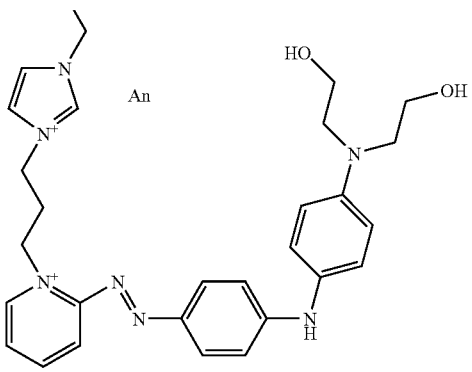
An

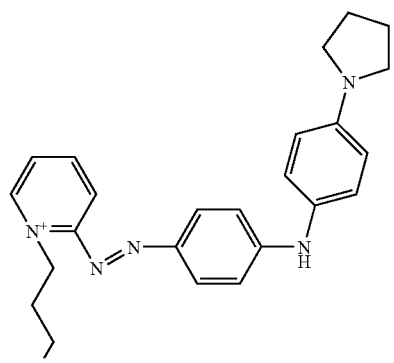
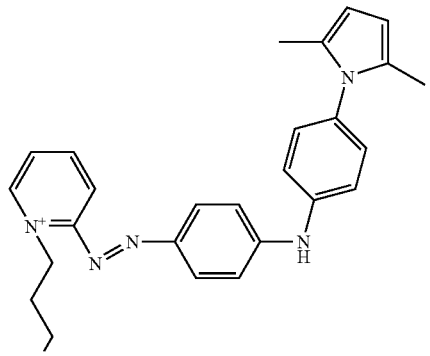
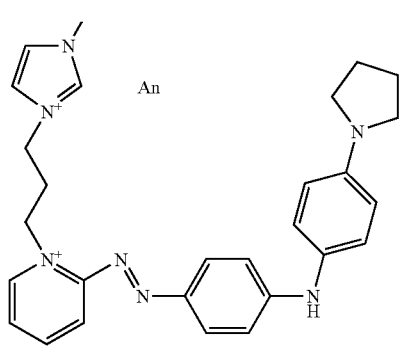
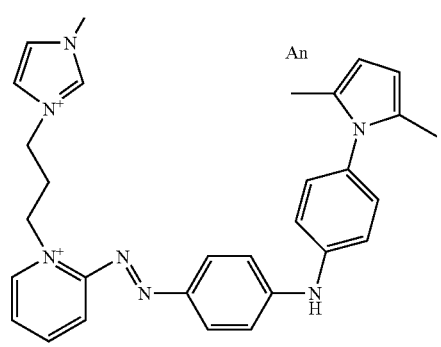
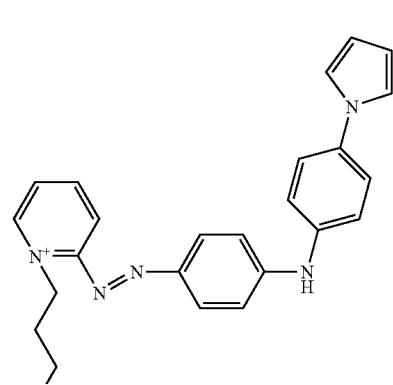
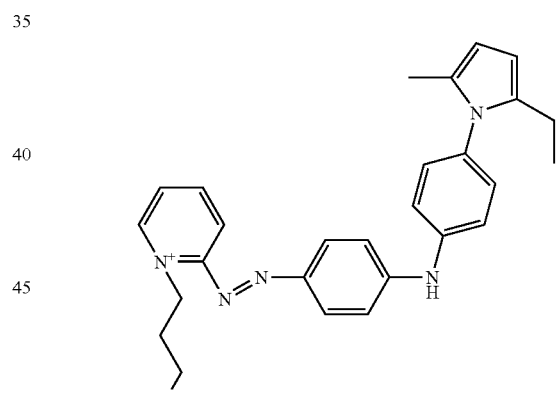
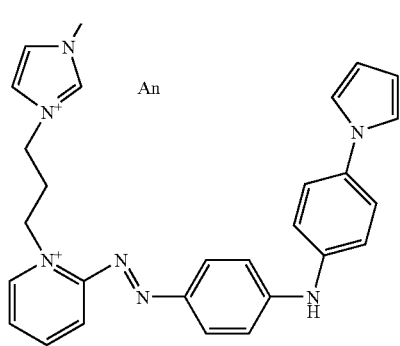
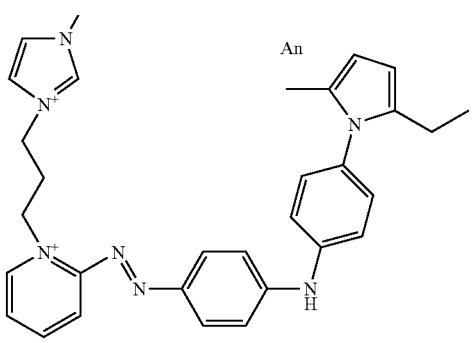

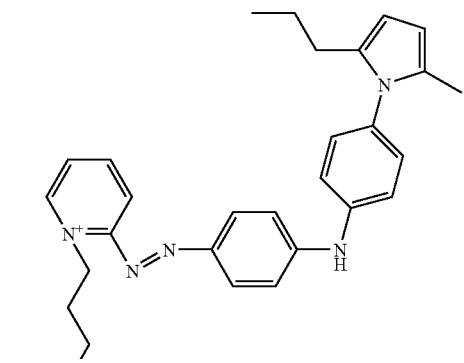
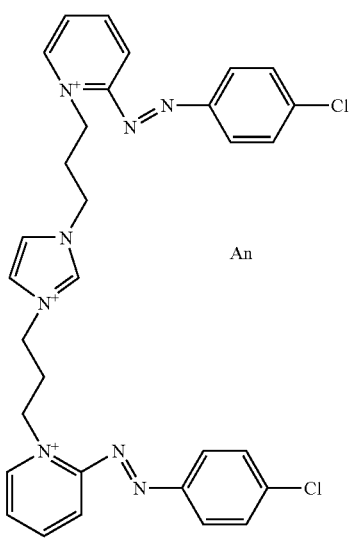
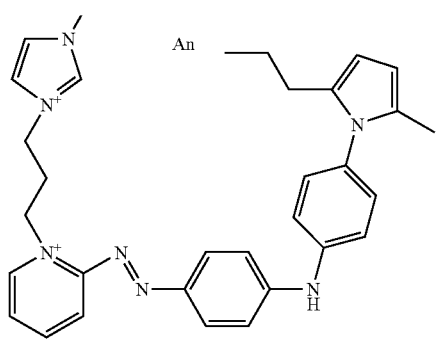
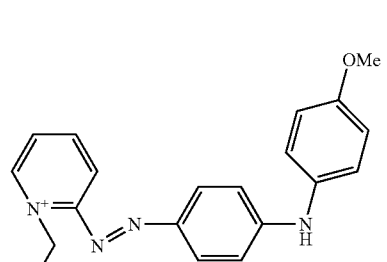
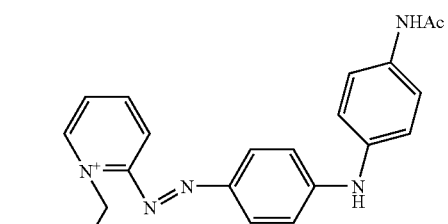

-continued
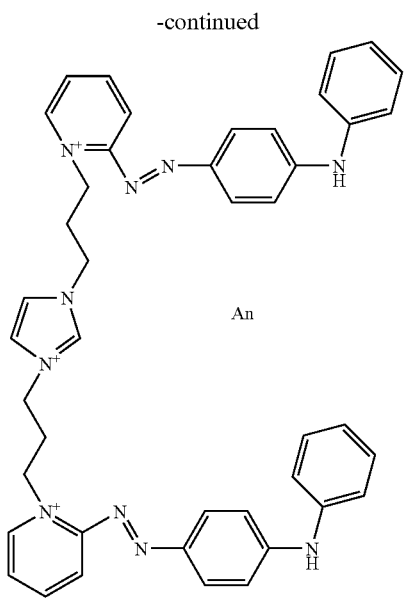
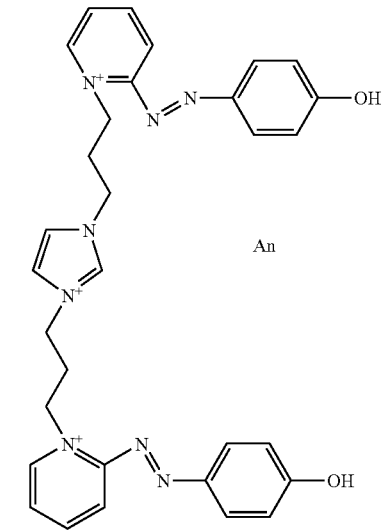
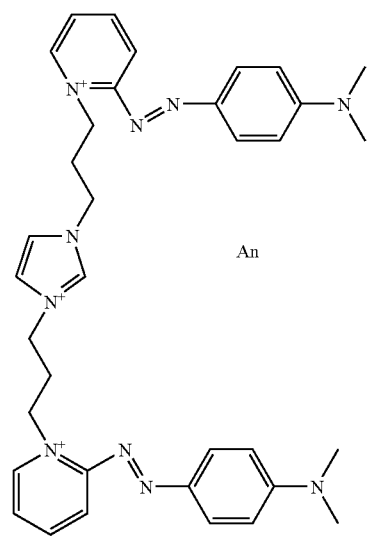
-continued
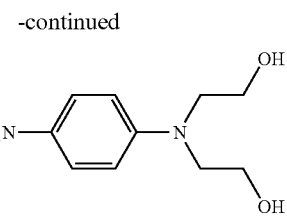
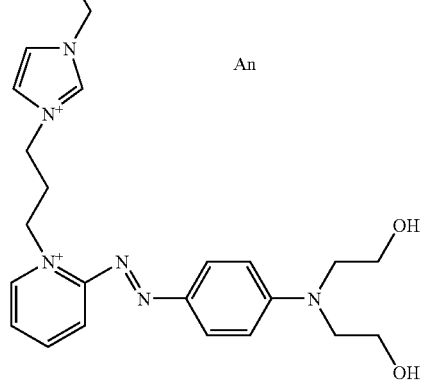
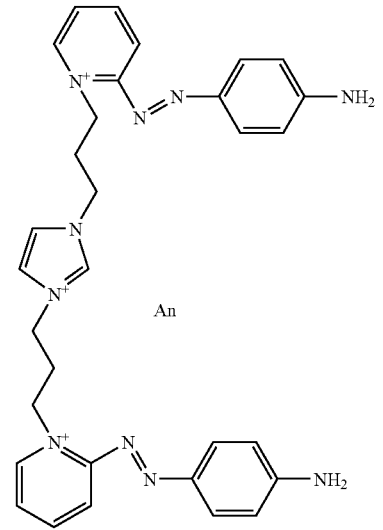
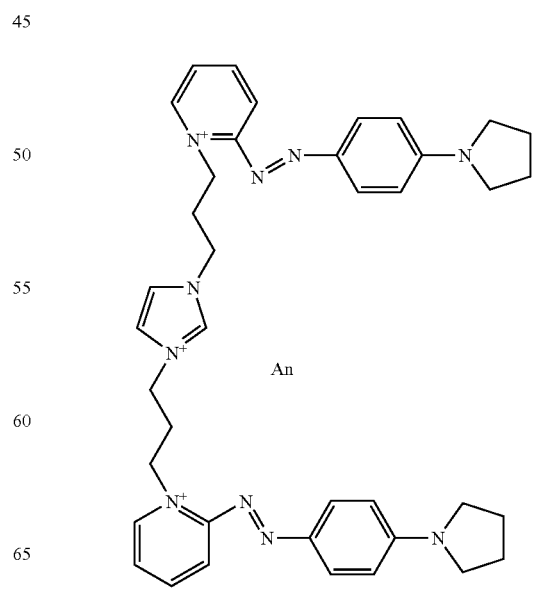

-continued
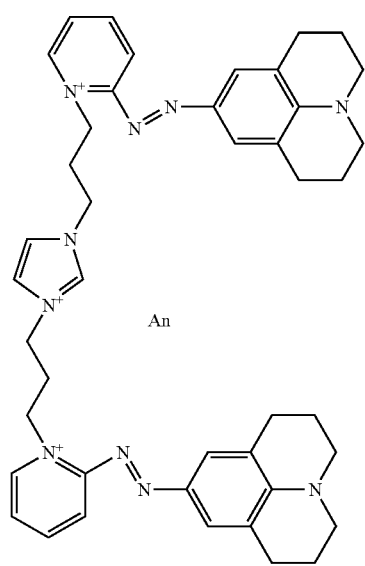
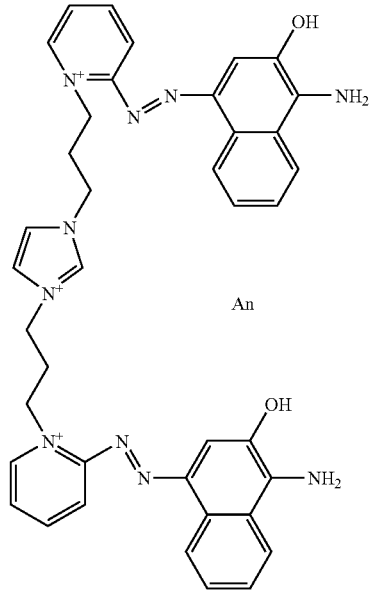

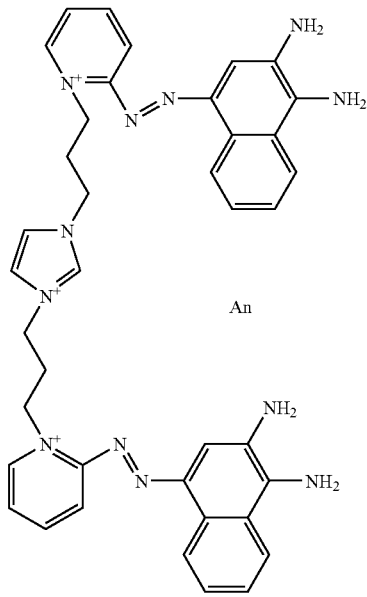
An
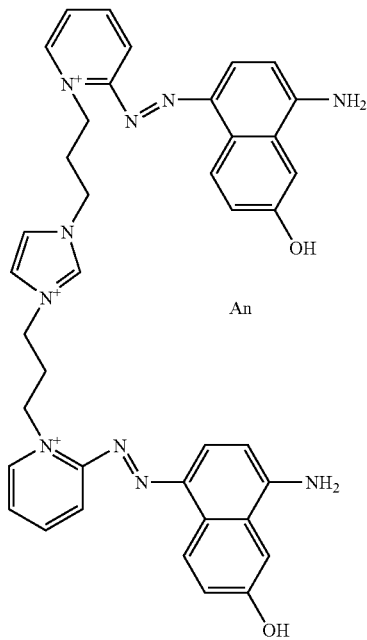
An
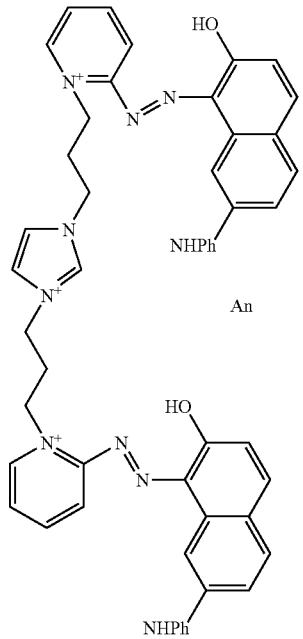
An
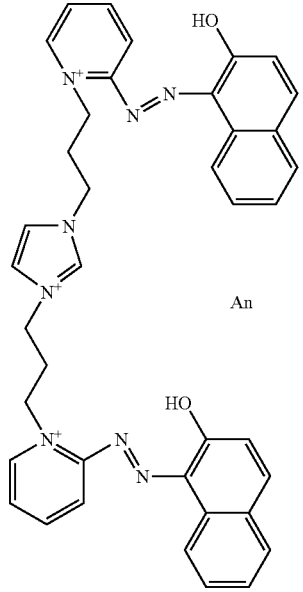
An

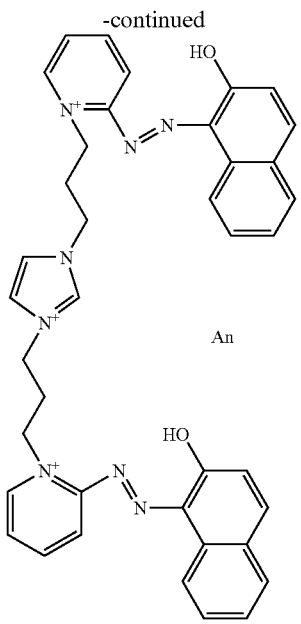

The compounds of the monoazo species may be obtained, for instance, from preparation processes described, for example, in U.S. Pat. Nos. 5,708,151, 3,151,106, and 5,852, 179; J. Chem. Res., Synop. (1998), (10), 648-9; Heterocycles, 1987, 26 (2) 313-7; Synth. Commun. 1999, 29 (13), 2271-6; and Tetrahedron, 1983, 39 (7), 1091-1101. As for the diazo compounds, reference may be made to European Patent Application No. EP 1 377 263 for a synthesis description.

The present disclosure further relates to a dyeing composition comprising at least one compound of formula (I), or the acid addition salts thereof, as direct dye in a medium appropriate for the dyeing of keratin fibers.

The at least one compound of formula (I) can be present in a total amount ranging from 0.001% to 20% by weight, relative to the total weight of the dyeing composition, such as from 0.01% to 10% by weight, and for instance from 0.05% to 5% by weight.

The dyeing composition according to the present disclosure may also comprise at least one oxidation base. This oxidation base may be chosen from the oxidation bases conventionally used in oxidation dyeing, for example para-phenylenediamines, bis(phenyl)alkylenediamines, para-aminophenols, ortho-aminophenols and heterocyclic bases.

Among the para-phenylenediamines that may be used in the present disclosure, non-limiting mention may be made of, for example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β, γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, and the acid addition salts thereof.

Among the para-phenylenediamines mentioned above, further non-limiting mention may be made of para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the acid addition salts thereof.

Among the bis(phenyl)alkylenediamines that may be used as disclosed herein, non-limiting mention may be made of, for example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl) tetramethylenediamine, N,N'-bis(4-methylaminophenyl) tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and the acid addition salts thereof.

Among the para-aminophenols that may be used as disclosed herein, non-limiting mention may be made of, for example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and the acid addition salts thereof.

Among the ortho-aminophenols that may be mentioned, by way of non-limiting example, include 2-aminophenol, 2-amino-5-methylphenol, 2-amino-6-methylphenol, 5-acetamido-2-aminophenol, and the acid addition salts thereof.

Among the heterocyclic bases that may be mentioned, by way of non-limiting example, include pyridine derivatives, pyrimidine derivatives, and pyrazole derivatives.

Among the pyridine derivatives that may be used as disclosed herein, non-limiting mention may be made of the compounds described, for example, in British Patent Nos. GB 1 026 978 and GB 1 153 196, as well as 2,5-diaminopyridine, 2-(4-methoxyphenyl)amino-3-aminopyridine, 2,3-diamino-6-methoxypyridine, 2-(β-methoxyethyl) amino-3-amino-6-methoxypyridine, 3,4-diaminopyridine, and the acid addition salts thereof.

Among the pyrimidine derivatives that may be used as disclosed herein, non-limiting mention may be made of the compounds described, for example, in German Patent No. DE 2 359 399; Japanese Patent Nos. JP 88-169 571 and JP 05-163 124; European Patent No. EP 0 770 375, or International Patent Application Publication No. WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, and 2,5,6-triaminopyrimidine, and pyrazolopyrimidine derivatives such as those mentioned in French Patent Application Publication No. FR-A-2 750 048 and among which non-limiting mention may be made of pyrazolo[1,5-a]pyrimidine-3,7-diamine;

2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]pyrimidine, and the acid addition salts thereof and the tautomeric forms thereof, when a tautomeric equilibrium exists.

Among the pyrazole derivatives that may be used as disclosed herein, non-limiting mention may be made of the compounds described in German Patent Nos. DE 3 843 892, DE 4 133 957, and DE 195 43 988, International Patent Application Publication Nos. WO 94/08969 and WO 94/08970, and French Patent Application Publication No. FR-A-2 733 749, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the acid addition salts thereof.

The dyeing composition according to the present disclosure may also comprise at least one coupler conventionally used for dyeing keratin fibers. Among these couplers, non-limiting mention may be made of, for example, meta-phenylenediamines, meta-aminophenols, meta-diphenols, naphthalenic couplers and heterocyclic couplers.

Further non-limiting examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and the acid addition salts thereof.

In the dyeing composition of the present disclosure the optional at least one oxidation base may be present in a total amount ranging from 0.001% to 10% by weight, relative to the total weight of the dyeing composition, such as ranging from 0.005% to 6% by weight.

The optional at least one coupler may be present in a total amount ranging from 0.001% to 10% by weight, relative to the total weight of the dyeing composition, such as from 0.005% to 6% by weight.

In general, the acid addition salts that may be used in the context of the dyeing compositions of the present disclosure for the oxidation bases and couplers can be chosen from those listed in the context of the definition of the compounds of formula (I).

The composition according to the present disclosure may optionally comprise at least one additional direct dye other than the compounds of formula (I). This dye may be selected from cationic and nonionic species.

Non-limiting examples that may be mentioned include nitrobenzene dyes, azo, azomethine, methine, tetraazapentamethine, anthraquinone, naphthoquinone, benzoquinone, phenothiazine, indigoid, xanthene, phenanthridine and phthalocyanine dyes, dyes derived from triarylmethane, and natural dyes, alone or as mixtures.

The at least one additional direct dye may be chosen, for example, from the following red or orange nitrobenzene dyes:
  1-hydroxy-3-nitro-4-N-(γ-hydroxypropyl)aminobenzene,
  N-(β-hydroxyethyl)amino-3-nitro-4-aminobenzene,
  1-amino-3-methyl-4-N-(β-hydroxyethyl)amino-6-nitrobenzene,
  1-hydroxy-3-nitro-4-N-(β-hydroxyethyl)aminobenzene,
  1,4-diamino-2-nitrobenzene,
  1-amino-2-nitro-4-methylaminobenzene,
  N-(β-hydroxyethyl)-2-nitro-para-phenylenediamine,
  1-amino-2-nitro-4-(β-hydroxyethyl)amino-5-chlorobenzene,
  2-nitro-4-aminodiphenylamine,
  1-amino-3-nitro-6-hydroxybenzene,
  1-(β-aminoethyl)amino-2-nitro-4-(β-hydroxyethyloxy)benzene,
  1-(β,γ-dihydroxypropyl)oxy-3-nitro-4-(β-hydroxyethyl)aminobenzene,
  1-hydroxy-3-nitro-4-aminobenzene,
  1-hydroxy-2-amino-4,6-dinitrobenzene,
  1-methoxy-3-nitro-4-(β-hydroxyethyl)aminobenzene,
  2-nitro-4'-hydroxydiphenylamine, and
  1-amino-2-nitro-4-hydroxy-5-methylbenzene.

The optional at least one additional direct dye may also be chosen from yellow and green-yellow nitrobenzene direct dyes; non-limiting mention may be made, for example, of the compounds chosen from:
  1-β-hydroxyethyloxy-3-methylamino-4-nitrobenzene,
  1-methylamino-2-nitro-5-(β,γ-dihydroxypropyl)oxybenzene,
  1-(β-hydroxyethyl)amino-2-methoxy-4-nitrobenzene,
  1-(β-aminoethyl)amino-2-nitro-5-methoxybenzene,
  1,3-di(β-hydroxyethyl)amino-4-nitro-6-chlorobenzene,
  1-amino-2-nitro-6-methylbenzene,
  1-(β-hydroxyethyl)amino-2-hydroxy-4-nitrobenzene,
  N-(β-hydroxyethyl)-2-nitro-4-trifluoromethylaniline,
  4-(β-hydroxyethyl)amino-3-nitrobenzenesulphonic acid,
  4-ethylamino-3-nitrobenzoic acid,
  4-(β-hydroxyethyl)amino-3-nitrochlorobenzene,
  4-(β-hydroxyethyl)amino-3-nitromethylbenzene,
  4-(β,γ-dihydroxypropyl)amino-3-nitrotrifluoromethylbenzene,
  1-(β-ureidoethyl)amino-4-nitrobenzene,
  1,3-diamino-4-nitrobenzene,
  1-hydroxy-2-amino-5-nitrobenzene,
  1-amino-2-[tris(hydroxymethyl)methyl]amino-5-nitrobenzene, 1-(β-hydroxyethyl)amino-2-nitrobenzene, and
4-(β-hydroxyethyl)amino-3-nitrobenzamide.

Non-limiting mention may also be made of blue or violet nitrobenzene direct dyes; for instance:

1-(β-hydroxyethyl)amino-4-N,N-bis(β-hydroxyethyl) amino-2-nitrobenzene,
1-(γ-hydroxypropyl)amino-4-N,N-bis(β-hydroxyethyl) amino-2-nitrobenzene,
1-(β-hydroxyethyl)amino-4-(N-methyl-N-β-hydroxyethyl)amino-2-nitrobenzene,
1-(β-hydroxyethyl)amino-4-(N-ethyl-N-β-hydroxyethyl) amino-2-nitrobenzene,
1-(β,γ-dihydroxypropyl)amino-4-(N-ethyl-N-β-hydroxyethyl)amino-2-nitrobenzene,
2-nitro-para-phenylenediamines of formula:

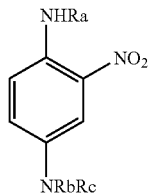

wherein:
Rb is chosen from $C_1$-$C_4$ alkyl radicals and β-hydroxyethyl, β-hydroxypropyl, and γ-hydroxypropyl radicals;
Ra and Rc, which may be identical or different, are chosen from β-hydroxyethyl, β-hydroxypropyl, γ-hydroxypropyl, and β,γ-dihydroxypropyl radicals, at least one of the radicals Rb, Rc or Ra being a γ-hydroxypropyl radical and Rb and Rc not being able to simultaneously be a β-hydroxyethyl radical when Rb is a γ-hydroxypropyl radical, such as those described in French Patent No. FR 2 692 572.

Among the azo direct dyes that may be used according to the present disclosure, non-limiting mention may be made of the cationic azo dyes described in International Patent Application Publication Nos. WO 95/15144, WO 95/01772, WO 02/078660, WO 02/100834, and WO 02/100369, European Patent No. EP 714954, and French Patent Application Nos. FR 2 822 696, FR 2 825 702, FR 2 825 625, FR 2 822 698, FR 2 822 693, FR 2 822 694, FR 2 829 926, FR 2 807 650, and FR 2 844 269.

Among these compounds, further non-limiting mention may be made of the following dyes:
1,3-dimethyl-2-[[4-(dimethylamino)phenyl]azo]-1H-imidazolium chloride,
1,3-dimethyl-2-[(4-aminophenyl)azo]-1H-imidazolium chloride,
1-methyl-4-[(methylphenylhydrazono)methyl]pyridinium methylsulphate.

Among the azo direct dyes that may also be mentioned in a non-limiting manner are the following dyes described in the Color Index International 3rd edition:
Disperse Red 17,
Acid Yellow 9,
Acid Black 1,
Basic Red 22,
Basic Red 76,
Basic Yellow 57,
Basic Brown 16,
Acid Yellow 36,
Acid Orange 7,
Acid Red 33,
Acid Red 35,
Basic Brown 17,
Acid Yellow 23,
Acid Orange 24, and
Disperse Black 9.

Further non-limiting mention may also be made of 1-(4'-aminodiphenylazo)-2-methyl-4-[bis(β-hydroxyethyl) amino]benzene and 4-hydroxy-3-(2-methoxyphenylazo)-1-naphthalenesulphonic acid.

Among the quinone direct dyes that may be used as disclosed herein, non-limiting mention may be made of the following dyes:
Disperse Red 15,
Solvent Violet 13,
Acid Violet 43,
Disperse Violet 1,
Disperse Violet 4,
Disperse Blue 1,
Disperse Violet 8,
Disperse Blue 3,
Disperse Red 11,
Acid Blue 62,
Disperse Blue 7,
Basic Blue 22,
Disperse Violet 15,
Basic Blue 99,
and also the following compounds:
1-N-methylmorpholiniumpropylamino-4-hydroxyanthraquinone,
1-aminopropylamino-4-methylaminoanthra-quinone,
1-aminopropylaminoanthraquinone,
5-β-hydroxyethyl-1,4-diaminoanthraquinone,
2-aminoethylaminoanthraquinone, and
1,4-bis(β,γ-dihydroxypropylamino)anthraquinone.

Among the azine dyes that may be used, non-limiting mention may be made of the following compounds:
Basic Blue 17, and
Basic Red 2.

Among the triarylmethane dyes that may be used according to the present disclosure, non-limiting mention may be made of the following compounds:
Basic Green 1,
Acid Blue 9,
Basic Violet 3,
Basic Violet 14,
Basic Blue 7,
Acid Violet 49,
Basic Blue 26, and
Acid Blue 7.

Among the indoamine dyes that may be used according to the present disclosure, non-limiting mention may be made of the following compounds:
2-β-hydroxyethylamino-5-[bis(β-4'-hydroxyethyl)amino] anilino-1,4-benzoquinone;
2-β-hydroxyethylamino-5-(2'-methoxy-4'-amino)anilino-1,4-benzoquinone;
3-N-(2'-chloro-4'-hydroxy)phenylacetyl-amino-6-methoxy-1,4-benzoquinoneimine;
3-N-(3'-chloro-4'-methylamino)phenylureido-6-methyl-1,4-benzoquinoneimine; and
3-[4'-N-(ethylcarbamylmethyl)amino]phenylureido-6-methyl-1,4-benzoquinoneimine.

Among the dyes of tetraazapentamethine type that may be used according to the present disclosure, non-limiting mention may be made of the following compounds given in the table below, An being defined as above:

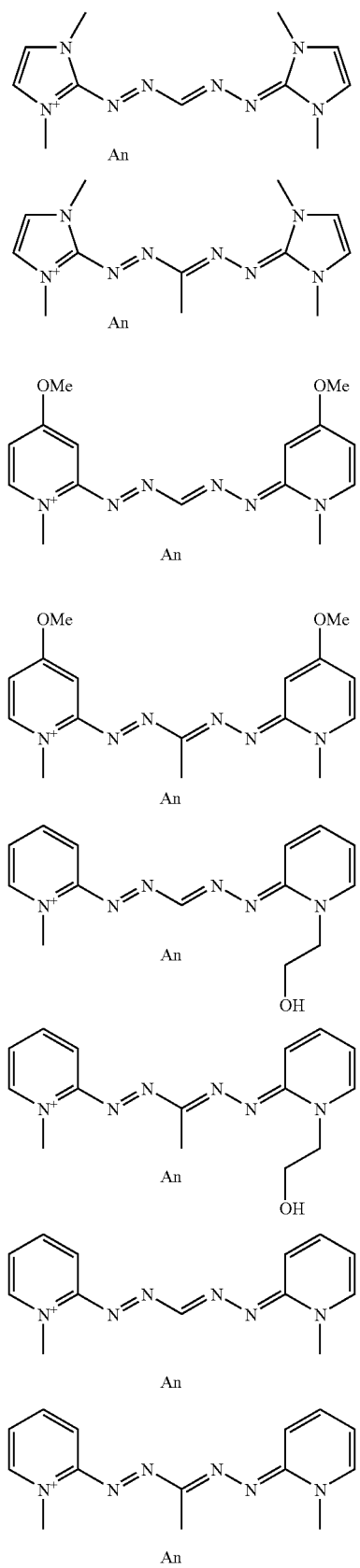

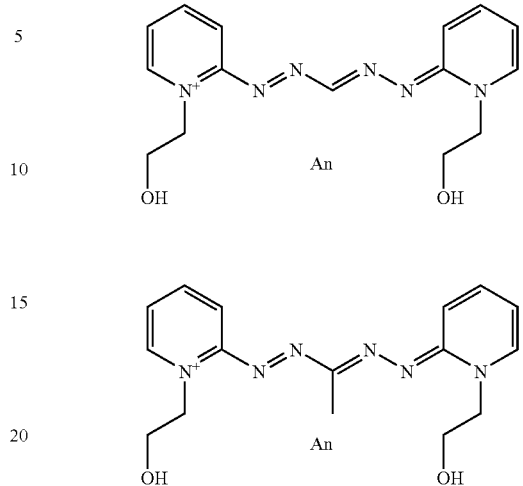

Among the natural direct dyes that may be used according to the present disclosure, non-limiting mention may be made of lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes may also be used, such as henna-based poultices or extracts.

When present, the at least one additional direct dye can be present in the composition in a total amount ranging from 0.001% to 20% by weight, relative to the total weight of the composition, such as from 0.01% to 10% by weight, relative to the weight of the composition.

The medium that is suitable for dyeing, also known as the dye vehicle, generally consists of water or comprises a mixture of water and of at least one organic solvent to dissolve the compounds that would not be sufficiently water-soluble.

For example, the at least one organic solvent can be chosen from linear and branched, and for instance, saturated monoalcohols or diols comprising 2 to 10 carbon atoms, such as ethyl alcohol, isopropyl alcohol, hexylene glycol (2-methyl-2,4-pentanediol), neopentyl glycol and 3-methyl-1,5-pentanediol; aromatic alcohols such as benzyl alcohol and phenylethyl alcohol; glycols and glycol ethers, for instance ethylene glycol monomethyl, monoethyl and monobutyl ether, propylene glycol and its ethers, for instance propylene glycol monomethyl ether, butylene glycol and dipropylene glycol; and also diethylene glycol alkyl ethers, such as the $C_1$-$C_4$ ethers, for instance diethylene glycol monoethyl ether or monobutyl ether, alone or as a mixture.

The at least one solvent described above, when it is present, can be present in a total amount ranging from 1% to 40% by weight, such as from 5% to 30% by weight, relative to the total weight of the composition.

The dyeing composition in accordance with the present disclosure may also include at least one adjuvant conventionally used in compositions for dyeing the hair, such as anionic, cationic, nonionic, amphoteric and zwitterionic surfactants; anionic, cationic, nonionic, amphoteric and zwitterionic polymers; mineral and organic thickeners, such as anionic, cationic, nonionic and amphoteric polymeric associative thickeners; antioxidants; penetrants; sequestrants; fragrances; buffers; dispersants; conditioning agents, for instance silicones, which may or may not be volatile or be modified; film-forming agents; ceramides; preservatives and opacifiers.

These at least one adjuvant can be present in an amount for each adjuvant, ranging from 0.01% to 20% by weight, relative to the total weight of the composition.

The person skilled in the art will of course take care to select this or these optional additional compounds such that the beneficial properties intrinsically associated with the dyeing composition in accordance with the present disclosure are not, or not substantially, adversely affected by the envisaged addition(s).

The pH of the dyeing composition in accordance with the present disclosure can range from 3 to 12, such as from 5 to 11. It may be adjusted to the desired value using acidifying or alkalifying agents usually used in the dyeing of keratin fibers, or alternatively using standard buffer systems.

Among the acidifying agents that may be mentioned, by way of non-limiting example, are mineral and organic acids such as hydrochloric acid, orthophosphoric acid, sulphuric acid, carboxylic acids such as acetic acid, tartaric acid, citric acid and lactic acid, and sulphonic acids.

Among the alkalifying agents that may be mentioned, by way of non-limiting example, are aqueous ammonia, alkaline carbonates, alkanolamines such as monoethanolamine, diethanolamine and triethanolamine and derivatives thereof, sodium hydroxide, potassium hydroxide and the compounds having the following formula:

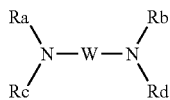

in which W is a propylene residue optionally substituted by a hydroxyl group or a $C_1$-$C_4$ alkyl radical; Ra, Rb, Rc and Rd, which may be identical or different, are chosen from hydrogen atoms and $C_1$-$C_4$ alkyl and $C_1$-$C_4$ hydroxyalkyl radicals.

The dyeing composition according to the present disclosure may be in various forms, such as in the form of liquids, creams or gels, or in any other form that is suitable for dyeing keratin fibers, including human hair.

The composition according to the present disclosure may further comprise at least one oxidizing agent. In this case, the composition is referred to as a ready-to-use composition.

As used herein, the term "a ready-to-use composition" is understood to mean a composition intended to be applied immediately to the keratin fibers, i.e. it may be stored in unmodified form before use or may result from the extemporaneous mixing of two or more compositions. Said composition may also be obtained by mixing at least one composition according to the present disclosure with at least one oxidizing composition.

The at least one oxidizing agent may be chosen from any oxidizing agent conventionally used in the field. Thus it may be chosen from hydrogen peroxide, urea peroxide, alkali metal bromates, persalts such as perborates and persulphates, and also enzymes, among which non-limiting mention may be made of peroxidases, 2-electron oxidoreductases such as uricases, and 4-electron oxygenases, for instance laccases. In one embodiment of the present disclosure, hydrogen peroxide is used.

The at least one oxidizing agent can be present in an amount ranging from 1% and 40% by weight, relative to the total weight of the ready-to-use composition, and such as from 1% to 20% by weight, relative to the total weight of the ready-to-use composition.

Generally, the oxidizing composition used is an aqueous composition and may be in the form of a solution or an emulsion.

Usually, the composition free of oxidizing agent is mixed with from 0.5 to 10 weight equivalents of the oxidizing composition.

It should be noted that the pH of the ready-to-use composition ranges from 4 to 12, such as from 7 to 11.5.

The pH of the ready-to-use composition may be adjusted using an acidifying or alkalifying agent chosen, for example, from those mentioned previously in the context of the description according to the present disclosure.

The present disclosure further relates to a method for coloring keratin fibers that comprises the application of a dyeing composition according to the present disclosure to the wet or dry keratin fibers.

The application to the fibers of the dyeing composition comprising at least one compound of formula (I) and/or the addition salts thereof with an acid, optionally at least one oxidation base optionally combined with at least one coupler, and optionally at least one additional direct dye, may be performed in the presence of at least one oxidizing agent.

The at least one oxidizing agent may be added to the composition comprising the at least one compound of formula (I) and the optional oxidation bases, couplers and/or additional direct dyes, either at the time of use or directly on the keratin fiber.

The oxidizing composition may also include at least one adjuvant conventionally used in compositions for dyeing keratin fibers and as defined above.

The pH of the oxidizing composition comprising the at least one oxidizing agent is such that, after mixing with the dye composition, the pH of the resulting ready-to-use composition applied to the keratin fibers ranges from 4 to 12, such as from 7 to 11.5. It may be adjusted to the desired value by means of acidifying or alkalifying agents usually used in the dyeing of keratin fibers and as defined above.

The composition that is finally applied to the keratin fibers may be in various forms, such as in the form of liquids, creams or gels or in any other form that is suitable for dyeing keratin fibers, including human hair.

According to one embodiment of the present disclosure, the composition according to the present disclosure does not comprise an oxidation base or a coupler.

The composition applied, as discussed above, may optionally comprise at least one oxidizing agent.

The composition is thus applied to the wet or dry keratin fibers and is then left for a period of leave-in time that is sufficient to give the desired coloration.

Whatever the version of composition used (i.e., with or without at least one oxidizing agent), the leave-in time can range from a few seconds to one hour, for instance, from 3 minutes to 30 minutes.

The temperature at which the composition is left to act can range from 15° C. to 220° C., for example from 15° C. to 80° C., such as from 15° C. to 40° C.

After the period of leave-in time has ended, the composition is removed, normally by rinsing with water, optionally followed by washing with a shampoo, and then optionally by drying.

Another embodiment of the present disclosure is a device having a plurality of compartments or dyeing kit, in which a first compartment contains at least one dyeing composition of the present disclosure and a second compartment contains at least one oxidizing composition. This device may be equipped with an applicator for delivering the desired mixture to the hair, such as the devices described in French Patent No. FR-2 586 913.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements.

The examples that follow serve to illustrate the invention without, however, being limiting in nature.

EXAMPLES

Synthesis Examples

1) Synthesis of Compound 2:

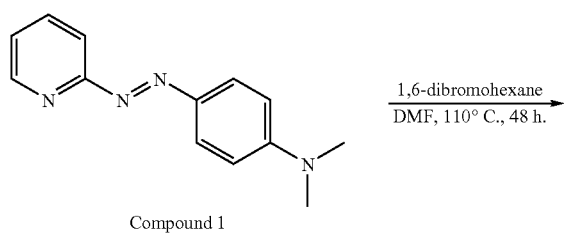

Compound 1

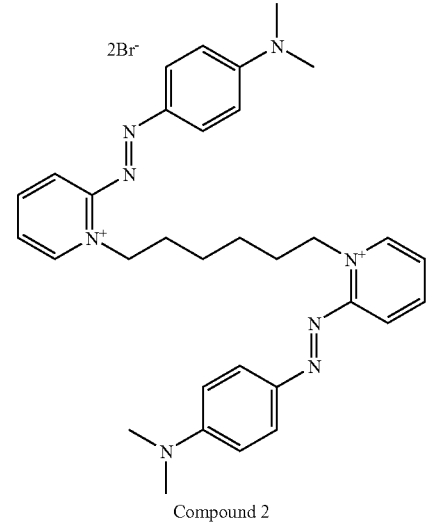

Compound 2

Compound 1 (commercial compound Interchim, 22.6 g) was reacted in the presence of 8 ml of 1,6-dibromohexane in 200 ml of dimethylformamide at 110° C. for 48 hours. After being brought to ambient temperature, the reaction mixture is poured into 500 ml of diisopropyl ether. The precipitate obtained is filtered off and then dried under vacuum. A violet powder was obtained which corresponded to compound 2.

The 1H NMR and mass analyses were in accordance with the expected product.

2) Synthesis of Compound 3:

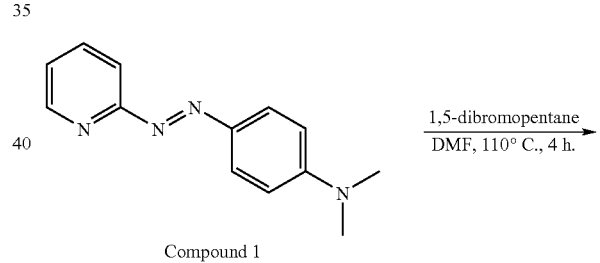

Compound 1

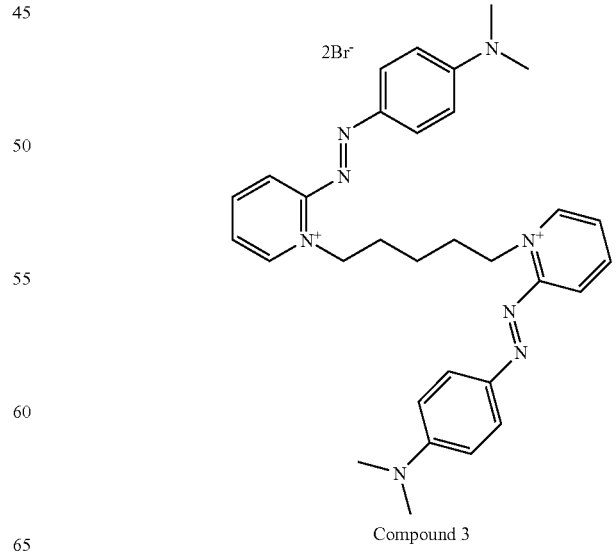

Compound 3

Compound 1 (commercial compound Interchim, 22.6 g) was reacted in the presence of 8 ml of 1,5-dibromopentane in 150 ml of dimethylformamide at 110° C. for 4 hours. After being brought to ambient temperature, the reaction mixture was poured into 500 ml of diisopropyl ether. The precipitate obtained was filtered off and then dried under vacuum. A violet powder was obtained which corresponded to compound 3.

The 1H NMR and mass analyses were in accordance with the expected product.

3) Synthesis of Compound 4:

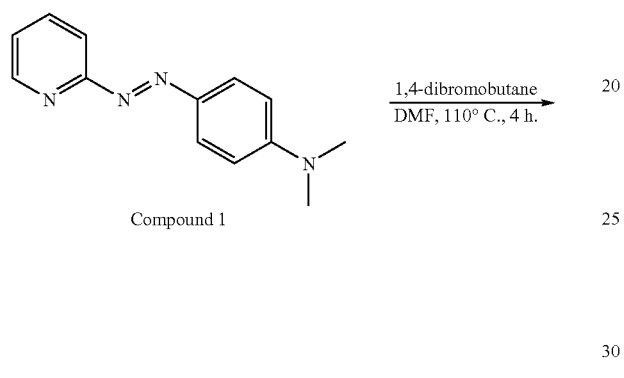

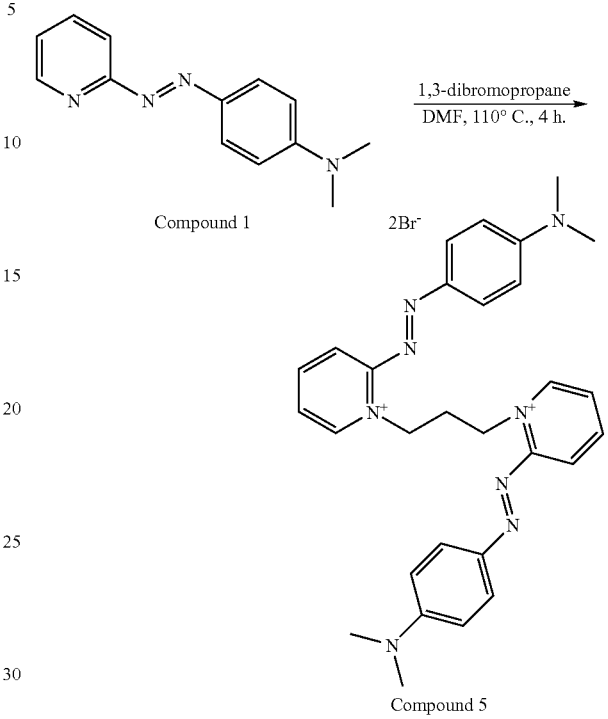

Compound 1 (commercial compound Interchim, 22.6 g) was reacted in the presence of 7.7 ml of 1,4-dibromobutane in 150 ml of dimethylformamide at 110° C. for 4 hours. After being brought to ambient temperature, the reaction mixture was poured into 500 ml of diisopropyl ether. The precipitate obtained was filtered off and then dried under vacuum. A violet powder was obtained which corresponded to compound 4.

The 1H NMR and mass analyses were in accordance with the expected product.

4) Synthesis of Compound 5:

Compound 1 (commercial compound Interchim, 22.6 g) was reacted in the presence of 7.5 ml of 1,3-dibromopropane in 150 ml of dimethylformamide at 110° C. for 4 hours. After being brought to ambient temperature, the reaction mixture was poured into 500 ml of diisopropyl ether. The precipitate obtained was filtered off and then dried under vacuum. A violet powder was obtained which corresponded to compound 5.

The 1H NMR and mass analyses were in accordance with the expected product.

5) Synthesis of Compound 8:

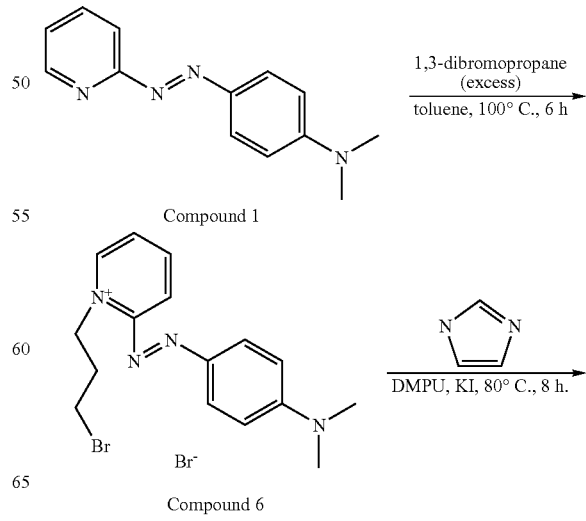

-continued

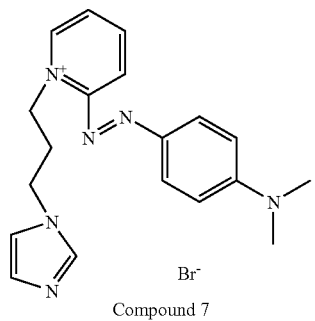
Compound 7

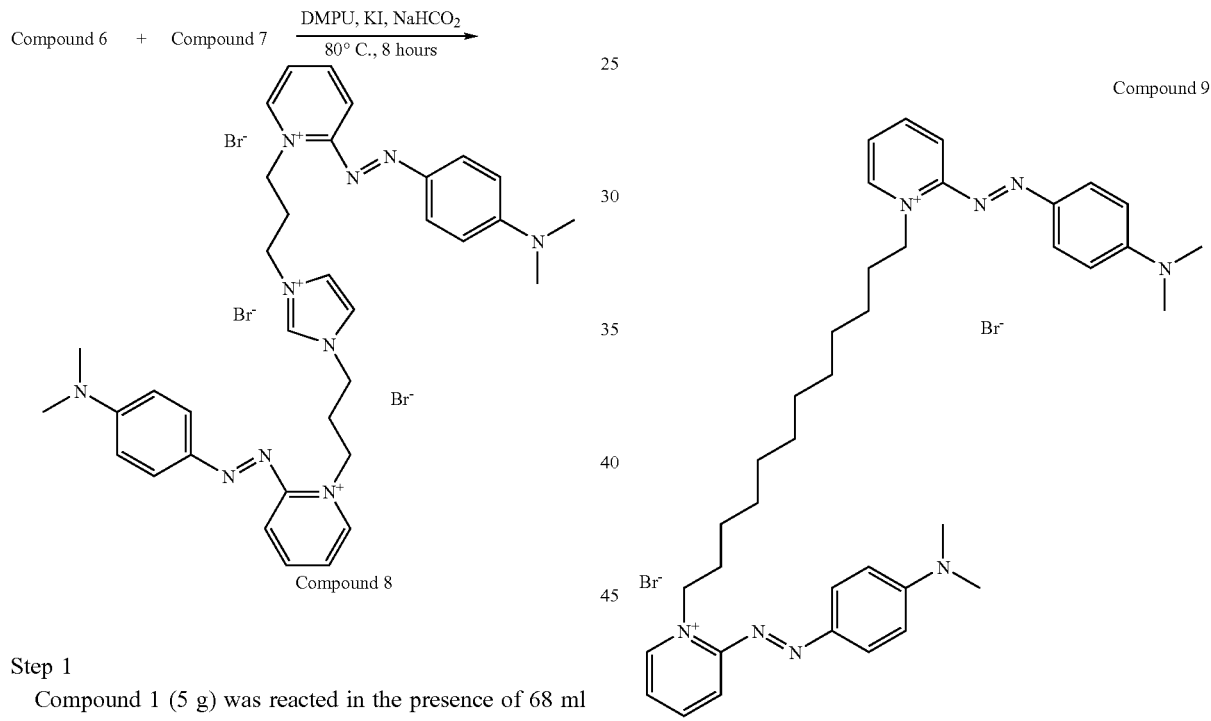
Compound 8

Step 1

Compound 1 (5 g) was reacted in the presence of 68 ml of 1,3-dibromopropane in 350 ml of toluene at 100° C. for 6 hours. After being brought to ambient temperature, the reaction mixture was poured into 500 ml of ethyl acetate. A precipitate was formed. The precipitate obtained was washed a number of times with ethyl acetate, filtered off and then dried under vacuum. A violet powder was obtained which corresponded to the structure of compound 6.

The 1H NMR and mass analyses are in accordance with the expected product.

Step 2

Compound 6 (5 g) was reacted in the presence of 4.9 g of imidazole and 2.4 g of potassium iodide in 30 ml of DMPU at 80° C. for 8 hours. After being brought to ambient temperature, the reaction mixture was poured into 200 ml of ethyl acetate. A dark violet precipitate was formed. This precipitate was filtered and dried under vacuum. A dark violet powder was obtained which corresponded to compound 7.

The 1H NMR and mass analyses were in accordance with the expected product.

Step 3

Compound 6 (2 g), 2.1 g of compound 7 and 1 g of potassium iodide were reacted in 40 ml of DMPU at 80° C. for 8 hours. After being brought to ambient temperature, the reaction mixture was poured into 500 ml of ethyl acetate. The violet residue was subsequently taken up in methanol and then precipitated slowly by adding ethyl acetate. A dark violet powder was obtained which corresponded to compound 8.

The 1H NMR and mass analyses were in accordance with the expected product.

6) Synthesis of Compound 9:

Synthesis of 1,1'-dodecane-1,12-diylbis(2-{(E)-[4-(dimethylamino)phenyl]diazenyl}pyridinium) dibromide

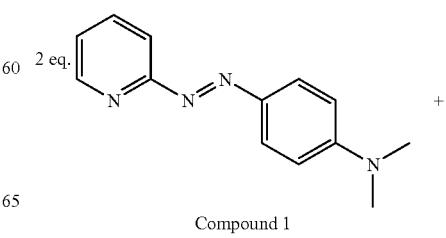

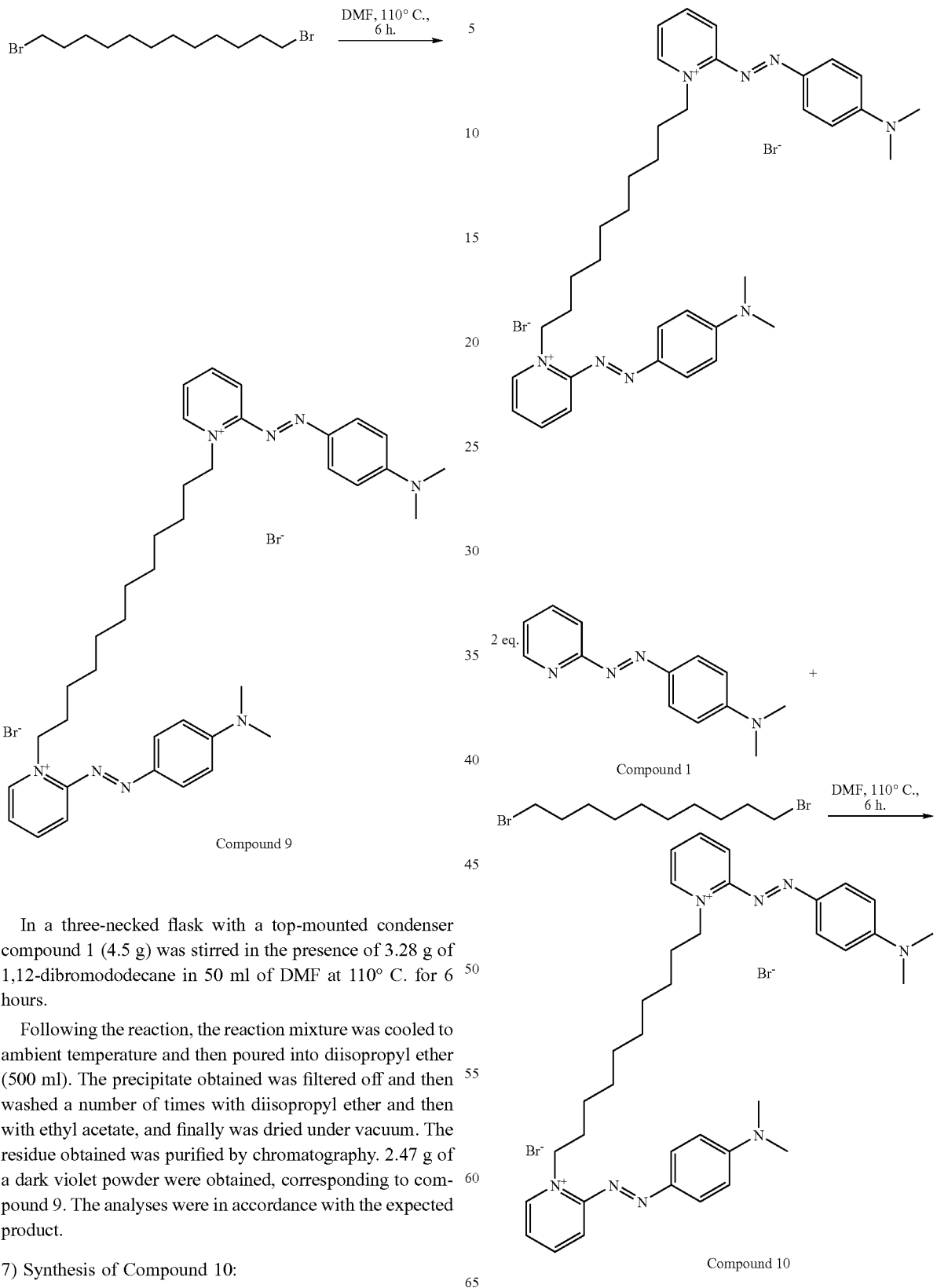

In a three-necked flask with a top-mounted condenser compound 1 (4.5 g) was stirred in the presence of 3.28 g of 1,12-dibromododecane in 50 ml of DMF at 110° C. for 6 hours.

Following the reaction, the reaction mixture was cooled to ambient temperature and then poured into diisopropyl ether (500 ml). The precipitate obtained was filtered off and then washed a number of times with diisopropyl ether and then with ethyl acetate, and finally was dried under vacuum. The residue obtained was purified by chromatography. 2.47 g of a dark violet powder were obtained, corresponding to compound 9. The analyses were in accordance with the expected product.

7) Synthesis of Compound 10:

Synthesis of 1,1'-decane-1,10-diylbis(2-{(E)-[4-(dimethylamino)phenyl]diazenyl}pyridinium) dibromide In a three-necked flask with a top-mounted condenser compound 1 (4.5 g) was stirred in the presence of 3 g of 1,10-dibromodecane in 50 ml of DMF at 110° C. for 6 hours.

Following the reaction, the reaction mixture was cooled to ambient temperature and then poured into diisopropyl ether (500 ml). The precipitate obtained was filtered off and then washed a number of times with diisopropyl ether and then with ethyl acetate, and finally was dried under vacuum. The residue obtained was purified by centrifugal partition chromatography (solvents used: n-butanol/water). 0.75 g of a dark violet powder was obtained, corresponding to compound 10. The analyses were in accordance with the expected product.

8) Synthesis of Compound 11:

Synthesis of 1,1'-tetradecane-1,14-diylbis(2-{(E)-[4-(dimethylamino)phenyl]diazenyl}pyridinium) dibromide

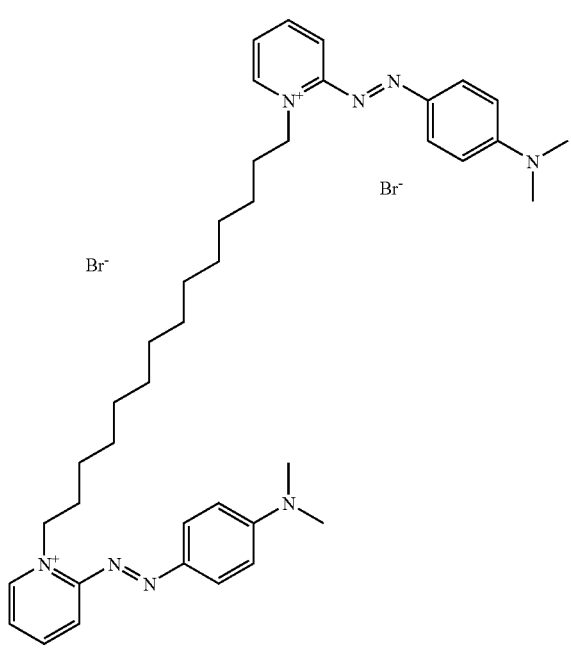

Compound 11

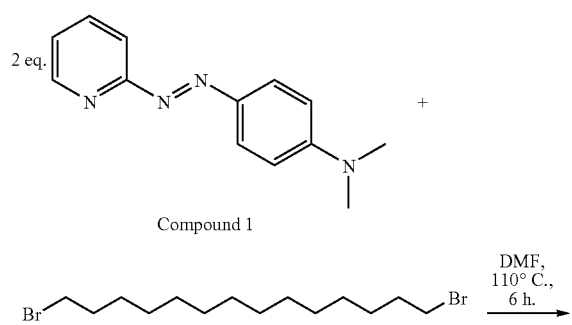

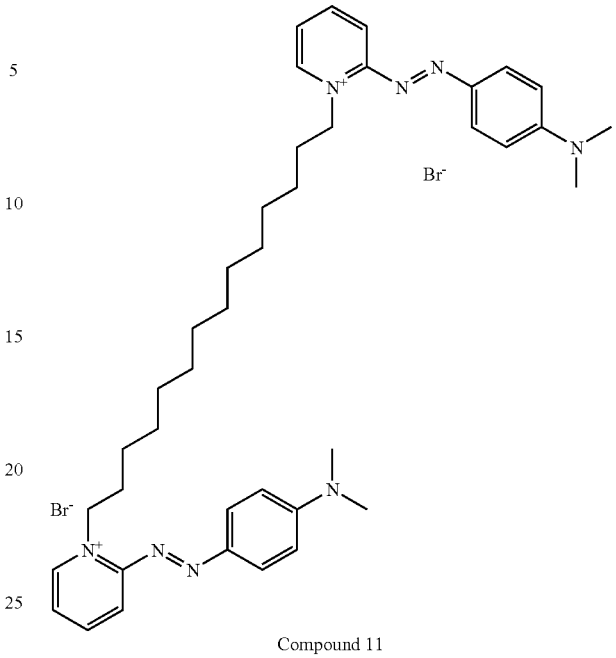

Compound 11

In a three-necked flask with a top-mounted condenser compound 1 (4.5 g) was stirred in the presence of 3.56 g of 1,14-dibromotetradecane in 50 ml of DMF at 110° C. for 6 hours.

Following the reaction, the reaction mixture was cooled to ambient temperature and then poured into diisopropyl ether (500 ml). The precipitate obtained was filtered off and then washed a number of times with diisopropyl ether and then with ethyl acetate, and finally was dried under vacuum. The residue obtained was purified by chromatography. 3.16 g of a dark violet powder were obtained, corresponding to compound 11. The analyses were in accordance with the expected product.

Dyeing Examples

The following dyeing compositions were prepared:

| Dye | $10^{-3}$ mol |
|---|---|
| Dyeing vehicle | (*) |
| Demineralized water qs | 100 g |

(*): dyeing vehicle (1) pH 7 or (2) pH 9.5

Dyeing Vehicle (1) pH 7:

| 96° ethyl alcohol | 20.8 g |
|---|---|
| Pentasodium salt of diethylenetriamine-pentaacetic acid in aqueous solution at 40% | 0.48 g as** |
| C8-C10 alkyl polyglucoside in aqueous solution at 60% | 3.6 g as |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

Dyeing Vehicle (2) pH 9.5:

| | | |
|---|---|---|
| 96° ethyl alcohol | 20.8 g | |
| Pentasodium salt of diethylenetriamine-pentaacetic acid in aqueous solution at 40% | 0.48 g as** | |
| C8-C10 alkyl polyglucoside in aqueous solution at 60% | 3.6 g as | |
| Benzyl alcohol | 2.0 g | |
| Polyethylene glycol containing 8 ethylene oxide units | 3.0 g | |
| $NH_4Cl$ | 4.32 g | |
| Aqueous ammonia containing 20% $NH_3$ | 2.94 g | |

**as = active substance

For colorations under non-lightening conditions (without oxidizing agent), these compositions were applied directly to the hair.

For the colorations under lightening conditions an oxidizing medium was used. In this case, at the time of use, each composition was mixed with an equal weight of 20-volume hydrogen peroxide (6% by weight). A final pH of 7 or 9.5 was obtained.

Each resulting mixture was applied to grey tresses comprising 90% white hair, with a 6:1 bath ratio. After a period of leave-in time for 30 minutes, the tresses were rinsed, washed with a standard shampoo, rinsed again and then dried.

The dyeing results obtained were as follows:

| | pH 7 (without oxidizing agent) | pH 9.5 (without oxidizing agent) | pH 7 (with oxidizing agent) | pH 9.5 (with oxidizing agent) |
|---|---|---|---|---|
| Compound 2 | intense violet | intense violet | Intense violet | intense violet |
| Compound 3 | intense violet | intense violet | Intense violet | intense violet |
| Compound 4 | intense violet | intense violet | Intense violet | intense violet |
| Compound 5 | intense violet | intense violet | Intense violet | intense violet |
| Compound 8 | intense violet | intense violet | Intense violet | intense violet |
| Compound 9 | intense violet | intense violet | Intense violet | intense violet |
| Compound 10 | intense violet | intense violet | Intense violet | intense violet |
| Compound 11 | intense violet | intense violet | Intense violet | intense violet |

The tresses thus colored were subjected to a wash resistance test, which consisted of 12 shampooings (with a standard shampoo) followed by evaluation of the color. After 12 shampooings the tresses were all still intensely colored.

What is claimed is:

1. A symmetrical cationic diazo compound of formula (I), the resonance forms, the acid addition salts and/or solvates thereof:

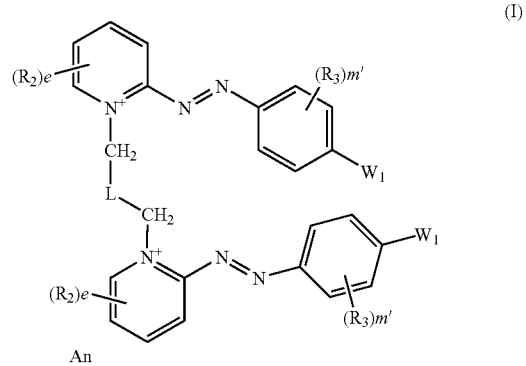

wherein:

the radicals $R_2$, which may be identical or different, are chosen from:
optionally substituted $C_1$-$C_{16}$ alkyl radicals optionally interrupted by at least one heteroatom and/or by at least one group comprising at least one heteroatom, said alkyl radical being further optionally substituted by at least one group chosen from thio (—SH); $C_1$-$C_4$ thioalkyl; $C_1$-$C_4$ alkylsulphinyl and $C_1$-$C_4$ alkylsulphonyl groups;
hydroxyl groups,
$C_1$-$C_4$ alkoxy groups,
$C_2$-$C_4$ (poly)hydroxyalkoxy groups;
alkoxycarbonyl groups (RO—CO—) in which R is chosen from $C_1$-$C_4$ alkyl radicals,
alkylcarbonyloxy radicals (RCO—O—) in which R is chosen from $C_1$-$C_4$ alkyl radicals,
alkylcarbonyl radicals (R—CO—) in which R is chosen from $C_1$-$C_4$ alkyl radicals,
amino groups,
amino groups substituted by one or two identical or different $C_1$-$C_4$ alkyl radicals optionally carrying at least one hydroxyl group, it being possible for the two alkyl radicals optionally to form, with the nitrogen atom to which they are attached, a heterocycle comprising 1 to 3 heteroatoms chosen from N, O and S, and containing 5 to 7 ring members, which is saturated or unsaturated, aromatic or non-aromatic and is optionally substituted;
alkylcarbonylamino groups (RCO—NR'—) in which the radical R is chosen from $C_1$-$C_4$ alkyl radicals, and the radical R' is chosen from hydrogen atoms and $C_1$-$C_4$ alkyl radicals;
aminocarbonyl groups ((R)$_2$N—CO—) in which the radicals R, independently of one another, are chosen from hydrogen atoms and $C_1$-$C_4$ alkyl radicals;
ureido groups (N(R)$_2$—CO—NR'—) in which the radicals R and R', independently of one another, are chosen from hydrogen atoms and $C_1$-$C_4$ alkyl radicals;
aminosulphonyl groups ((R)$_2$N—SO$_2$—) in which the radicals R, independently of one another, are chosen from hydrogen atoms and $C_1$-$C_4$ alkyl radicals;
alkylsulphonylamino groups (RSO$_2$—NR'—) in which R is chosen from $C_1$-$C_4$ alkyl radicals, and R' is chosen from hydrogen atoms and $C_1$-$C_4$ alkyl radicals;
optionally substituted aryl radicals;
optionally substituted ($C_1$-$C_4$)alkylaryl radicals;
alkylsulphinyl groups (R—SO—) in which R is chosen from $C_1$-$C_4$ alkyl radicals;

alkylsulphonyl groups (R—SO$_2$—) in which R is chosen from C$_1$-C$_4$ alkyl radicals;
nitro groups;
cyano groups;
halogen atoms;
thio groups (HS—); and
alkylthio groups (RS—) in which the radical R is chosen from optionally substituted C$_1$-C$_4$ alkyl radicals;
e is an integer ranging from 0 to 4; when e is 2, the two radicals R$_2$ may optionally form, with the carbon atoms to which they are attached, a secondary ring, aromatic or non-aromatic, containing 5 or 6 ring members, which is optionally substituted by at least one identical or different group chosen from hydroxyl groups, C$_1$-C$_4$ alkyl groups, C$_1$-C$_4$ alkoxy groups, C$_2$-C$_4$ (poly)hydroxyalkoxy groups, amino groups, amino groups substituted by one or two identical or different C$_1$-C$_4$ alkyl radicals which optionally carry at least one hydroxyl group;
when e is less than 4, the unsubstituted carbon atom(s) of the heterocycle carry a hydrogen atom,
the radicals R$_3$, which may be identical or different, are chosen from:
  optionally substituted C$_1$-C$_{16}$ alkyl radicals optionally interrupted by at least one entity chosen from heteroatoms and groups comprising at least one heteroatom,
  hydroxyl groups,
  C$_1$-C$_4$ alkoxy groups,
  C$_2$-C$_4$ (poly)hydroxyalkoxy groups;
  alkoxycarbonyl groups (RO—CO—) in which R is chosen from C$_1$-C$_4$ alkyl radicals,
  alkylcarbonyloxy radicals (RCO—O—) in which R is chosen from C$_1$-C$_4$ alkyl radicals;
  alkylcarbonyl radicals (R—CO—) in which R is chosen from C$_1$-C$_4$ alkyl radicals;
  amino groups;
  amino groups substituted by one or two identical or different C$_1$-C$_4$ alkyl radicals optionally carrying at least one hydroxyl group; it being possible for the two alkyl radicals optionally to form, with the nitrogen atom to which they are attached, a heterocycle comprising 1 to 3 heteroatoms chosen from N, O and S, and containing 5 to 7 ring members, which is saturated or unsaturated, aromatic or non-aromatic and is optionally substituted;
  alkylcarbonylamino groups (RCO—NR'—) in which the radical R is chosen from C$_1$-C$_4$ alkyl radicals, and the radical R' is chosen from a hydrogen atom and C$_1$-C$_4$ alkyl radicals;
  aminocarbonyl groups ((R)$_2$N—CO—) in which the radicals R, independently of one another, are chosen from hydrogen atoms and C$_1$-C$_4$ alkyl radicals;
  ureido groups (N(R)$_2$—CO—NR'—) in which the radicals R and R', independently of one another, are chosen from hydrogen atoms and C$_1$-C$_4$ alkyl radicals;
  aminosulphonyl groups ((R)$_2$N—SO$_2$—) in which the radicals R, independently of one another, are chosen from hydrogen atoms and C$_1$-C$_4$ alkyl radical;
  alkylsulphonylamino groups (RSO$_2$—NR'—) in which the radicals R and R', independently of one another, are chosen from hydrogen atoms and C$_1$-C$_4$ alkyl radicals;
  thio groups (HS—);
  alkylthio groups (RS—) in which the radical R is chosen from C$_1$-C$_4$ alkyl radicals;
  alkylsulphinyl groups (R—SO—) in which R is chosen from C$_1$-C$_4$ alkyl radicals;
  alkylsulphonyl groups (R—SO$_2$—) in which R is chosen from C$_1$-C$_4$ alkyl radicals;
  nitro groups;
  cyano groups; and
  halogen atoms;
m' is an integer ranging from 0 to 4; when m' is greater than or equal to 2, two adjacent radicals R$_3$ may form, with the carbon atoms to which they are attached, a secondary ring, aromatic or non-aromatic, containing 6 ring members, which is optionally substituted by at least one identical or different group chosen from: hydroxyl groups, C$_1$-C$_4$ alkyl groups, C$_1$-C$_4$ alkoxy groups, C$_2$-C$_4$ (poly)hydroxyalkoxy groups, C$_1$-C$_4$ alkylcarbonylamino groups, amino groups, amino groups substituted by one or two identical or different C$_1$-C$_4$ alkyl radicals which optionally carry at least one hydroxyl group,
when m' is less than 4, then the unsubstituted carbon atom(s) of the aromatic ring carry a hydrogen atom;
W$_1$ radicals, which are identical, are chosen from:
  hydrogen atoms,
  halogen atoms chosen from bromine, chlorine and fluorine, and
  —NR$_5$R$_6$, OR$_7$, —NR$_4$—Ph—NR$_5$R$_6$, —NR$_4$—Ph—OR$_7$, —O—Ph—OR$_7$ and —O—Ph—NR$_5$R$_6$ groups,
wherein:
  R$_4$ and R$_7$, which may be identical or different, are chosen from hydrogen atoms, optionally substituted C$_1$-C$_{20}$ alkyl radicals, optionally substituted C$_1$-C$_3$ aralkyl radicals, and optionally substituted phenyl radicals;
  R$_5$ and R$_6$, which may be identical or different, are chosen from hydrogen atoms, optionally substituted C$_1$-C$_{20}$ alkyl radicals, optionally substituted phenyl radicals, optionally substituted C$_1$-C$_3$ aralkyl radicals, and alkylcarbonyl radicals (R—CO—) in which R is chosen from C$_1$-C$_4$ alkyl radicals; and
  R$_5$ and R$_6$ may optionally form, with the nitrogen atom to which they are attached, a heterocycle comprising 1 to 3 heteroatoms, chosen from N, O and S, and containing 5 to 7 ring members, which is saturated or unsaturated, aromatic or non-aromatic and is optionally substituted; or
  R$_5$ and R$_6$ may optionally form, with the carbon atom of the aromatic ring adjacent to that to which —NR$_5$R$_6$ is attached, a 5- or 6-membered saturated heterocycle;
  Ph is chosen from optionally substituted phenyl radicals;
  L is a cationic or non-cationic linker;
wherein the electroneutrality of the compound of formula (I) is ensured by at least one cosmetically acceptable anion (An).

2. The compound according to claim 1, wherein when R$_2$ and/or R$_3$ is chosen from optionally substituted C$_1$-C$_{16}$ alkyl radicals optionally interrupted by at least one heteroatom and/or at least one group containing at least one heteroatom, wherein said heteroatoms and said groups are chosen from oxygen, nitrogen, sulphur, —CO—, SO$_2$—, and combinations thereof.

3. The compound according to claim 1, wherein the radicals R$_2$, which may be identical or different, are chosen from:
  halogen atoms chosen from chlorine and fluorine;
  C$_1$-C$_4$ alkyl radicals optionally substituted by at least one identical or different radical chosen from hydroxyl, C$_1$-C$_2$ alkoxy, C$_2$-C$_4$ (poly)hydroxyalkoxy, amino, C$_1$-C$_2$ (di)alkylamino, thio (—SH), C$_1$-C$_4$ alkylsulphinyl, C$_1$-C$_4$ alkylsulphonyl and C$_1$-C$_4$ thioalkyl radicals;

phenyl radicals optionally substituted by at least one identical or different radical chosen from hydroxyl, $C_1$-$C_2$ alkoxy, $C_2$-$C_4$ (poly)hydroxyalkoxy, amino and $C_1$-$C_2$ (di)alkylamino radicals, and halogen atoms;

$C_1$-$C_4$ alkoxy radicals;

$C_1$-$C_4$ alkylsulphonylamino radicals;

$C_2$-$C_4$ (poly)hydroxyalkoxy radicals;

amino radicals;

$C_1$-$C_2$ (di)alkylamino radicals;

$C_2$-$C_4$ (poly)hydroxyalkylamino radicals;

alkylsulphonylamino radicals ($RSO_2N$—) in which the radical R is chosen from $C_1$-$C_4$ alkyl radicals;

aminosulphonyl radicals (($R)_2NSO_2$—) in which the radicals R, independently of one another, are chosen from hydrogen atoms and $C_1$-$C_4$ alkyl radicals;

alkylthio radicals (RS—) in which the radical R is chosen from $C_1$-$C_4$ alkyl radicals;

alkylsulphinyl radicals (RSO—) in which the radical R is chosen from $C_1$-$C_4$ alkyl radicals;

alkylsulphonyl radicals (R—$SO_2$—) in which the radical R is chosen from $C_1$-$C_4$ alkyl radicals;

alkylcarbonylamino radicals (RCONR'—) in which the radical R is chosen from a hydrogen atom and $C_1$-$C_4$ alkyl radicals, and the radical R' is chosen from a hydrogen atom and $C_1$-$C_4$ alkyl radicals.

4. The compound according to claim 1, wherein the two radicals $R_2$ may optionally form, with the carbon atoms to which they are attached, a secondary, 6-membered aromatic ring optionally substituted by at least one identical or different group chosen from hydroxyl groups, $C_1$-$C_4$ alkyl groups, $C_1$-$C_4$ alkoxy groups, amino groups, and amino groups substituted by one or two identical or different $C_1$-$C_4$ alkyl radicals which optionally carry at least one hydroxyl or methylcarbonylamino group.

5. The compound according to claim 1, wherein the radicals $R_3$, which may be identical or different, are chosen from:

optionally substituted $C_1$-$C_{16}$ alkyl radicals;

halogen atoms;

hydroxyl groups;

$C_1$-$C_2$ alkoxy radicals;

$C_2$-$C_4$ (poly)hydroxyalkoxy radicals;

amino radicals;

amino radicals substituted by one or two identical or different $C_1$-$C_4$ alkyl radicals which are optionally substituted by at least one identical or different group chosen from hydroxyl and $C_1$-$C_4$ alkoxy groups, it being possible for the two alkyl radicals to form, with the nitrogen atom to which they are attached, a heterocycle comprising 1 to 3 heteroatoms, chosen from N, O and S, the heterocycle containing 5 to 7 ring members, being saturated or unsaturated, aromatic or non-aromatic, and being optionally substituted;

alkylcarbonylamino radicals (RCO—NR'—) in which the radical R is chosen from $C_1$-$C_4$ alkyl radicals, and the radical R' is chosen from a hydrogen atom and $C_1$-$C_4$ alkyl radicals;

alkylsulphonylamino radicals (R'$SO_2$—NR—) in which the radical R is chosen from a hydrogen atom and $C_1$-$C_4$ alkyl radicals, and the radical R' is chosen from $C_1$-$C_4$ alkyl radicals;

aminosulphonyl radicals (($R)_2N$—$SO_2$—) in which the radicals R, which may be identical or different, are chosen from hydrogen atoms and $C_1$-$C_4$ alkyl radicals;

alkylthio radicals (RS—) in which the radical R is chosen from $C_1$-$C_4$ alkyl radicals; and alkylsulphonyl radicals (R—$SO_2$—) in which the radical R is chosen from $C_1$-$C_4$ alkyl radicals.

6. The compound according to claim 1, wherein the radicals $R_3$, which may be identical or different, are chosen from:

$C_1$-$C_4$ alkyl radicals which are optionally substituted by at least one identical or different radical chosen from hydroxyl radicals, $C_1$-$C_2$ alkylcarbonylamino radicals, amino radicals substituted by one or two identical or different $C_1$-$C_2$ alkyl radicals which optionally carry at least one entity chosen from hydroxyl groups and $C_1$-$C_2$ alkoxy radicals, it being possible for these two alkyl radicals optionally to form, with the nitrogen atom to which they are attached, a 5- or 6-membered heterocycle which is saturated or unsaturated and is optionally aromatic;

$C_2$-$C_4$ hydroxyalkoxy radicals;

halogens chosen from chlorine and fluorine;

amino radicals;

amino radicals substituted by one or two identical or different $C_1$-$C_2$ alkyl radicals which optionally carry at least one hydroxyl group;

methylcarbonylamino radicals;

methylsulphonylamino radicals;

hydroxyl radicals;

$C_1$-$C_2$ alkoxy radicals; and methylsulphonyl radicals.

7. The compound according to claim 6, wherein when $R_3$ is chosen from $C_1$-$C_4$ alkyl radicals substituted by amino radicals substituted by two identical or different $C_1$-$C_2$ alkyl radicals and wherein when the two alkyl radicals optionally form, with the nitrogen atom to which they are attached, a 5- or 6-membered saturated or unsaturated and optionally aromatic heterocycle, wherein said heterocycle is chosen from pyrrolidine, piperazine, homopiperazine, pyrrole, imidazole and pyrazole.

8. The compound according to claim 1, wherein, when the coefficient m' is greater than or equal to 2, two adjacent radicals $R_3$ may form, with the carbon atoms to which they are attached, a secondary, 6-membered aromatic ring optionally substituted by at least one group chosen from hydroxyl groups, —$NR_4$—Ph groups, —$NR_4$—Ph—$NR_5R_6$ groups, —$NR_4$—Ph—$OR_7$ groups, $C_1$-$C_4$ alkyl groups, $C_1$-$C_4$ alkoxy groups, $C_2$-$C_4$ (poly)hydroxyalkoxy groups, $C_1$-$C_4$ alkylcarbonylamino groups, amino groups, and amino groups substituted by one or two identical or different $C_1$-$C_4$ alkyl radicals which optionally carry at least one hydroxyl group.

9. The compound according to claim 1, wherein two adjacent radicals $R_3$ may form, with the carbon atoms to which they are attached, a secondary, 6-membered aromatic ring which is optionally substituted by at least one group chosen from hydroxyl groups, methoxy groups, ethoxy groups, 2-hydroxyethyloxy groups, amino groups, methylcarbonylamino groups, (di)-2-hydroxyethylamino groups, —NH—Ph groups, —NH—Ph—$NH_2$ groups, —NH—Ph—$NHCOCH_3$ groups, —NH—Ph—OH groups, and —NH—Ph—$OCH_3$ groups.

10. The compound according to claim 1, wherein $R_4$ and $R_7$, independently of one another, are chosen from:

hydrogen atoms;

$C_1$-$C_6$ alkyl radicals which are optionally substituted;

aryl and arylalkyl radicals, the aryl moiety being optionally substituted.

11. The compound according to claim 10, wherein when $R_4$ and $R_7$ independently of one another are chosen from an aryl or arylalkyl radical, the aryl moiety is optionally substituted by at least one identical or different group chosen from a chlorine atom, an amino group, a hydroxyl group, a $C_1$-$C_2$ alkoxy group and an amino group which is mono- or disubstituted by two identical or different $C_1$-$C_4$ alkyl radicals which optionally carry at least one hydroxyl group.

12. The compounds according to claim 1, wherein the radicals $R_5$ and $R_6$, which may be identical or different, are chosen from:

hydrogen atoms;
alkylcarbonyl radicals (R—CO—) in which R is chosen from optionally substituted $C_1$-$C_4$ alkyl radicals;
$C_1$-$C_6$ alkyl radicals which are optionally substituted the alkyl radical may further be substituted by at least one group chosen from $C_1$-$C_4$ alkylsulphonyl, $C_1$-$C_4$ alkylsulphinyl and $C_1$-$C_4$ alkylcarbonyl groups;
aryl and arylalkyl radicals, the aryl moiety being optionally substituted by at least one group chosen from chlorine, amino groups, hydroxyl groups, $C_1$-$C_4$ alkoxy groups, and amino groups which are mono- or disubstituted by one or two identical or different $C_1$-$C_4$ alkyl radicals which optionally carry at least one hydroxyl group.

13. The compound according to claim 12, wherein when $R_5$ and $R_6$ independently of one another, are chosen from $C_1$-$C_6$ alkyl radicals, wherein said $C_1$-$C_6$ alkyl radicals are optionally substituted by at least one group chosen from hydroxyl, $C_1$-$C_2$ alkoxy, amino, and $C_1$-$C_4$ (di)alkylamino groups.

14. The compound according to claim 1, wherein the radicals $R_5$ and $R_6$, which may be identical or different, are chosen from:

hydrogen atoms;
methylcarbonyl, ethylcarbonyl and propylcarbonyl radicals;
optionally substituted $C_1$-$C_3$ alkyl radicals;
phenyl radicals which are optionally substituted by at least one radical chosen from hydroxyl radicals, $C_1$-$C_2$ alkoxy radicals, amino radicals, amino radicals substituted by at least one $C_1$-$C_4$ alkyl groups which optionally carry at least one hydroxyl group.

15. The compound according to claim 14, wherein when the radicals $R_5$ and $R_6$, which may be identical or different, are chosen from optionally substituted $C_1$-$C_3$ alkyl radicals, wherein said radicals are chosen from methyl, ethyl, 2-hydroxyethyl and 2-methoxyethyl radicals.

16. The compound according to claim 1, wherein the radicals $R_5$ and $R_6$ form, together with the nitrogen atom to which each is attached, a heterocycle comprising 1 to 3 heteroatoms, chosen from N, O and S, and containing 5 to 7 ring members, which is saturated or unsaturated, aromatic or non-aromatic, and is optionally substituted.

17. The compound according to claim 16, wherein the heterocycle containing 5 to 7 ring members is chosen from the following heterocycles: piperidine, 2-(2-hydroxyethylpiperidine), 4-(aminomethyl)piperidine, 4-(2-hydroxyethyl)piperidine, 4-(dimethylamino)piperidine, piperazine, 1-methylpiperazine, 1-(2-hydroxyethyl)piperazine, 1-(2-aminoethyl)piperazine, 1-hydroxyethylethoxypiperazine, homopiperazine, 1-methyl-1,4-perhydrodiazepine, pyrrole, and 1,4-dimethylpyrrole.

18. The compound according to claim 1, wherein the radicals $R_5$ and $R_6$ are chosen from alkyl radicals which, independently of one another, form, with the carbon atom of the aromatic ring optionally substituted by a hydroxyl and adjacent to that to which —$NR_5R_6$ is attached, a 5- or 6-membered saturated heterocycle.

19. The compound according to claim 1, wherein L is a non-cationic linker and is chosen from:

a covalent bond;
optionally substituted $C_1$-$C_{40}$ alkyl radicals optionally interrupted by a saturated or unsaturated, aromatic or non-aromatic (hetero)cycle comprising 3 to 7 ring members which is optionally substituted and optionally fused, said alkyl radical being optionally interrupted by at least one heteroatom and/or by at least one group comprising at least one heteroatom, with the proviso that the linker L does not contain an azo, nitro, nitroso or peroxo bond; and
optionally substituted phenyl radicals.

20. The compound according to claim 19, wherein when L is chosen from an optionally substituted $C_1$-$C_{40}$ alkyl radical optionally interrupted by at least one heteroatom or by at least one group comprising at least one heteroatom, wherein said heteroatoms and groups are chosen from oxygen, nitrogen, sulphur, —CO—, $SO_2$—, and combinations thereof.

21. The compound according to claim 1, wherein L is a cationic linker chosen from $C_2$-$C_{40}$ alkyl radicals which carry at least one cationic charge and are optionally substituted and/or optionally interrupted by at least one saturated or unsaturated, aromatic or non-aromatic, identical or different (hetero)cycles comprising 3 to 7 ring members and/or optionally interrupted by at least one heteroatom and/or at least one group comprising at least one heteroatom, with the proviso that the linker L does not contain an azo, nitro, nitroso or peroxo bond; and wherein the linker L carries at least one cationic charge.

22. The compound according to claim 21, wherein when L is chosen from an optionally substituted $C_2$-$C_{40}$ alkyl radical optionally interrupted by at least one heteroatom or by at least one group comprising at least one heteroatom, wherein said heteroatoms and groups are chosen from oxygen, nitrogen, sulphur, —CO—, $SO_2$—, and combinations thereof.

23. The compound according to claim 1, wherein An is chosen from organic and inorganic anions, or anion mixture, allowing the charge or charges on the compounds of formula (I) to be balanced.

24. The compound according to claim 23, wherein the at least one An is chosen from halides; hydroxides; sulphates; hydrogensulphates; alkylsulphate for which the linear or branched alkyl moiety is $C_1$-$C_6$; carbonates and hydrogencarbonates; salts of carboxylic acids; alkylsulphonates for which the linear or branched alkyl moiety is $C_1$-$C_6$; arylsulphonates for which the aryl moiety is optionally substituted by at least one $C_1$-$C_4$ alkyl radical; and alkylsulphonyls.

25. The compound according to claim 24, wherein in the definition of An, the halides are chosen from chloride, bromide, fluoride, and iodide, the alkylsulphates wherein the linear or branched alkyl moiety is $C_1$-$C_6$ are chosen from a methylsulphate ion and an ethylsulphate ion;

the salts of carboxylic acids are chosen from formate, acetate, citrate, tartrate, and oxalate;

the alkylsulphonates wherein the linear or branched alkyl moiety is $C_1$-$C_6$ are methylsulphonate ions;

the aryl moiety of the arylsulphonates is phenyl and is optionally substituted by at least one $C_1$-$C_4$ alkyl radical; and/or the alkylsulphonyls are chosen from mesylate.

26. The compound according to claim 1, wherein the compound is chosen from those of formulae (I'), (I") and (I'"') below, and also the resonance forms and/or acid addition salts and/or solvates thereof:

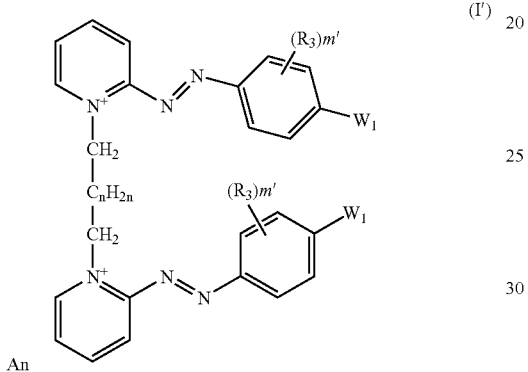

(I')

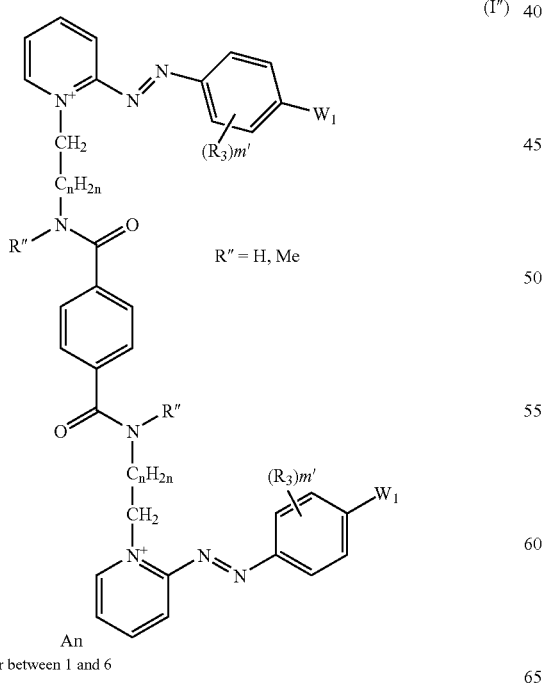

(I")

n = integer between 1 and 6

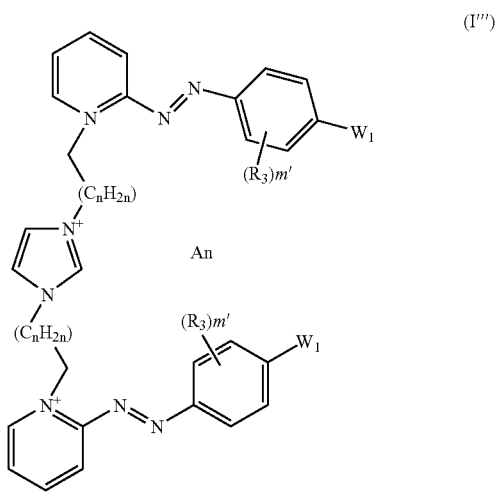

(I'")

n = integer between 1 and 5 wherein the radicals $R_3$, m', n, R" and $W_1$ are as defined in claim 1.

27. The compound according to claim 1, wherein the compound is chosen from the following formulae, the addition salts with an acid, and the solvates thereof:

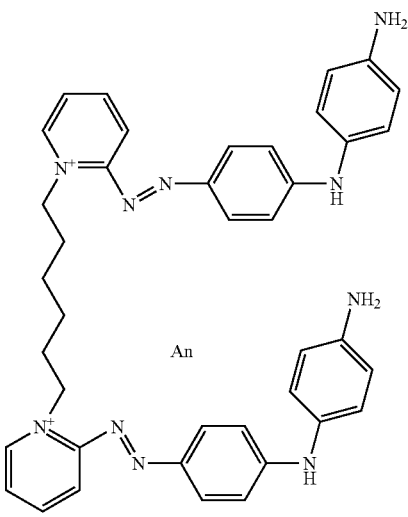

-continued
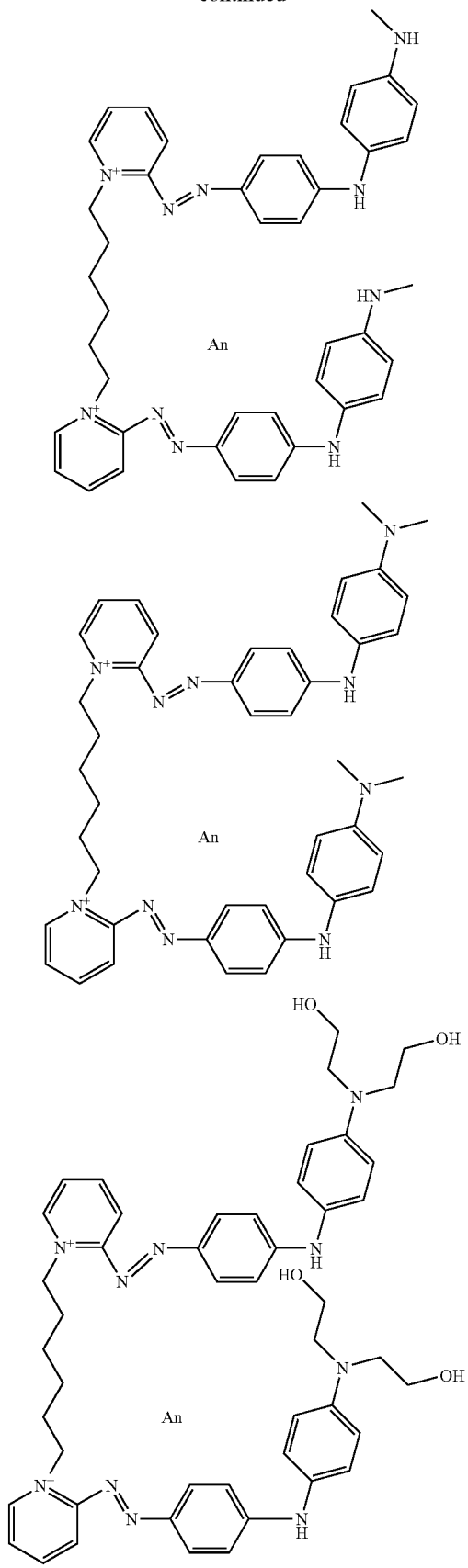
-continued

-continued
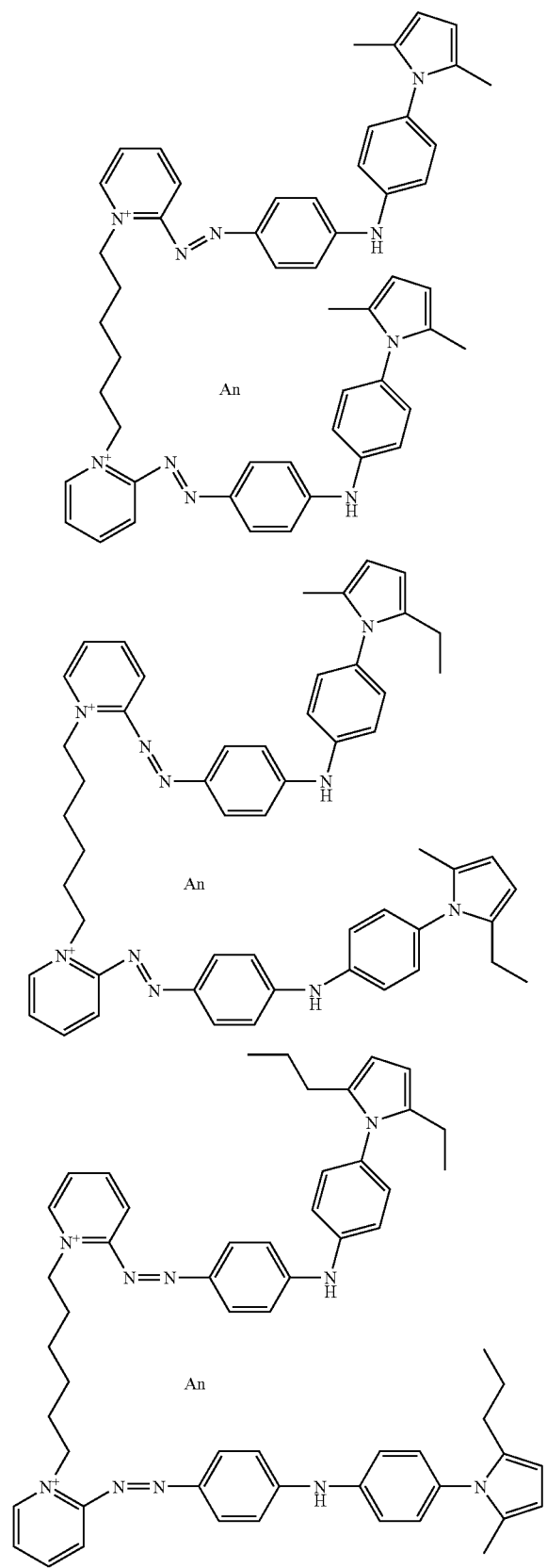
-continued
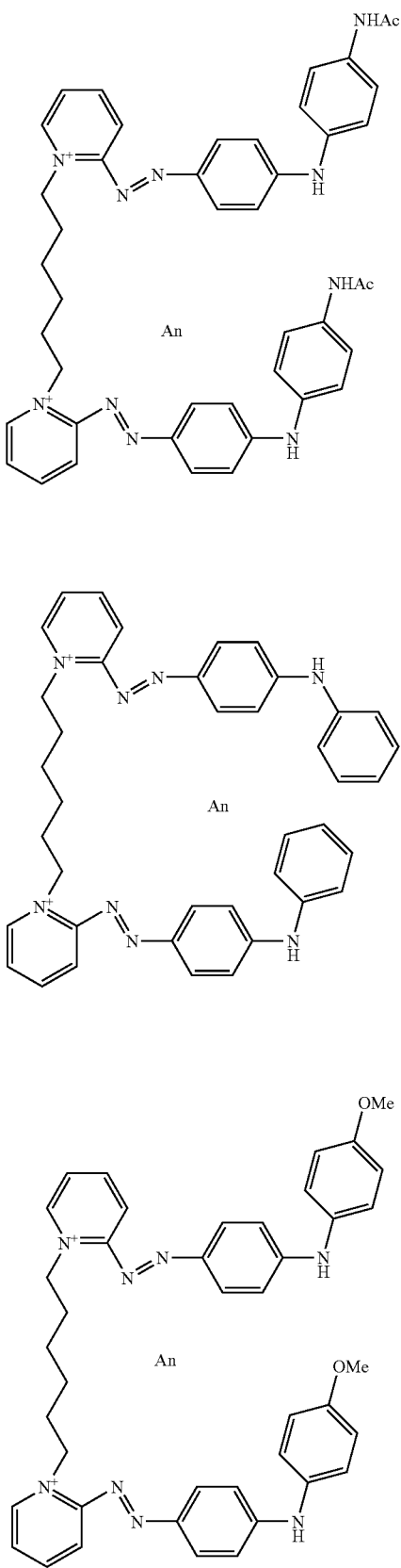

-continued
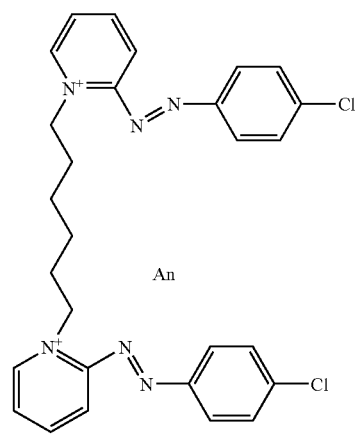
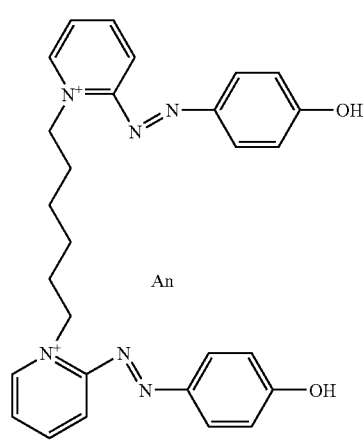
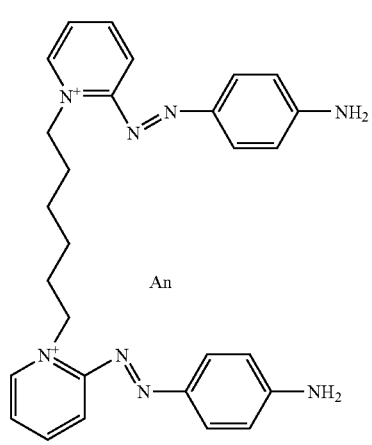
-continued
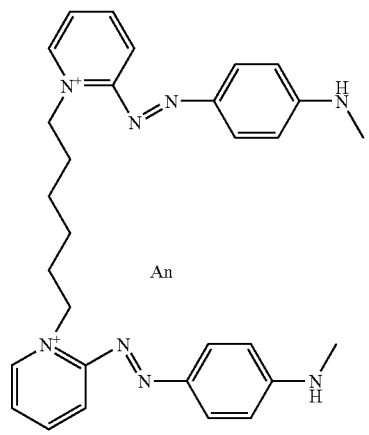
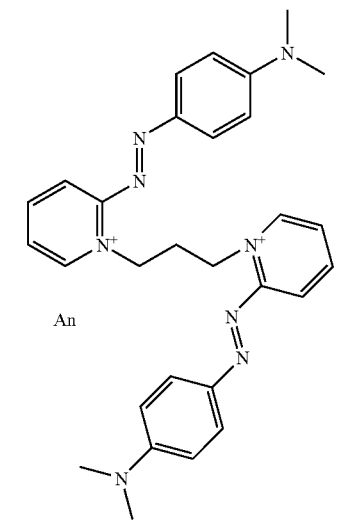
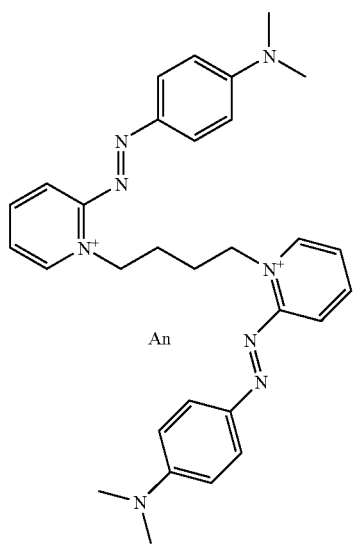

-continued
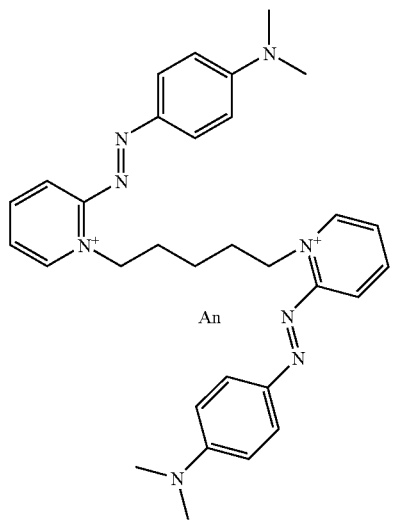
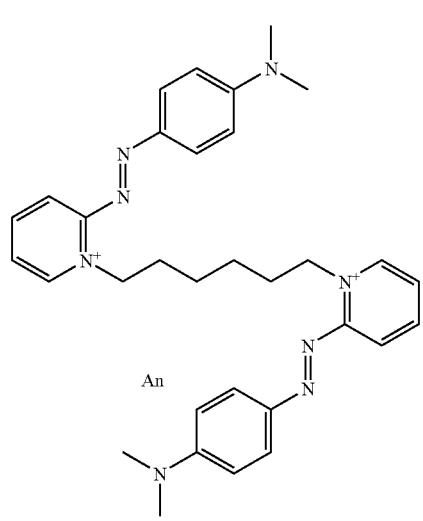
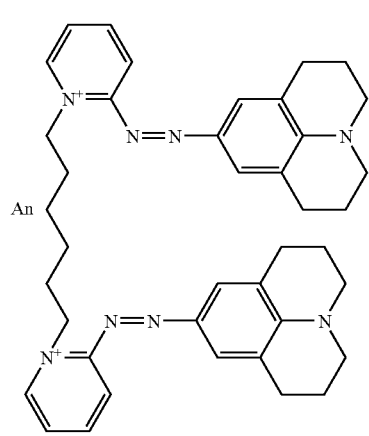
-continued
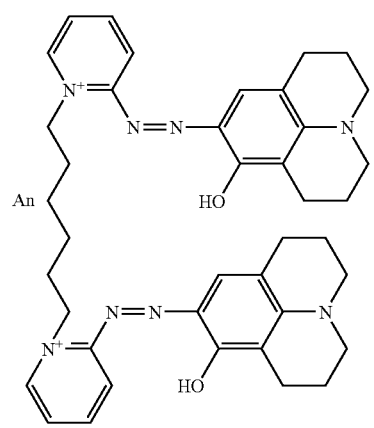
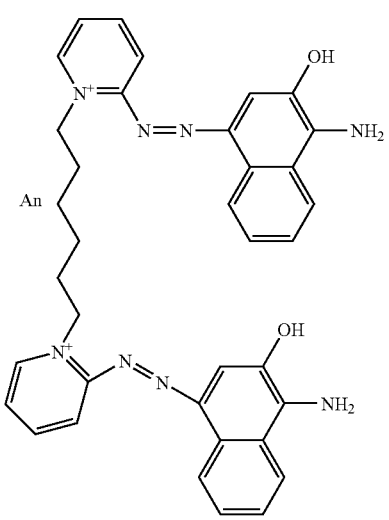
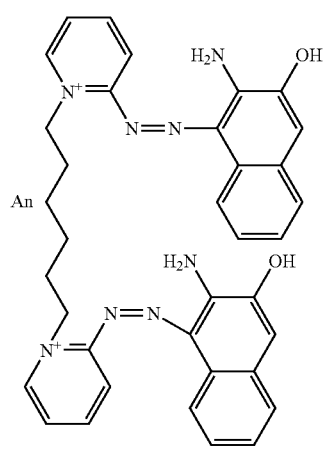

-continued
87
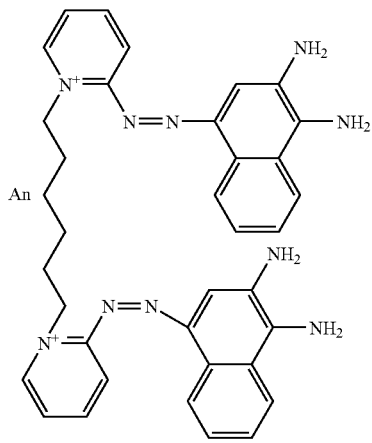
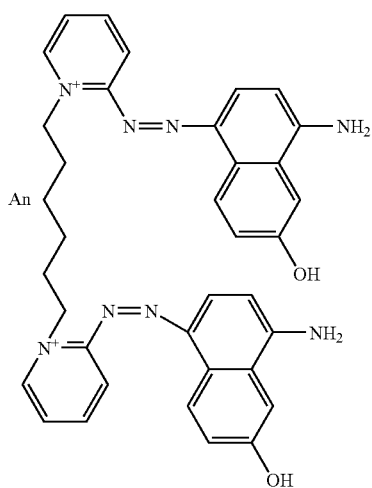
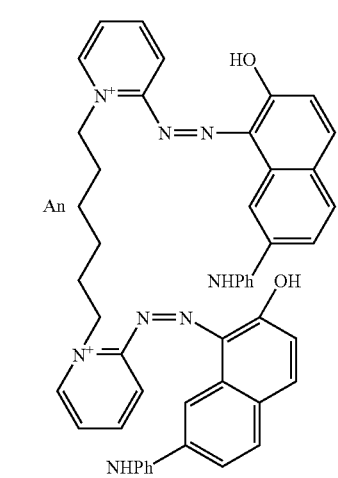
-continued
88
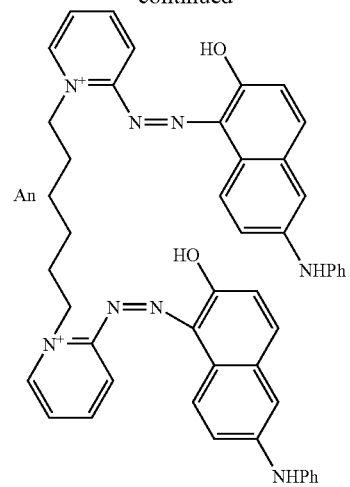
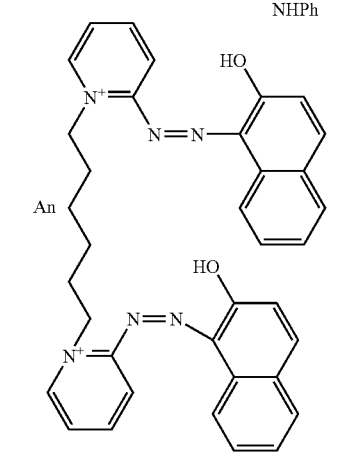
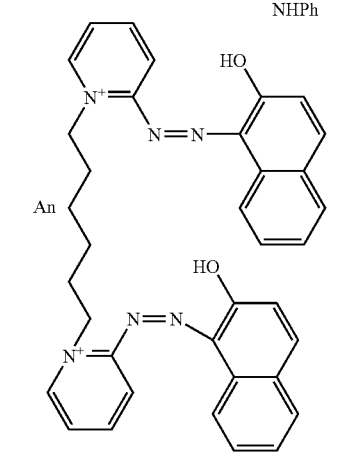
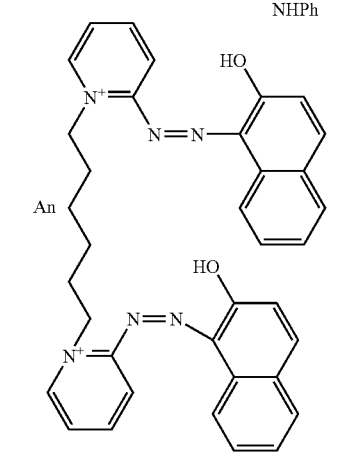

-continued
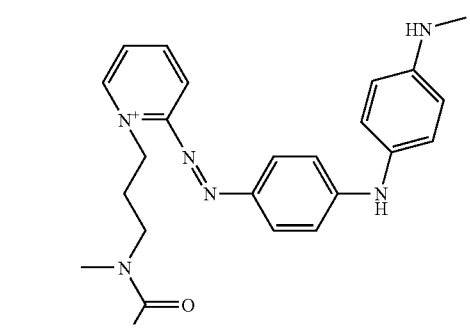
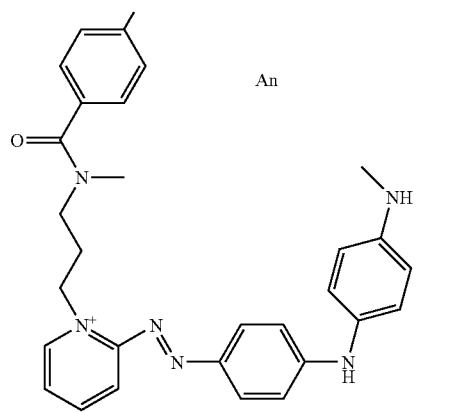
An
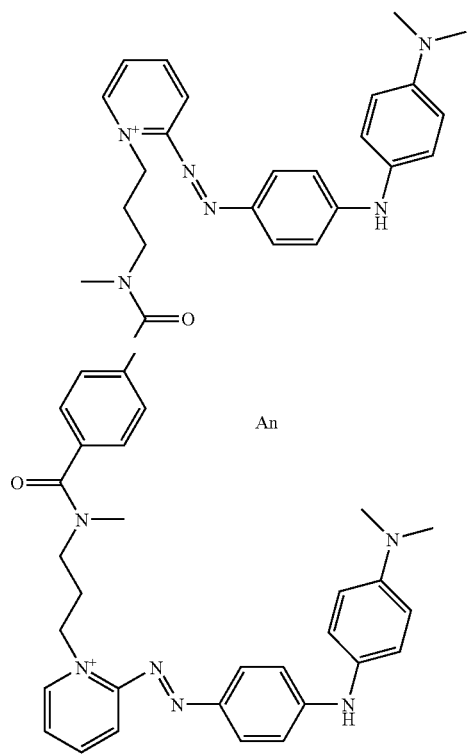
An
-continued
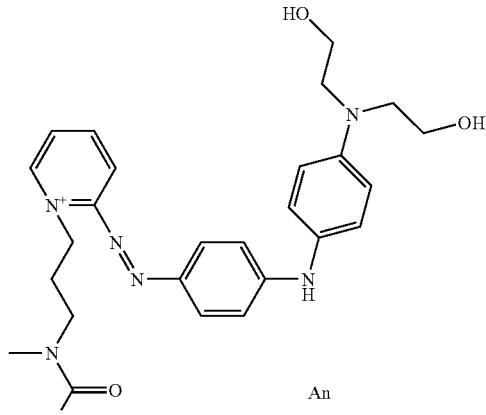
An
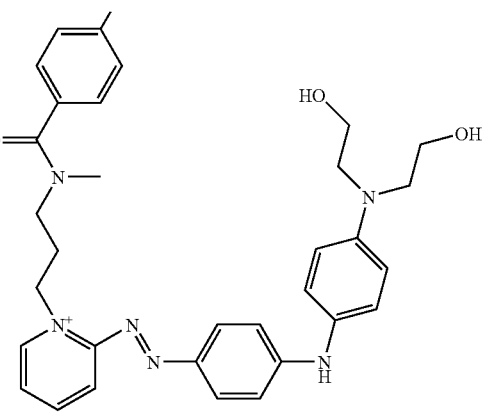
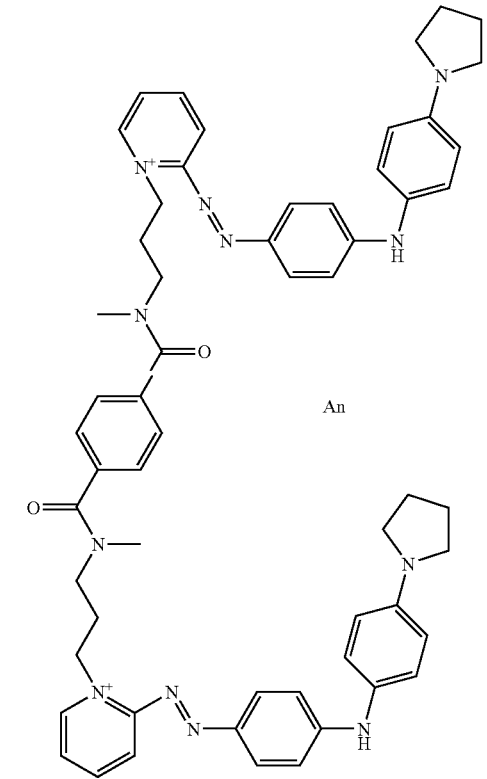
An 91
-continued
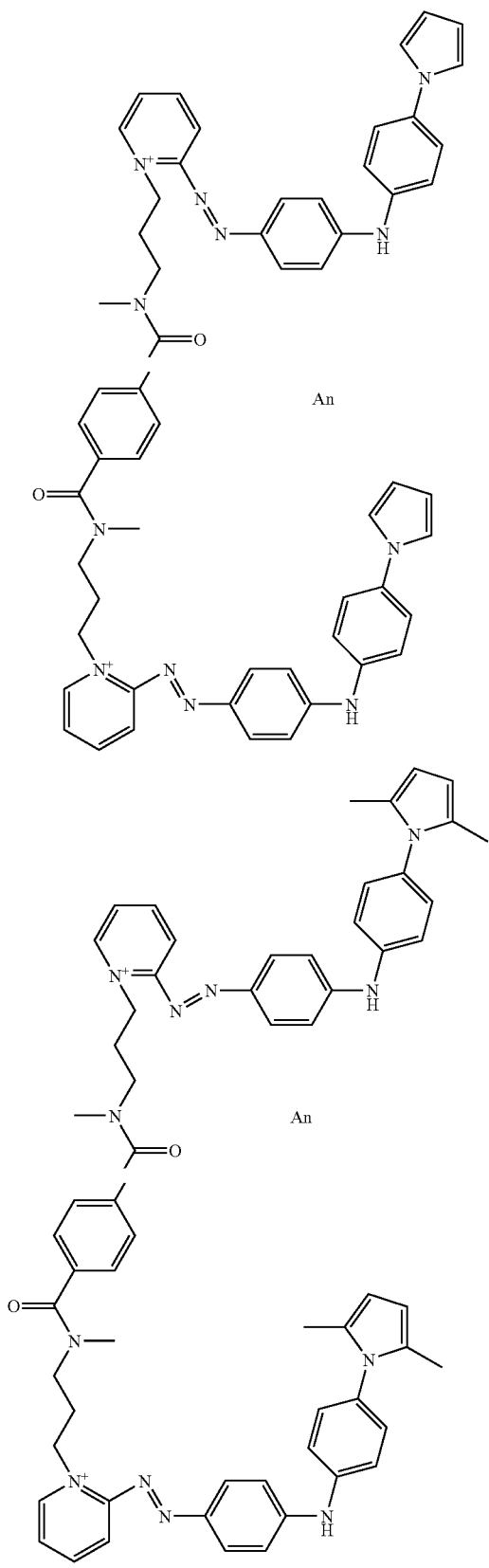
92
-continued
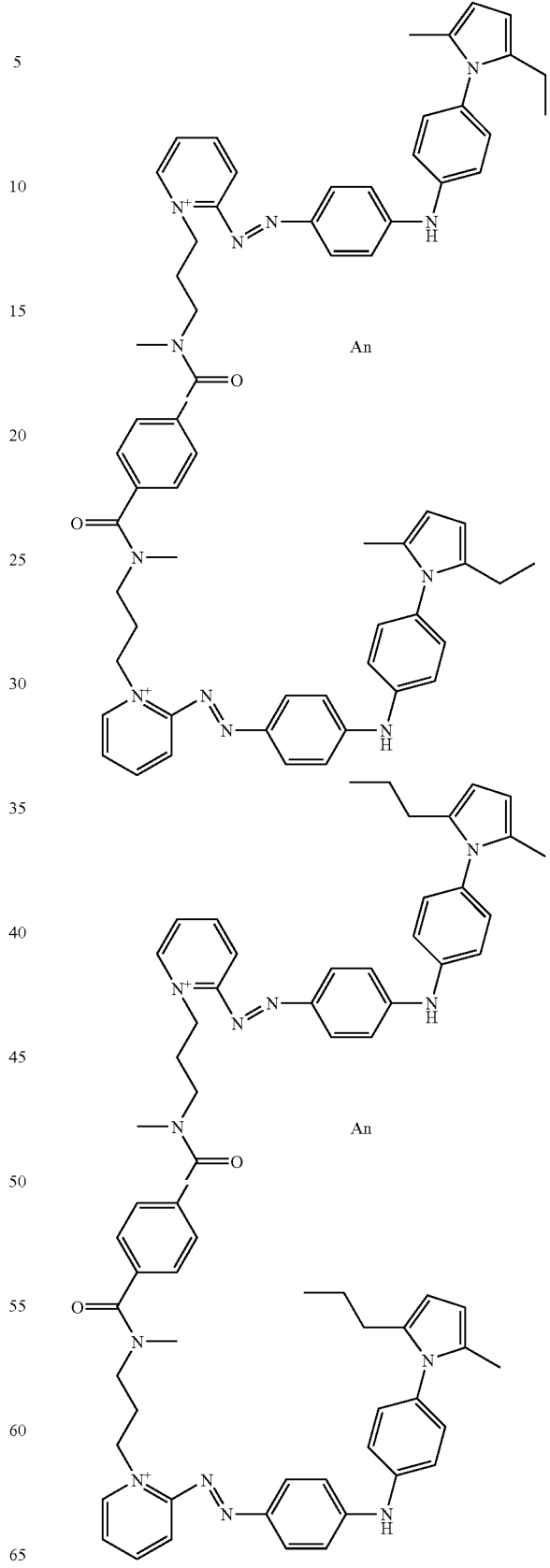

93
-continued
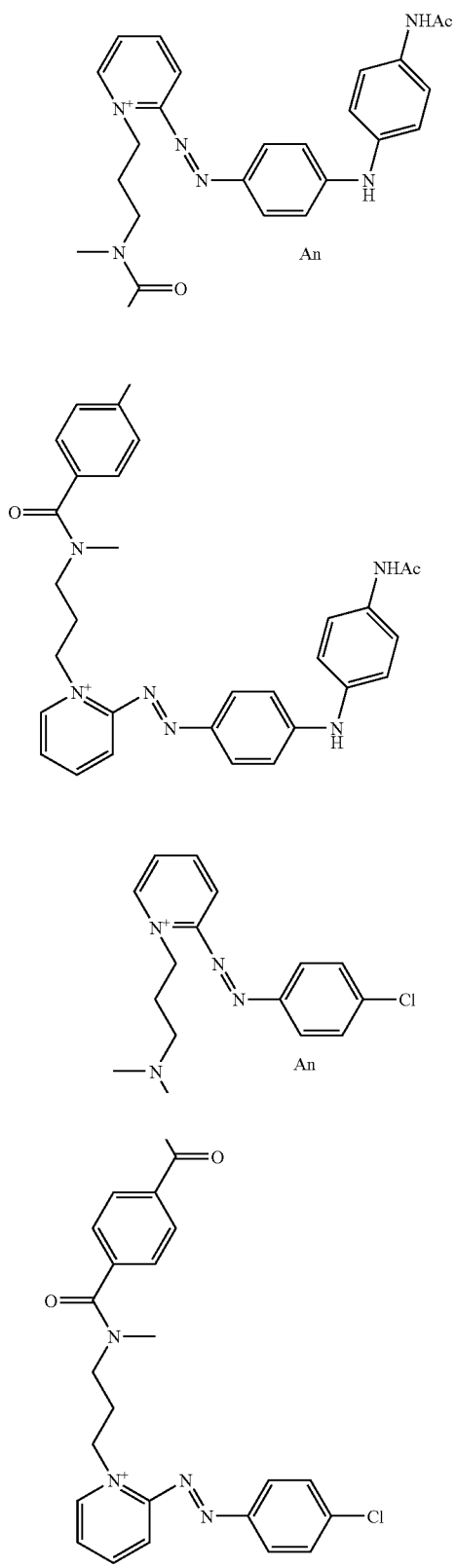
94
-continued
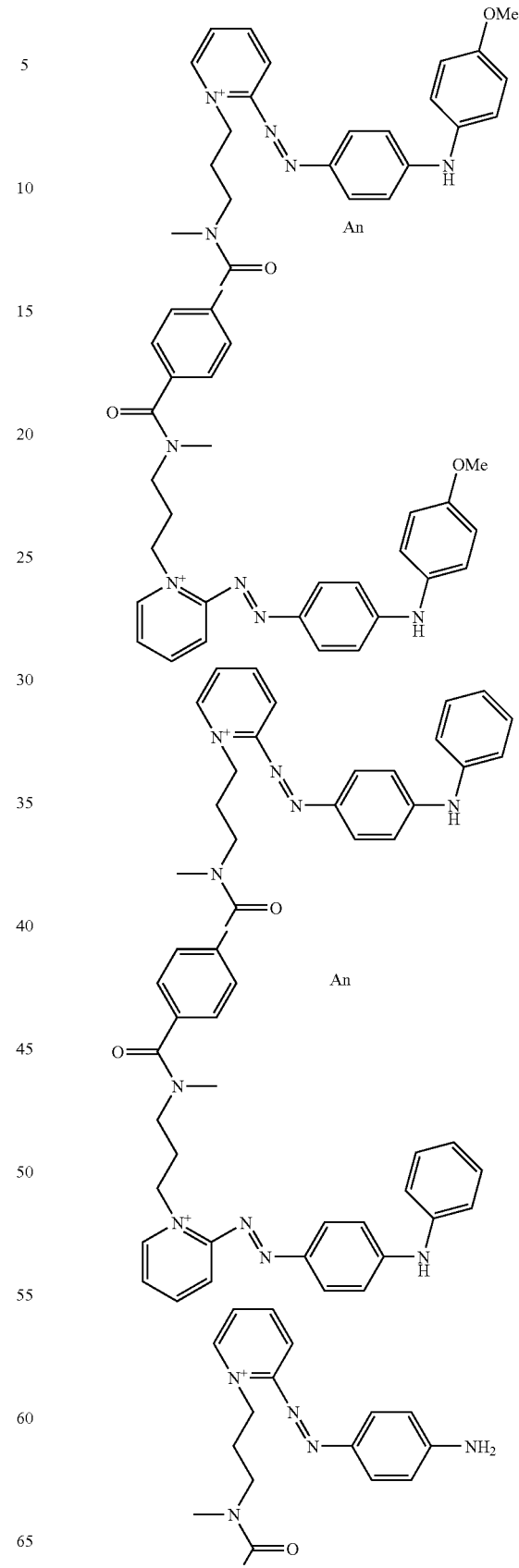

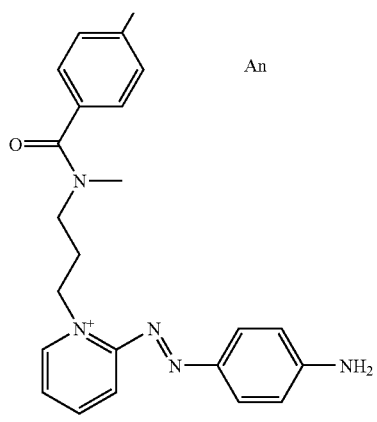
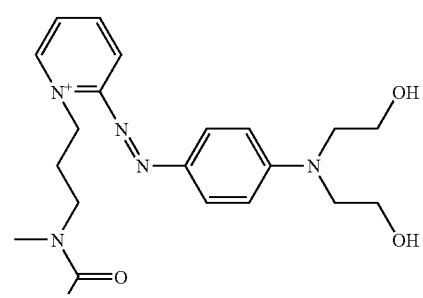
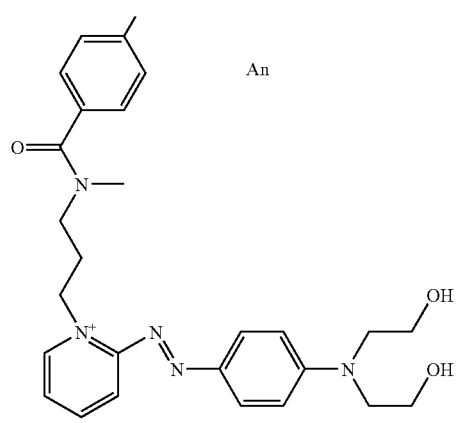
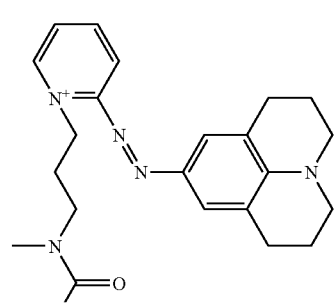
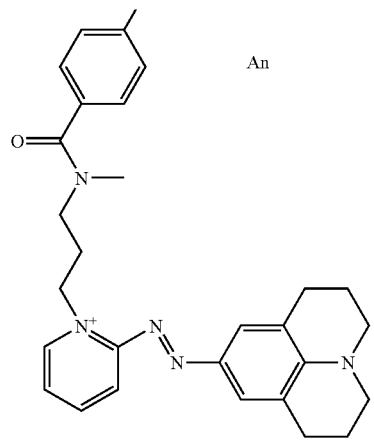
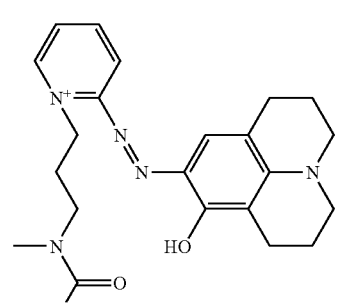
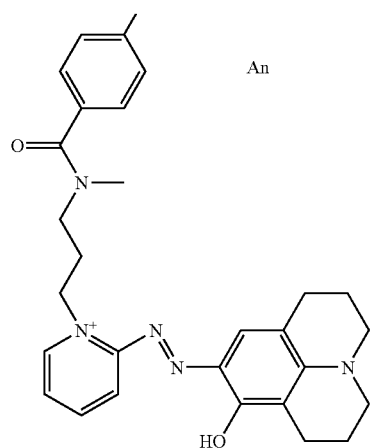
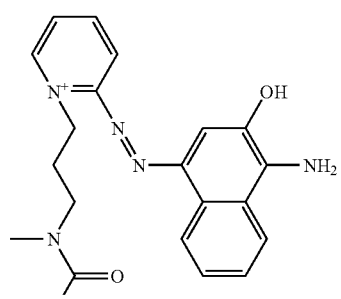

-continued
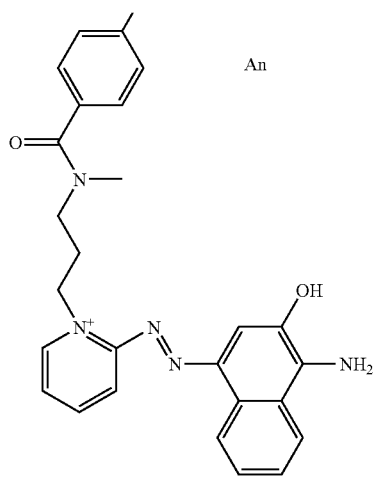
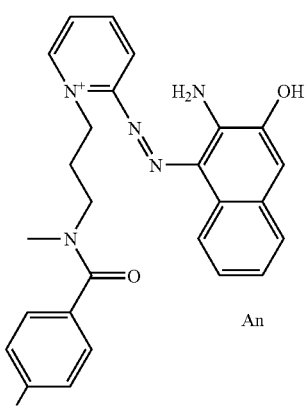
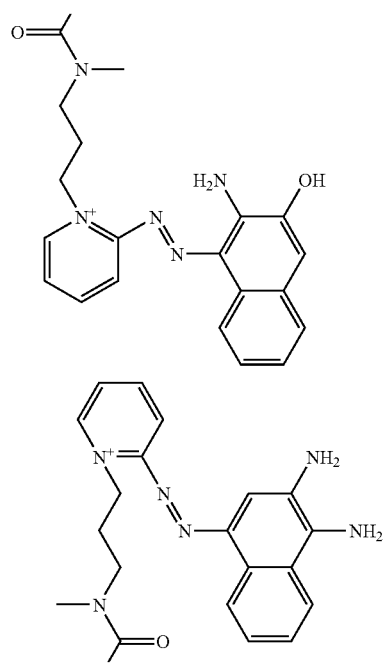
-continued
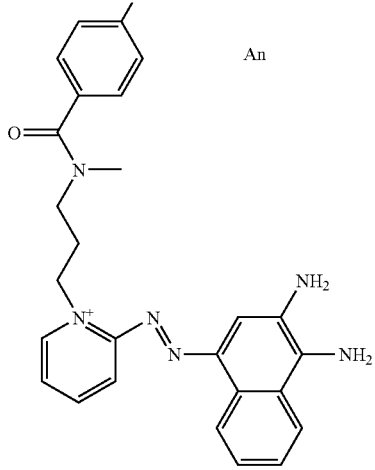
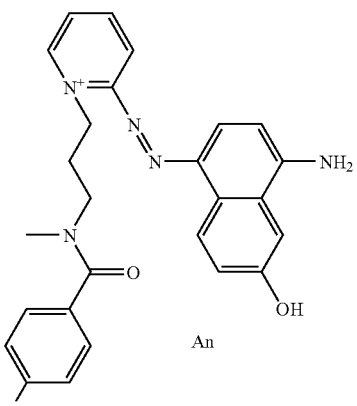
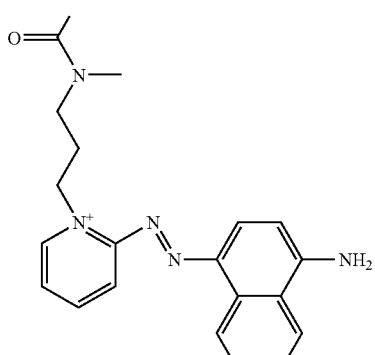
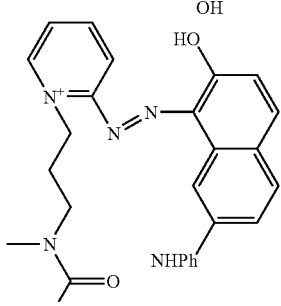

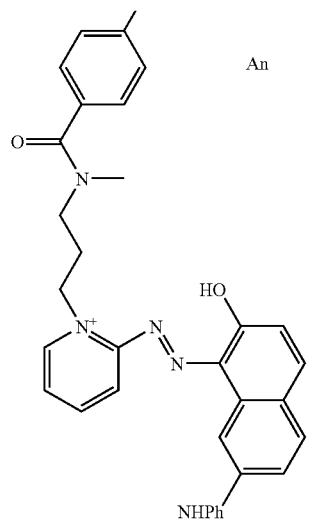
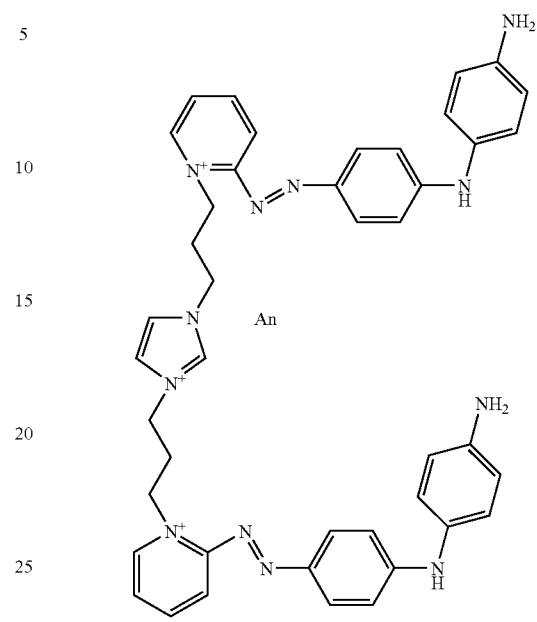
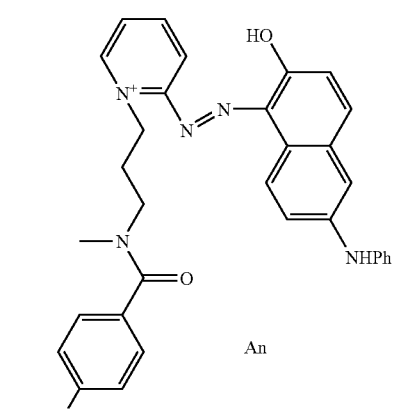
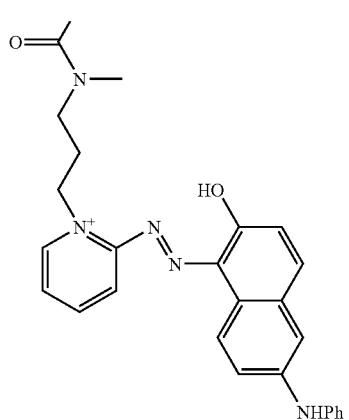
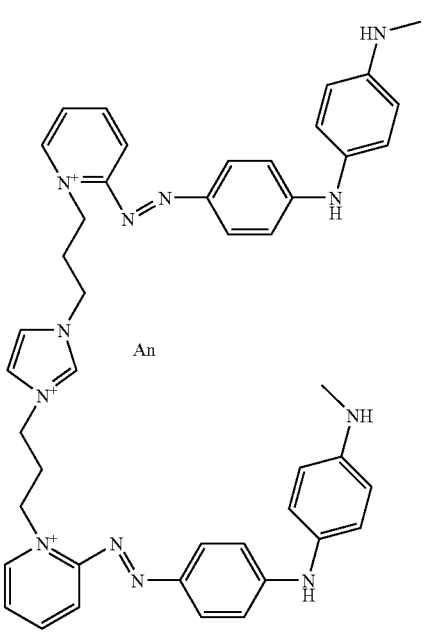

-continued
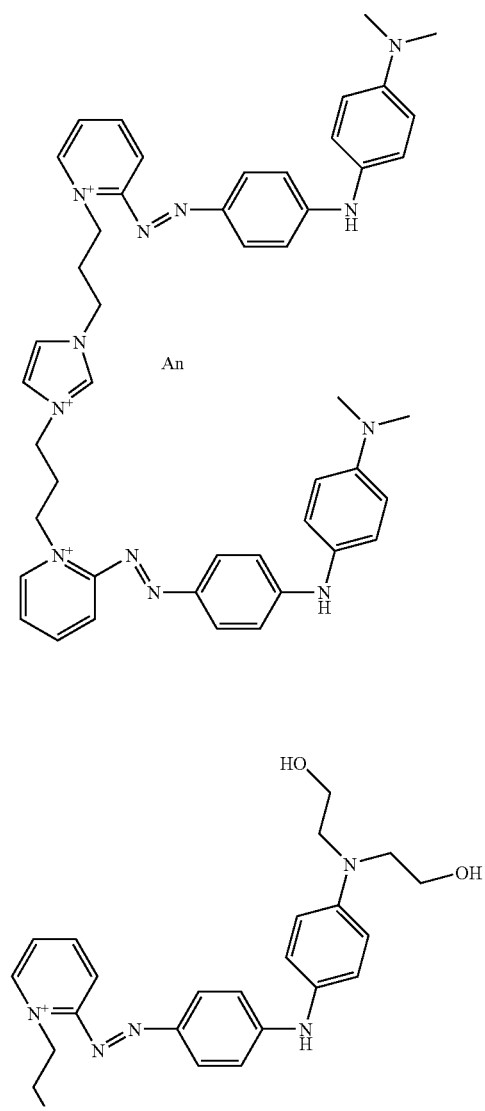
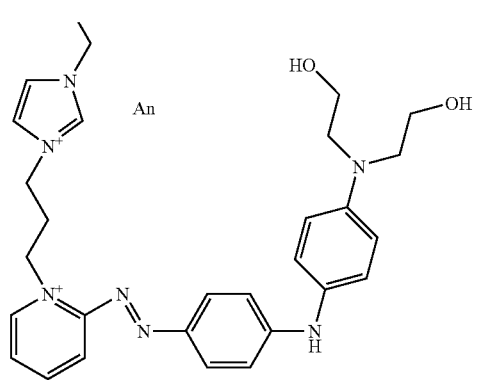
-continued
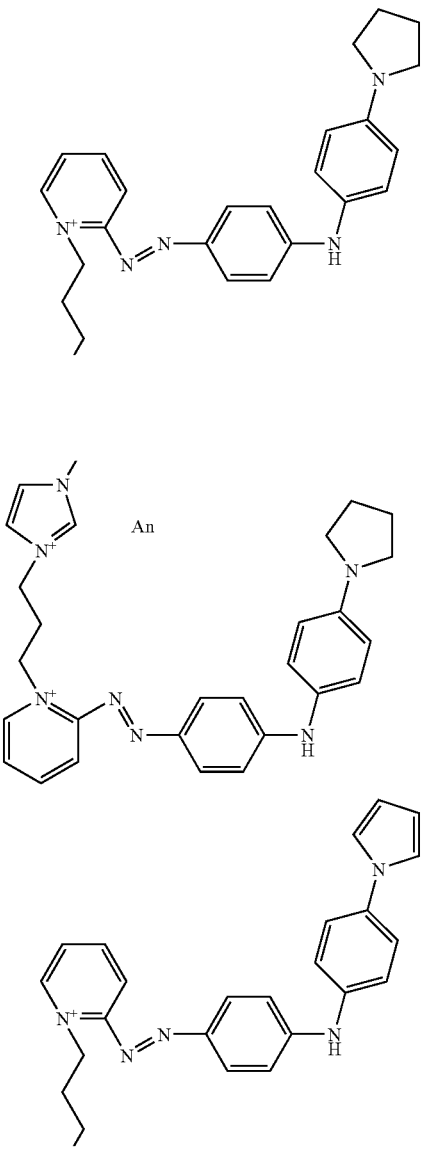
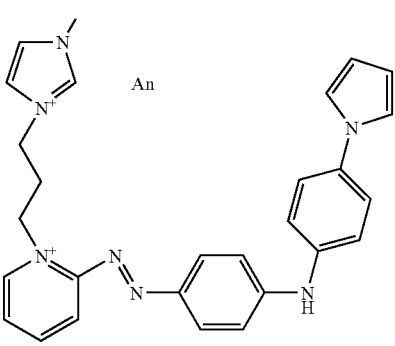

-continued
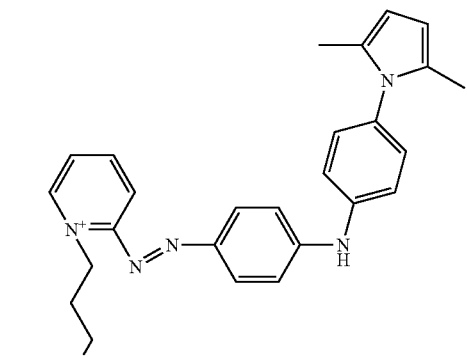
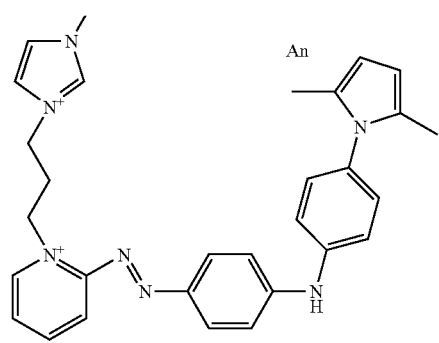
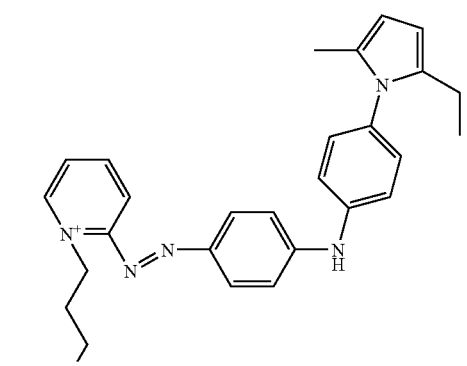
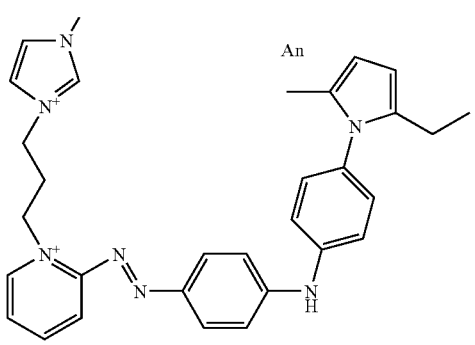
-continued
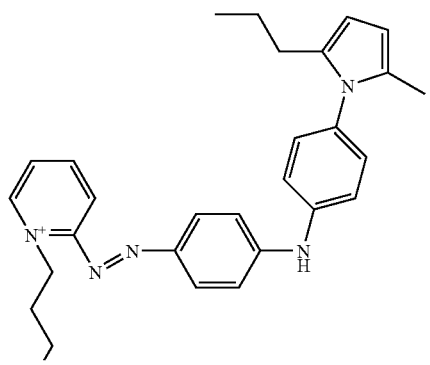
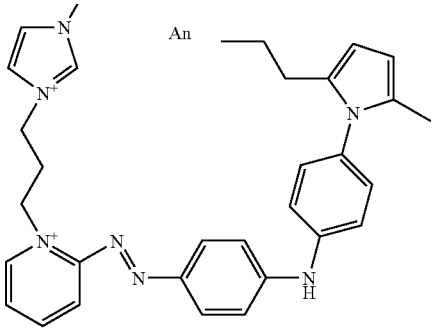
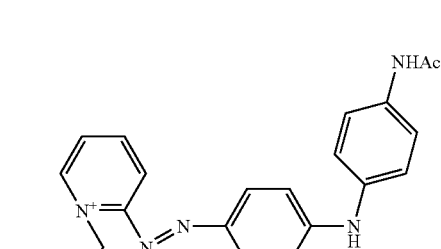
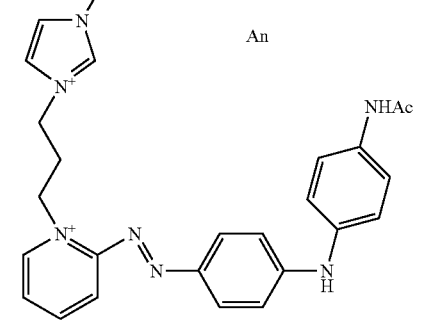

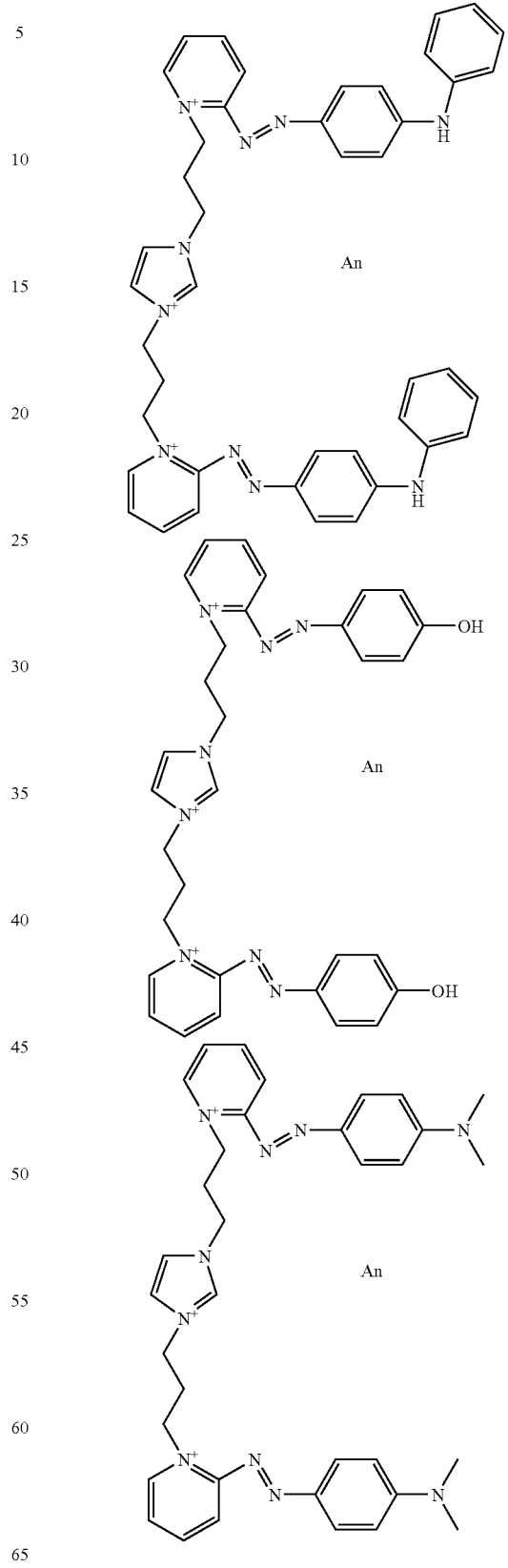

-continued
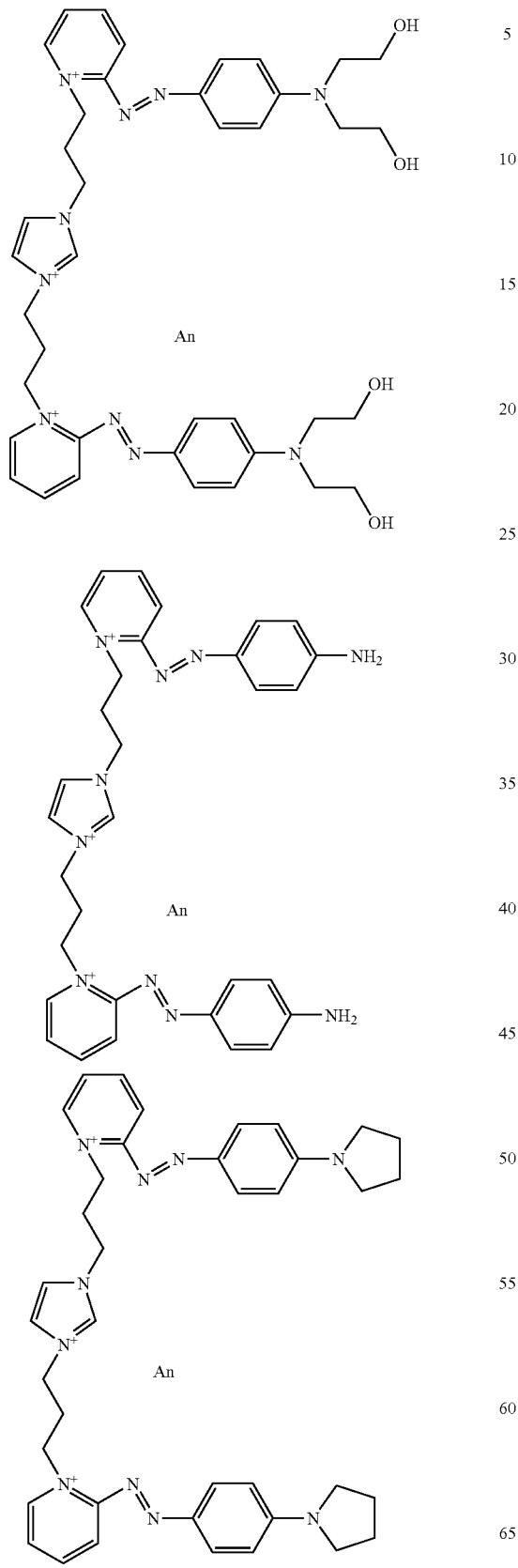

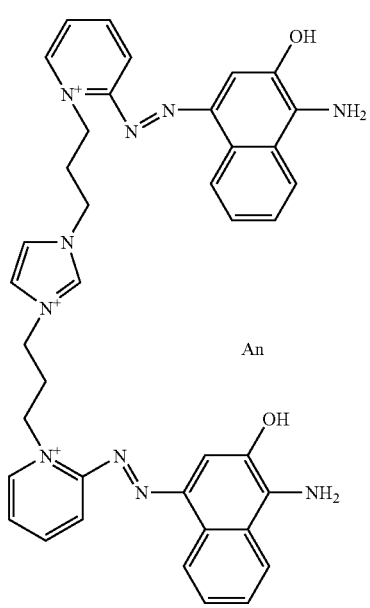
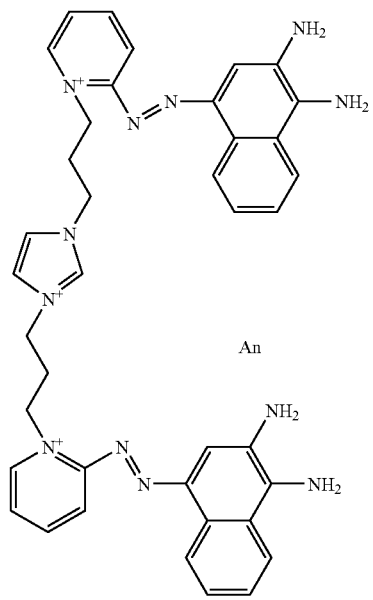
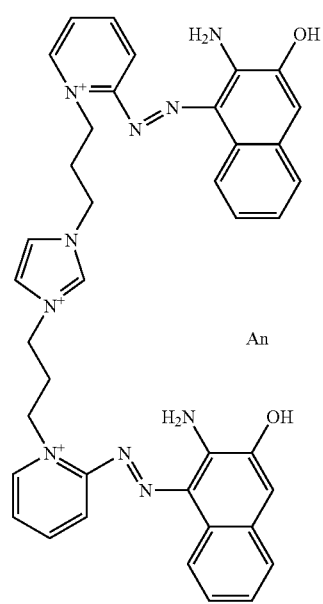
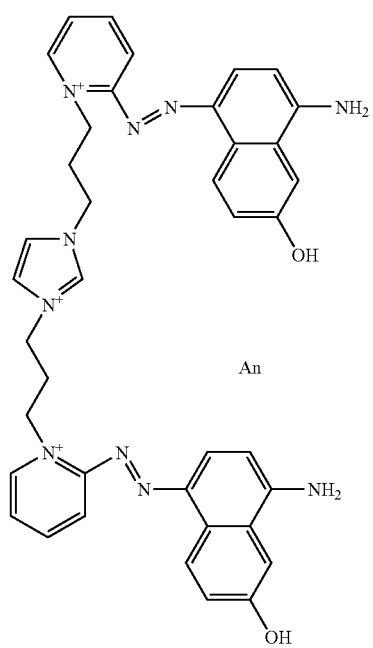

-continued

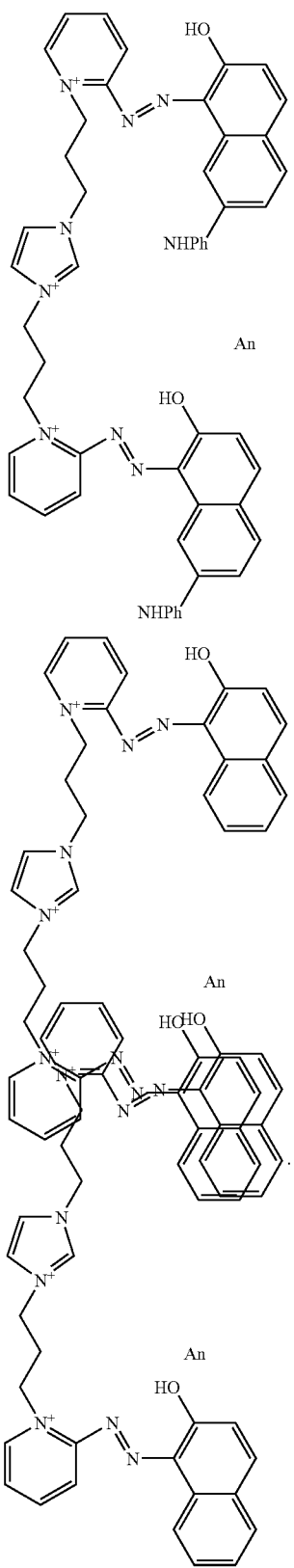

28. A dyeing composition comprising, in a medium appropriate for the dyeing of keratin fibers, as direct dye at least one compound of formula (I), the addition salts with an acid and/or the solvates thereof:

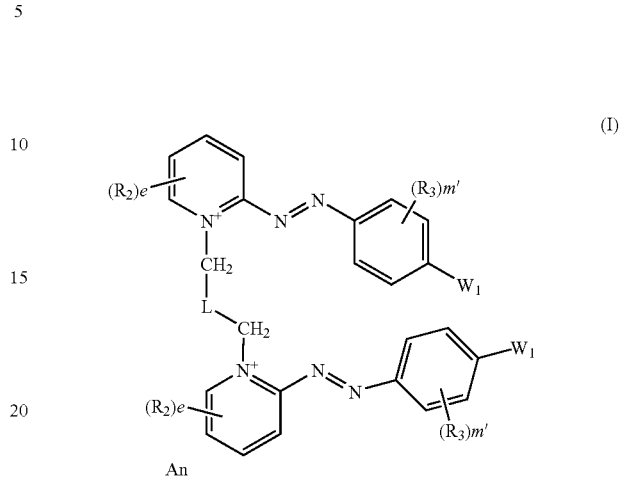

wherein:
the radicals $R_2$, which may be identical or different, are chosen from:
  optionally substituted $C_1$-$C_{16}$ alkyl radicals optionally interrupted by at least one heteroatom and/or by at least one group comprising at least one heteroatom, said alkyl radical being further optionally substituted by at least one group chosen from thio (—SH); $C_1$-$C_4$ thioalkyl; $C_1$-$C_4$ alkylsulphinyl and $C_1$-$C_4$ alkylsulphonyl groups;
  hydroxyl groups,
  $C_1$-$C_4$ alkoxy groups,
  $C_2$-$C_4$ (poly)hydroxyalkoxy groups;
  alkoxycarbonyl groups (RO—CO—) in which R is chosen from $C_1$-$C_4$ alkyl radicals,
  alkylcarbonyloxy radicals (RCO—O—) in which R is chosen from $C_1$-$C_4$ alkyl radicals, alkylcarbonyl radicals (R—CO—) in which R is chosen from $C_1$-$C_4$ alkyl radicals,
  amino groups,
  amino groups substituted by one or two identical or different $C_1$-$C_4$ alkyl radicals optionally carrying at least one hydroxyl group, it being possible for the two alkyl radicals optionally to form, with the nitrogen atom to which they are attached, a heterocycle comprising 1 to 3 heteroatoms chosen from N, O and S, and containing 5 to 7 ring members, which is saturated or unsaturated, aromatic or non-aromatic and is optionally substituted;
  alkylcarbonylamino groups (RCO—NR'—) in which the radical R is chosen from $C_1$-$C_4$ alkyl radicals, and the radical R' is chosen from hydrogen atoms and $C_1$-$C_4$ alkyl radicals;
  aminocarbonyl groups ((R)$_2$N—CO—) in which the radicals R, independently of one another, are chosen from hydrogen atoms and $C_1$-$C_4$ alkyl radicals;
  ureido groups (N(R)$_2$—CO—NR'—) in which the radicals R and R', independently of one another, are chosen from hydrogen atoms and $C_1$-$C_4$ alkyl radicals;
  aminosulphonyl groups ((R)$_2$N—SO$_2$—) in which the radicals R, independently of one another, are chosen from hydrogen atoms and $C_1$-$C_4$ alkyl radicals;

alkylsulphonylamino groups ($RSO_2$—NR'—) in which R is chosen from $C_1$-$C_4$ alkyl radicals, and R' is chosen from hydrogen atoms and $C_1$-$C_4$ alkyl radicals;
optionally substituted aryl radicals;
optionally substituted ($C_1$-$C_4$)alkylaryl radicals;
alkylsulphinyl groups (R—SO—) in which R is chosen from $C_1$-$C_4$ alkyl radicals;
alkylsulphonyl groups (R—$SO_2$—) in which R is chosen from $C_1$-$C_4$ alkyl radicals;
nitro groups;
cyano groups;
halogen atoms;
thio groups (HS—); and
alkylthio groups (RS—) in which the radical R is chosen from optionally substituted $C_1$-$C_4$ alkyl radicals;
e is an integer ranging from 0 to 4; when e is 2, the two radicals $R_2$ may optionally form, with the carbon atoms to which they are attached, a secondary ring, aromatic or non-aromatic, containing 5 or 6 ring members, which is optionally substituted by at least one identical or different group chosen from hydroxyl groups, $C_1$-$C_4$ alkyl groups, $C_1$-$C_4$ alkoxy groups, $C_2$-$C_4$ (poly)hydroxyalkoxy groups, amino groups, amino groups substituted by one or two identical or different $C_1$-$C_4$ alkyl radicals which optionally carry at least one hydroxyl group;
when e is less than 4, the unsubstituted carbon atom(s) of the heterocycle carry a hydrogen atom,
the radicals $R_3$, which may be identical or different, are chosen from:
  optionally substituted $C_1$-$C_{16}$ alkyl radicals optionally interrupted by at least one entity chosen from heteroatoms and groups comprising at least one heteroatom,
  hydroxyl groups,
  $C_1$-$C_4$ alkoxy groups,
  $C_2$-$C_4$ (poly)hydroxyalkoxy groups;
  alkoxycarbonyl groups (RO—CO—) in which R is chosen from $C_1$-$C_4$ alkyl radicals,
  alkylcarbonyloxy radicals (RCO—O—) in which R is chosen from $C_1$-$C_4$ alkyl radicals;
  alkylcarbonyl radicals (R—CO—) in which R is chosen from $C_1$-$C_4$ alkyl radicals;
  amino groups;
  amino groups substituted by one or two identical or different $C_1$-$C_4$ alkyl radicals optionally carrying at least one hydroxyl group; it being possible for the two alkyl radicals optionally to form, with the nitrogen atom to which they are attached, a heterocycle comprising 1 to 3 heteroatoms chosen from N, O and S, and containing 5 to 7 ring members, which is saturated or unsaturated, aromatic or non-aromatic and is optionally substituted;
  alkylcarbonylamino groups (RCO—NR'—) in which the radical R is chosen from $C_1$-$C_4$ alkyl radicals, and the radical R' is chosen from a hydrogen atom and $C_1$-$C_4$ alkyl radicals;
  aminocarbonyl groups (($R)_2$N—CO—) in which the radicals R, independently of one another, are chosen from hydrogen atoms and $C_1$-$C_4$ alkyl radicals;
  ureido groups (N($R)_2$—CO—NR'—) in which the radicals R and R', independently of one another, are chosen from hydrogen atoms and $C_1$-$C_4$ alkyl radicals;
  aminosulphonyl groups (($R)_2$N—$SO_2$—) in which the radicals R, independently of one another, are chosen from hydrogen atoms and $C_1$-$C_4$ alkyl radical;
  alkylsulphonylamino groups ($RSO_2$—NR'—) in which the radicals R and R', independently of one another, are chosen from hydrogen atoms and $C_1$-$C_4$ alkyl radicals;
  thio groups (HS—);
  alkylthio groups (RS—) in which the radical R is chosen from $C_1$-$C_4$ alkyl radicals;
  alkylsulphinyl groups (R—SO—) in which R is chosen from $C_1$-$C_4$ alkyl radicals;
  alkylsulphonyl groups (R—$SO_2$—) in which R is chosen from $C_1$-$C_4$ alkyl radicals;
  nitro groups;
  cyano groups; and
  halogen atoms;
m' is an integer ranging from 0 to 4; when m' is greater than or equal to 2, two adjacent radicals $R_3$ may form, with the carbon atoms to which they are attached, a secondary ring, aromatic or non-aromatic, containing 6 ring members, which is optionally substituted by at least one identical or different group chosen from: hydroxyl groups, $C_1$-$C_4$ alkyl groups, $C_1$-$C_4$ alkoxy groups, $C_2$-$C_4$ (poly)hydroxyalkoxy groups, $C_1$-$C_4$ alkylcarbonylamino groups, amino groups, amino groups substituted by one or two identical or different $C_1$-$C_4$ alkyl radicals which optionally carry at least one hydroxyl group,
when m' is less than 4, then the unsubstituted carbon atom(s) of the aromatic ring carry a hydrogen atom;
$W_1$ radicals, which are identical, are chosen from:
  hydrogen atoms,
  halogen atoms chosen from bromine, chlorine and fluorine, and
  —$NR_5R_6$, $OR_7$, —$NR_4$—Ph—$NR_5R_6$, —$NR_4$—Ph—$OR_7$, —O—Ph—$OR_7$ and —O—Ph—$NR_5R_6$ groups,
wherein:
  $R_4$ and $R_7$, which may be identical or different, are chosen from hydrogen atoms, optionally substituted $C_1$-$C_{20}$ alkyl radicals, optionally substituted $C_1$-$C_3$ aralkyl radicals, and optionally substituted phenyl radicals;
  $R_5$ and $R_6$, which may be identical or different, are chosen from hydrogen atoms, optionally substituted $C_1$-$C_{20}$ alkyl radicals, optionally substituted phenyl radicals, optionally substituted $C_1$-$C_3$ aralkyl radicals, and alkylcarbonyl radicals (R—CO—) in which R is chosen from $C_1$-$C_4$ alkyl radicals; and
  $R_5$ and $R_6$ may optionally form, with the nitrogen atom to which they are attached, a heterocycle comprising 1 to 3 heteroatoms, chosen from N, O and S, and containing 5 to 7 ring members, which is saturated or unsaturated, aromatic or non-aromatic and is optionally substituted; or
  $R_5$ and $R_6$ may optionally form, with the carbon atom of the aromatic ring adjacent to that to which —$NR_5R_6$ is attached, a 5- or 6-membered saturated heterocycle;
Ph is chosen from optionally substituted phenyl radicals;
L is a cationic or non-cationic linker;
wherein the electroneutrality of the compound of formula (I) is ensured by at least one cosmetically acceptable anion (An).

29. The dyeing composition according to claim 28, wherein the at least one compound of formula (I) is present in an amount, for each compound of formula (I), ranging from 0.001% to 20% by weight, relative to the total weight of the dyeing composition.

30. The dyeing composition according to claim 29, wherein the at least one compound of formula (I) is present in an amount, for each compound of formula (I), ranging from 0.01% to 10% by weight, relative to the total weight of the dyeing composition.

31. The dyeing composition according to claim 28, wherein the composition further comprises at least one additional direct dye, other than the direct dye of formula (I), at least one oxidation base optionally in combination with at least one coupler, or mixtures thereof.

32. The dyeing composition according to claim 31, wherein the at least one additional direct dye is a cationic or nonionic dye chosen from nitrobenzene dyes, azo, azomethine, methine, tetraazapentamethine, anthraquinone, naphthoquinone, benzoquinone, phenothiazine, indigoid, xanthene, phenanthridine, phthalocyanine dyes, dyes derived from triarylmethane, and natural dyes.

33. The dyeing composition according to claim 31, wherein the at least one oxidation base is chosen from p-phenylenediamines, bisphenylalkylenediamines, o-aminophenols, p-aminophenols and heterocyclic bases.

34. The dyeing composition according to claim 31, wherein the at least one coupler is chosen from m-aminophenols, m-phenylenediamines, m-diphenols, naphthols and heterocyclic couplers.

35. The dyeing composition according to claim 28, further comprising at least one oxidizing agent.

36. A method of coloring keratin fibers, comprising applying to the keratin fibers a composition comprising, in a medium appropriate for the dyeing of keratin fibers, as direct dye at least one compound of formula (I), the addition salts with an acid and/or the solvates thereof:

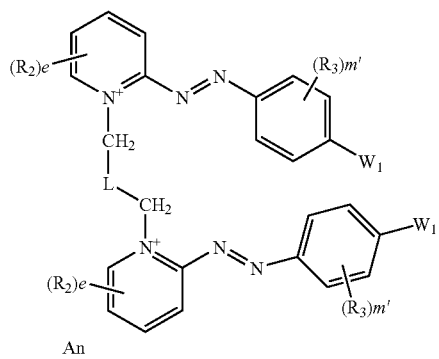

(I)

wherein:
the radicals $R_2$, which may be identical or different, are chosen from:
  optionally substituted $C_1$-$C_{16}$ alkyl radicals optionally interrupted by at least one heteroatom and/or by at least one group comprising at least one heteroatom, said alkyl radical being further optionally substituted by at least one group chosen from thio (—SH); $C_1$-$C_4$ thioalkyl; $C_1$-$C_4$ alkylsulphinyl and $C_1$-$C_4$ alkylsulphonyl groups;
  hydroxyl groups,
  $C_1$-$C_4$ alkoxy groups,
  $C_2$-$C_4$ (poly)hydroxyalkoxy groups;
  alkoxycarbonyl groups (RO—CO—) in which R is chosen from $C_1$-$C_4$ alkyl radicals,
  alkylcarbonyloxy radicals (RCO—O—) in which R is chosen from $C_1$-$C_4$ alkyl radicals,
  alkylcarbonyl radicals (R—CO—) in which R is chosen from $C_1$-$C_4$ alkyl radicals,
  amino groups,
  amino groups substituted by one or two identical or different $C_1$-$C_4$ alkyl radicals optionally carrying at least one hydroxyl group, it being possible for the two alkyl radicals optionally to form, with the nitrogen atom to which they are attached, a heterocycle comprising 1 to 3 heteroatoms chosen from N, O and S, and containing 5 to 7 ring members, which is saturated or unsaturated, aromatic or non-aromatic and is optionally substituted;
  alkylcarbonylamino groups (RCO—NR'—) in which the radical R is chosen from $C_1$-$C_4$ alkyl radicals, and the radical R' is chosen from hydrogen atoms and $C_1$-$C_4$ alkyl radicals;
  aminocarbonyl groups ((R)$_2$N—CO—) in which the radicals R, independently of one another, are chosen from hydrogen atoms and $C_1$-$C_4$ alkyl radicals;
  ureido groups (N(R)$_2$—CO—NR'—) in which the radicals R and R', independently of one another, are chosen from hydrogen atoms and $C_1$-$C_4$ alkyl radicals;
  aminosulphonyl groups ((R)$_2$N—SO$_2$—) in which the radicals R, independently of one another, are chosen from hydrogen atoms and $C_1$-$C_4$ alkyl radicals;
  alkylsulphonylamino groups (RSO$_2$—NR'—) in which R is chosen from $C_1$-$C_4$ alkyl radicals, and R' is chosen from hydrogen atoms and $C_1$-$C_4$ alkyl radicals;
  optionally substituted aryl radicals;
  optionally substituted ($C_1$-$C_4$)alkylaryl radicals;
  alkylsulphinyl groups (R—SO—) in which R is chosen from $C_1$-$C_4$ alkyl radicals;
  alkylsulphonyl groups (R—SO$_2$—) in which R is chosen from $C_1$-$C_4$ alkyl radicals;
  nitro groups;
  cyano groups;
  halogen atoms;
  thio groups (HS—); and
  alkylthio groups (RS—) in which the radical R is chosen from optionally substituted $C_1$-$C_4$ alkyl radicals;
  e is an integer ranging from 0 to 4; when e is 2, the two radicals $R_2$ may optionally form, with the carbon atoms to which they are attached, a secondary ring, aromatic or non-aromatic, containing 5 or 6 ring members, which is optionally substituted by at least one identical or different group chosen from hydroxyl groups, $C_1$-$C_4$ alkyl groups, $C_1$-$C_4$ alkoxy groups, $C_2$-$C_4$ (poly)hydroxyalkoxy groups, amino groups, amino groups substituted by one or two identical or different $C_1$-$C_4$ alkyl radicals which optionally carry at least one hydroxyl group;
when e is less than 4, the unsubstituted carbon atom(s) of the heterocycle carry a hydrogen atom,
the radicals $R_3$, which may be identical or different, are chosen from:
  optionally substituted $C_1$-$C_{16}$ alkyl radicals optionally interrupted by at least one entity chosen from heteroatoms and groups comprising at least one heteroatom,
  hydroxyl groups,
  $C_1$-$C_4$ alkoxy groups,
  $C_2$-$C_4$ (poly)hydroxyalkoxy groups;
  alkoxycarbonyl groups (RO—CO—) in which R is chosen from $C_1$-$C_4$ alkyl radicals,
  alkylcarbonyloxy radicals (RCO—O—) in which R is chosen from $C_1$-$C_4$ alkyl radicals;
  alkylcarbonyl radicals (R—CO—) in which R is chosen from $C_1$-$C_4$ alkyl radicals;
  amino groups;

amino groups substituted by one or two identical or different $C_1$-$C_4$ alkyl radicals optionally carrying at least one hydroxyl group; it being possible for the two alkyl radicals optionally to form, with the nitrogen atom to which they are attached, a heterocycle comprising 1 to 3 heteroatoms chosen from N, O and S, and containing 5 to 7 ring members, which is saturated or unsaturated, aromatic or non-aromatic and is optionally substituted;

alkylcarbonylamino groups (RCO—NR'—) in which the radical R is chosen from $C_1$-$C_4$ alkyl radicals, and the radical R' is chosen from a hydrogen atom and $C_1$-$C_4$ alkyl radicals;

aminocarbonyl groups $((R)_2N$—CO—) in which the radicals R, independently of one another, are chosen from hydrogen atoms and $C_1$-$C_4$ alkyl radicals;

ureido groups $(N(R)_2$—CO—NR'—) in which the radicals R and R', independently of one another, are chosen from hydrogen atoms and $C_1$-$C_4$ alkyl radicals;

aminosulphonyl groups $((R)_2N$—$SO_2$—) in which the radicals R, independently of one another, are chosen from hydrogen atoms and $C_1$-$C_4$ alkyl radical;

alkylsulphonylamino groups $(RSO_2$—NR'—) in which the radicals R and R', independently of one another, are chosen from hydrogen atoms and $C_1$-$C_4$ alkyl radicals;

thio groups (HS—);

alkylthio groups (RS—) in which the radical R is chosen from $C_1$-$C_4$ alkyl radicals;

alkylsulphinyl groups (R—SO—) in which R is chosen from $C_1$-$C_4$ alkyl radicals;

alkylsulphonyl groups (R—$SO_2$—) in which R is chosen from $C_1$-$C_4$ alkyl radicals;

nitro groups;

cyano groups; and halogen atoms;

m' is an integer ranging from 0 to 4; when m' is greater than or equal to 2, two adjacent radicals $R_3$ may form, with the carbon atoms to which they are attached, a secondary ring, aromatic or non-aromatic, containing 6 ring members, which is optionally substituted by at least one identical or different group chosen from: hydroxyl groups, $C_1$-$C_4$ alkyl groups, $C_1$-$C_4$ alkoxy groups, $C_2$-$C_4$ (poly)hydroxyalkoxy groups, $C_1$-$C_4$ alkylcarbonylamino groups, amino groups, amino groups substituted by one or two identical or different $C_1$-$C_4$ alkyl radicals which optionally carry at least one hydroxyl group, when m' is less than 4, then the unsubstituted carbon atom(s) of the aromatic ring carry a hydrogen atom;

$W_1$ radicals, which are identical, are chosen from:
hydrogen atoms,
halogen atoms chosen from bromine, chlorine and fluorine, and
—$NR_5R_6$, $OR_7$, —$NR_4$—Ph—$NR_5R_6$, —$NR_4$—Ph—$OR_7$, —O—Ph—$OR_7$ and —O—Ph—$NR_5R_6$ groups,
wherein:
$R_4$ and $R_7$, which may be identical or different, are chosen from hydrogen atoms, optionally substituted $C_1$-$C_{20}$ alkyl radicals, optionally substituted $C_1$-$C_3$ aralkyl radicals, and optionally substituted phenyl radicals;
$R_5$ and $R_6$, which may be identical or different, are chosen from hydrogen atoms, optionally substituted $C_1$-$C_{20}$ alkyl radicals, optionally substituted phenyl radicals, optionally substituted $C_1$-$C_3$ aralkyl radicals, and alkylcarbonyl radicals (R—CO—) in which R is chosen from $C_1$-$C_4$ alkyl radicals; and $R_5$ and $R_6$ may optionally form, with the nitrogen atom to which they are attached, a heterocycle comprising 1 to 3 heteroatoms, chosen from N, O and S, and containing 5 to 7 ring members, which is saturated or unsaturated, aromatic or non-aromatic and is optionally substituted; or $R_5$ and $R_6$ may optionally form, with the carbon atom of the aromatic ring adjacent to that to which —$NR_5R_6$ is attached, a 5- or 6-membered saturated heterocycle;

Ph is chosen from optionally substituted phenyl radicals;

L is a cationic or non-cationic linker;

wherein the electroneutrality of the compound of formula (I) is ensured by at least one cosmetically acceptable anion (An);

wherein said fibers, may be dry or wet, and the composition is left on the fibers for a period of time sufficient to give the desired coloring effect.

37. A multi-compartment kit, comprising
a first compartment containing a dyeing composition comprising, in a medium appropriate for the dyeing of keratin fibers, as direct dye at least one compound of formula (I), the addition salts with an acid and/or the solvates thereof:

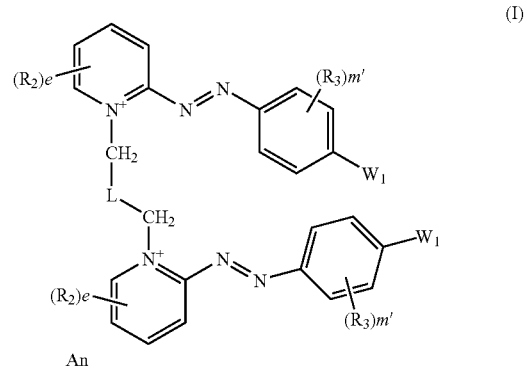

wherein:
the radicals $R_2$, which may be identical or different, are chosen from:
optionally substituted $C_1$-$C_{16}$ alkyl radicals optionally interrupted by at least one heteroatom and/or by at least one group comprising at least one heteroatom, said alkyl radical being further optionally substituted by at least one group chosen from thio (—SH); $C_1$-$C_4$ thioalkyl; $C_1$-$C_4$ alkylsulphinyl and $C_1$-$C_4$ alkylsulphonyl groups;
hydroxyl groups,
$C_1$-$C_4$ alkoxy groups,
$C_2$-$C_4$ (poly)hydroxyalkoxy groups;
alkoxycarbonyl groups (RO—CO—) in which R is chosen from $C_1$-$C_4$ alkyl radicals,
alkylcarbonyloxy radicals (RCO—O—) in which R is chosen from $C_1$-$C_4$ alkyl radicals,
alkylcarbonyl radicals (R—CO—) in which R is chosen from $C_1$-$C_4$ alkyl radicals,
amino groups,
amino groups substituted by one or two identical or different $C_1$-$C_4$ alkyl radicals optionally carrying at least one hydroxyl group, it being possible for the two alkyl radicals optionally to form, with the nitrogen atom to which they are attached, a heterocycle comprising 1 to 3 heteroatoms chosen from N, O and S, and containing 5 to 7 ring members, which is saturated or unsaturated, aromatic or non-aromatic and is optionally substituted;

alkylcarbonylamino groups (RCO—NR'—) in which the radical R is chosen from $C_1$-$C_4$ alkyl radicals, and the radical R' is chosen from hydrogen atoms and $C_1$-$C_4$ alkyl radicals;

aminocarbonyl groups ((R)$_2$N—CO—) in which the radicals R, independently of one another, are chosen from hydrogen atoms and $C_1$-$C_4$ alkyl radicals;

ureido groups (N(R)$_2$—CO—NR'—) in which the radicals R and R', independently of one another, are chosen from hydrogen atoms and $C_1$-$C_4$ alkyl radicals;

aminosulphonyl groups ((R)$_2$N—SO$_2$—) in which the radicals R, independently of one another, are chosen from hydrogen atoms and $C_1$-$C_4$ alkyl radicals;

alkylsulphonylamino groups (RSO$_2$—NR'—) in which R is chosen from $C_1$-$C_4$ alkyl radicals, and R' is chosen from hydrogen atoms and $C_1$-$C_4$ alkyl radicals;

optionally substituted aryl radicals;

optionally substituted ($C_1$-$C_4$)alkylaryl radicals;

alkylsulphinyl groups (R—SO—) in which R is chosen from $C_1$-$C_4$ alkyl radicals;

alkylsulphonyl groups (R—SO$_2$—) in which R is chosen from $C_1$-$C_4$ alkyl radicals;

nitro groups;

cyano groups;

halogen atoms;

thio groups (HS—); and alkylthio groups (RS—) in which the radical R is chosen from optionally substituted $C_1$-$C_4$ alkyl radicals;

e is an integer ranging from 0 to 4; when e is 2, the two radicals R$_2$ may optionally form, with the carbon atoms to which they are attached, a secondary ring, aromatic or non-aromatic, containing 5 or 6 ring members, which is optionally substituted by at least one identical or different group chosen from hydroxyl groups, $C_1$-$C_4$ alkyl groups, $C_1$-$C_4$ alkoxy groups, $C_2$-$C_4$ (poly)hydroxyalkoxy groups, amino groups, amino groups substituted by one or two identical or different $C_1$-$C_4$ alkyl radicals which optionally carry at least one hydroxyl group;

when e is less than 4, the unsubstituted carbon atom(s) of the heterocycle carry a hydrogen atom, the radicals R$_3$, which may be identical or different, are chosen from:

optionally substituted $C_1$-$C_{16}$ alkyl radicals optionally interrupted by at least one entity chosen from heteroatoms and groups comprising at least one heteroatom, hydroxyl groups, $C_1$-$C_4$ alkoxy groups, $C_2$-$C_4$ (poly)hydroxyalkoxy groups;

alkoxycarbonyl groups (RO—CO—) in which R is chosen from $C_1$-$C_4$ alkyl radicals, alkylcarbonyloxy radicals (RCO—O—) in which R is chosen from $C_1$-$C_4$ alkyl radicals;

alkylcarbonyl radicals (R—CO—) in which R is chosen from $C_1$-$C_4$ alkyl radicals;

amino groups;

amino groups substituted by one or two identical or different $C_1$-$C_4$ alkyl radicals optionally carrying at least one hydroxyl group; it being possible for the two alkyl radicals optionally to form, with the nitrogen atom to which they are attached, a heterocycle comprising 1 to 3 heteroatoms chosen from N, O and S, and containing 5 to 7 ring members, which is saturated or unsaturated, aromatic or non-aromatic and is optionally substituted;

alkylcarbonylamino groups (RCO—NR'—) in which the radical R is chosen from $C_1$-$C_4$ alkyl radicals, and the radical R' is chosen from a hydrogen atom and $C_1$-$C_4$ alkyl radicals;

aminocarbonyl groups ((R)$_2$N—CO—) in which the radicals R, independently of one another, are chosen from hydrogen atoms and $C_1$-$C_4$ alkyl radicals;

ureido groups (N(R)$_2$—CO—NR'—) in which the radicals R and R', independently of one another, are chosen from hydrogen atoms and $C_1$-$C_4$ alkyl radicals;

aminosulphonyl groups ((R)$_2$N—SO$_2$—) in which the radicals R, independently of one another, are chosen from hydrogen atoms and $C_1$-$C_4$ alkyl radical;

alkylsulphonylamino groups (RSO$_2$—NR'—) in which the radicals R and R', independently of one another, are chosen from hydrogen atoms and $C_1$-$C_4$ alkyl radicals;

thio groups (HS—);

alkylthio groups (RS—) in which the radical R is chosen from $C_1$-$C_4$ alkyl radicals;

alkylsulphinyl groups (R—SO—) in which R is chosen from $C_1$-$C_4$ alkyl radicals;

alkylsulphonyl groups (R—SO$_2$—) in which R is chosen from $C_1$-$C_4$ alkyl radicals;

nitro groups;

cyano groups; and halogen atoms;

m' is an integer ranging from 0 to 4; when m' is greater than or equal to 2, two adjacent radicals R$_3$ may form, with the carbon atoms to which they are attached, a secondary ring, aromatic or non-aromatic, containing 6 ring members, which is optionally substituted by at least one identical or different group chosen from: hydroxyl groups, $C_1$-$C_4$ alkyl groups, $C_1$-$C_4$ alkoxy groups, $C_2$-$C_4$ (poly)hydroxyalkoxy groups, $C_1$-$C_4$ alkylcarbonylamino groups, amino groups, amino groups substituted by one or two identical or different $C_1$-$C_4$ alkyl radicals which optionally carry at least one hydroxyl group, when m' is less than 4, then the unsubstituted carbon atom(s) of the aromatic ring carry a hydrogen atom;

W$_1$ radicals, which are identical, are chosen from:

hydrogen atoms, halogen atoms chosen from bromine, chlorine and fluorine, and

—NR$_5$R$_6$, OR$_7$, —NR$_4$—Ph—NR$_5$R$_6$, —NR$_4$—Ph—OR$_7$, —O—Ph—OR$_7$ and —O—Ph—NR$_5$R$_6$ groups, wherein:

R$_4$ and R$_7$, which may be identical or different, are chosen from hydrogen atoms, optionally substituted $C_1$-$C_{20}$ alkyl radicals, optionally substituted $C_1$-$C_3$ aralkyl radicals, and optionally substituted phenyl radicals;

R$_5$ and R$_6$, which may be identical or different, are chosen from hydrogen atoms, optionally substituted $C_1$-$C_{20}$ alkyl radicals, optionally substituted phenyl radicals, optionally substituted $C_1$-$C_3$ aralkyl radicals, and alkylcarbonyl radicals (R—CO—) in which R is chosen from $C_1$-$C_4$ alkyl radicals; and $R_5$ and $R_6$ may optionally form, with the nitrogen atom to which they are attached, a heterocycle comprising 1 to 3 heteroatoms, chosen from N, O and S, and containing 5 to 7 ring members, which is saturated or unsaturated, aromatic or non-aromatic and is optionally substituted; or $R_5$ and $R_6$ may optionally form, with the carbon atom of the aromatic ring adjacent to that to which —$NR_5R_6$ is attached, a 5- or 6-membered saturated heterocycle;

Ph is chosen from optionally substituted phenyl radicals;

L is a cationic or non-cationic linker;

wherein the electroneutrality of the compound of formula (I) is ensured by at least one cosmetically acceptable anion (An); and a second compartment containing a composition comprising at least one oxidizing agent.

* * * * *

UNITED STATES PATENT AND TRADEMARK OFFICE
CERTIFICATE OF CORRECTION

PATENT NO. : 7,247,713 B2  Page 1 of 5
APPLICATION NO. : 11/300271
DATED : July 24, 2007
INVENTOR(S) : Hervé David et al.

It is certified that error appears in the above-identified patent and that said Letters Patent is hereby corrected as shown below:

In claim 12, column 75, lines 13-14, "substituted the alkyl radical" should read --substituted, the alkyl radical--.

In claim 26, column 78, lines 5-31, in the structure for formula (I'''):

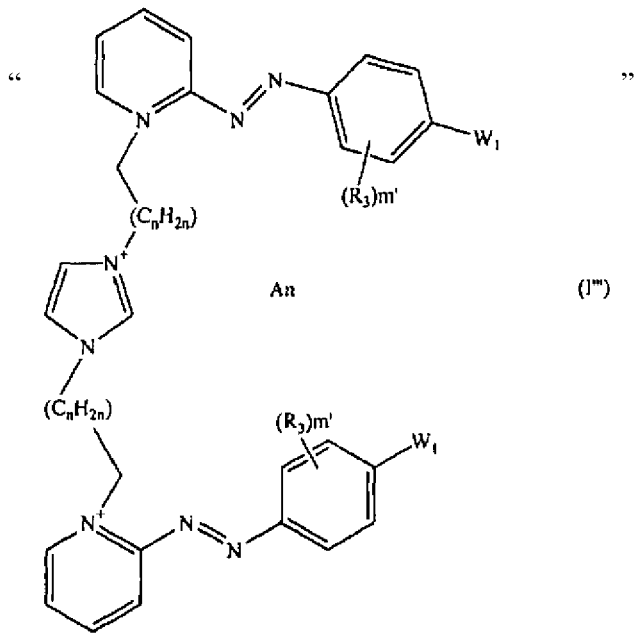

n = integer between 1 and 5

UNITED STATES PATENT AND TRADEMARK OFFICE
CERTIFICATE OF CORRECTION

PATENT NO. : 7,247,713 B2
APPLICATION NO. : 11/300271
DATED : July 24, 2007
INVENTOR(S) : Hervé David et al.

It is certified that error appears in the above-identified patent and that said Letters Patent is hereby corrected as shown below:

should read

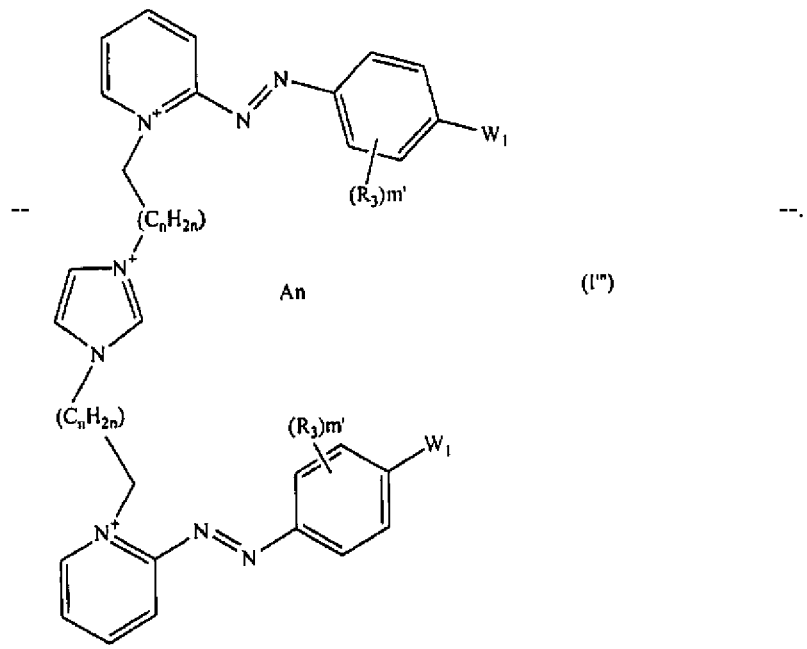

-- -- .

(I''')

n = integer between 1 and 5

UNITED STATES PATENT AND TRADEMARK OFFICE
CERTIFICATE OF CORRECTION

PATENT NO. : 7,247,713 B2  Page 3 of 5
APPLICATION NO. : 11/300271
DATED : July 24, 2007
INVENTOR(S) : Hervé David et al.

It is certified that error appears in the above-identified patent and that said Letters Patent is hereby corrected as shown below:

In claim 27, column 81, in the structure between lines 45-65,

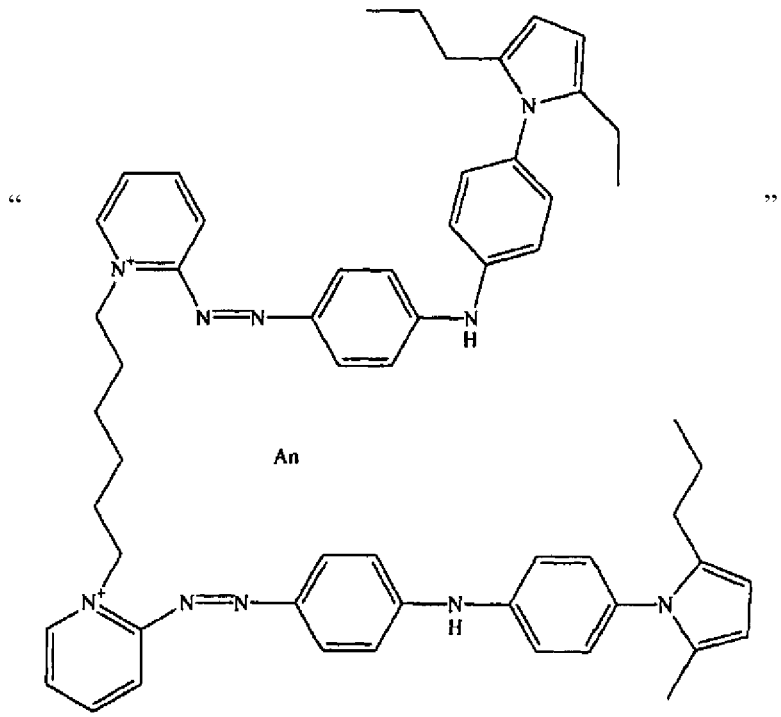

should read

UNITED STATES PATENT AND TRADEMARK OFFICE
CERTIFICATE OF CORRECTION

PATENT NO. : 7,247,713 B2  Page 4 of 5
APPLICATION NO. : 11/300271
DATED : July 24, 2007
INVENTOR(S) : Hervé David et al.

It is certified that error appears in the above-identified patent and that said Letters Patent is hereby corrected as shown below:

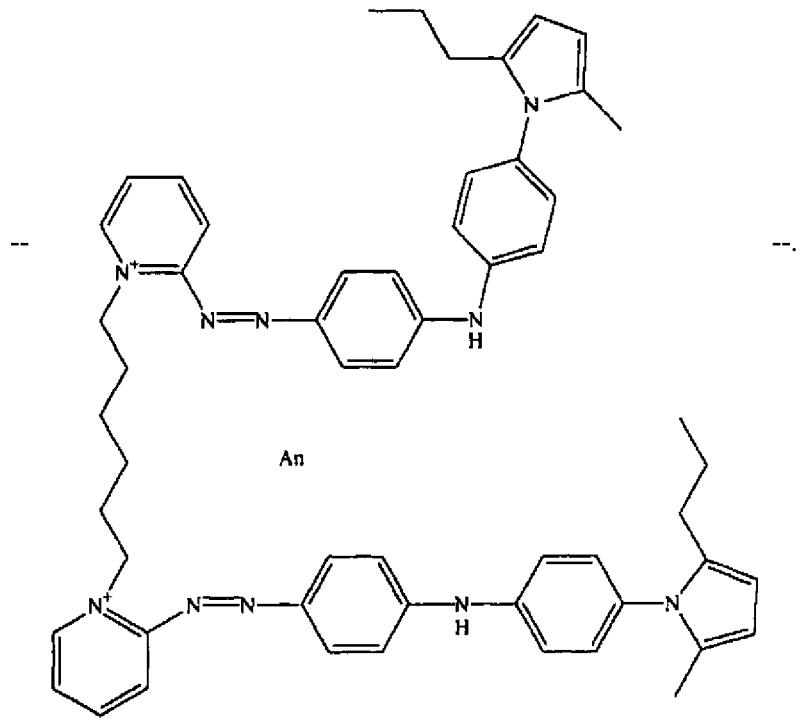

UNITED STATES PATENT AND TRADEMARK OFFICE
CERTIFICATE OF CORRECTION

PATENT NO. : 7,247,713 B2  Page 5 of 5
APPLICATION NO. : 11/300271
DATED : July 24, 2007
INVENTOR(S) : Hervé David et al.

It is certified that error appears in the above-identified patent and that said Letters Patent is hereby corrected as shown below:

In claim 27, column 111, delete the structures between lines 29-65 and insert therefor:

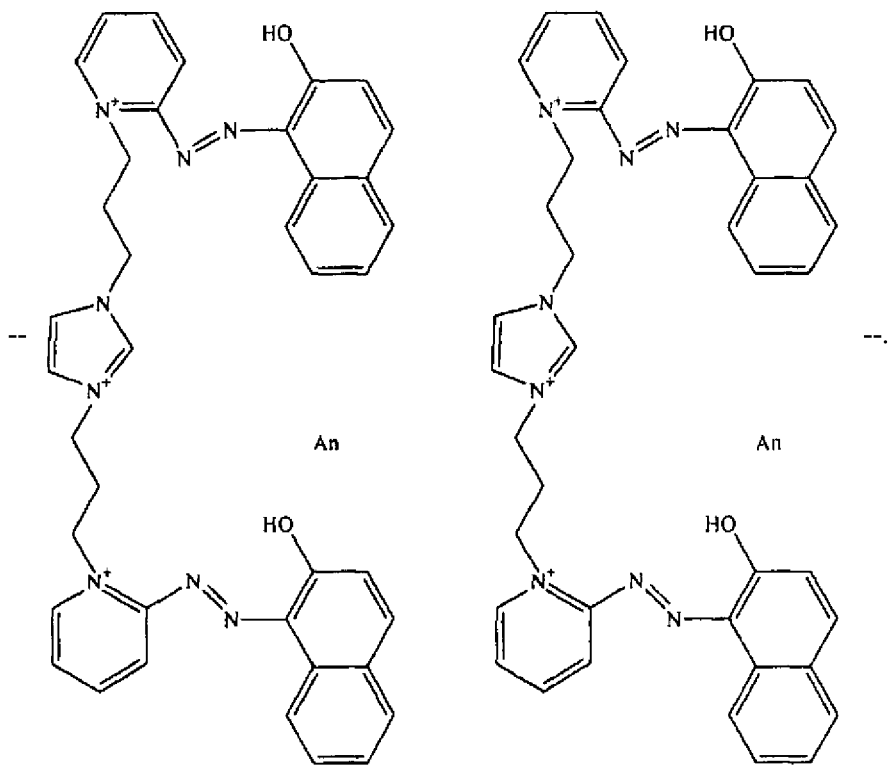

Signed and Sealed this

Twenty-fourth Day of March, 2009

JOHN DOLL
*Acting Director of the United States Patent and Trademark Office*